United States Patent
Buck et al.

(10) Patent No.: US 12,171,917 B1
(45) Date of Patent: Dec. 24, 2024

(54) DEVICES FOR BLOOD CAPTURE AND REINTRODUCTION DURING ASPIRATION PROCEDURE

(71) Applicant: Imperative Care, Inc., Campbell, CA (US)

(72) Inventors: Michael Buck, Menlo Park, CA (US); Julia Fox, San Carlos, CA (US); James Jacobs, Danville, CA (US)

(73) Assignee: Imperative Care, Inc., Campbell, CA (US)

( * ) Notice: Subject to any disclaimer, the term of this patent is extended or adjusted under 35 U.S.C. 154(b) by 0 days.

(21) Appl. No.: 18/407,218

(22) Filed: Jan. 8, 2024

(51) Int. Cl.
*A61M 1/02* (2006.01)
*A61M 1/00* (2006.01)

(52) U.S. Cl.
CPC .......... *A61M 1/0281* (2013.01); *A61M 1/631* (2021.05); *A61M 1/79* (2021.05); *A61M 2202/0021* (2013.01); *A61M 2202/0413* (2013.01); *A61M 2205/10* (2013.01); *A61M 2205/7545* (2013.01)

(58) Field of Classification Search
CPC ...... A61M 1/0281; A61M 1/631; A61M 1/79; A61M 2202/0021; A61M 2202/0413; A61M 2205/10; A61M 2205/7545
See application file for complete search history.

(56) References Cited

U.S. PATENT DOCUMENTS

| | | |
|---|---|---|
| 2,434,835 A | 1/1948 | Colley |
| 2,846,179 A | 8/1958 | Monckton |
| 4,030,503 A | 6/1977 | Clark, III |
| 4,412,669 A | 11/1983 | Hanyu |
| 4,435,170 A * | 3/1984 | Laszczower ........ A61M 1/7415 604/6.15 |
| 4,523,737 A | 6/1985 | Wentworth |
| 4,611,594 A | 9/1986 | Grayhack et al. |
| 4,626,248 A | 12/1986 | Scheller |

(Continued)

FOREIGN PATENT DOCUMENTS

| | | |
|---|---|---|
| CA | 2599104 | 2/2008 |
| CN | 101123918 A | 2/2008 |

(Continued)

OTHER PUBLICATIONS

Angiodynamics, Inc., 2015, AngioVac: Cannula and Circuit, product brochure, 6 pp.

(Continued)

*Primary Examiner* — Leslie R Deak
(74) *Attorney, Agent, or Firm* — Knobbe, Martens, Olson & Bear, LLP

(57) ABSTRACT

A blood reintroduction system may include a canister configured to collect blood. The system may include an inlet configured to be fluidly connected to a first tubing in fluid communication with an aspiration system configured to apply aspiration to a vasculature of a patient. The system may include a first outlet configured to be fluidly connected to a second tubing in fluid communication with an aspiration pump. The system may include a second outlet configured to interact with a blood reintroduction device, wherein the blood reintroduction device is configured to withdraw the blood collected inside the canister. The system may include a filter positioned inside a flow path leading to the second outlet.

26 Claims, 35 Drawing Sheets

(56) References Cited

U.S. PATENT DOCUMENTS

| | | | |
|---|---|---|---|
| 4,634,421 A | 1/1987 | Hegemann | |
| 4,735,606 A | 4/1988 | Davison | |
| 4,767,399 A | 8/1988 | Bollish | |
| 4,810,582 A | 3/1989 | Gould et al. | |
| 4,830,023 A | 5/1989 | De Toledo et al. | |
| 4,844,064 A | 7/1989 | Thimsen et al. | |
| 4,898,575 A | 2/1990 | Fischell et al. | |
| 4,923,462 A | 5/1990 | Stevens | |
| 4,981,478 A | 1/1991 | Evard et al. | |
| 5,011,488 A | 4/1991 | Ginsburg | |
| 5,035,688 A | 7/1991 | Inui | |
| 5,049,146 A * | 9/1991 | Bringham | A61M 1/3632 604/406 |
| 5,131,391 A | 7/1992 | Sakai et al. | |
| 5,197,485 A | 3/1993 | Grooters | |
| 5,197,955 A | 3/1993 | Stephens et al. | |
| 5,226,909 A | 7/1993 | Evans et al. | |
| 5,243,997 A | 9/1993 | Uflacker et al. | |
| 5,279,596 A | 1/1994 | Castaneda et al. | |
| 5,284,148 A | 2/1994 | Dias | |
| 5,304,143 A | 4/1994 | Green et al. | |
| 5,308,327 A | 5/1994 | Heaven et al. | |
| 5,417,697 A | 5/1995 | Wilk et al. | |
| 5,423,846 A | 6/1995 | Fischell | |
| 5,429,136 A | 7/1995 | Milo et al. | |
| 5,429,616 A | 7/1995 | Schaffer | |
| 5,441,484 A | 8/1995 | O'Donnell | |
| 5,474,563 A | 12/1995 | Myler et al. | |
| 5,536,242 A | 7/1996 | Willard et al. | |
| 5,549,119 A | 8/1996 | Solar | |
| 5,569,178 A | 10/1996 | Henley | |
| 5,569,277 A | 10/1996 | Evans et al. | |
| 5,591,187 A | 1/1997 | Dekel | |
| 5,609,303 A | 3/1997 | Cohen | |
| 5,638,818 A | 6/1997 | Diab et al. | |
| 5,662,622 A | 9/1997 | Gore et al. | |
| 5,666,969 A | 9/1997 | Urick et al. | |
| 5,702,373 A | 12/1997 | Samson | |
| 5,704,927 A | 1/1998 | Gillette et al. | |
| 5,713,848 A | 2/1998 | Dubrul et al. | |
| 5,766,191 A | 6/1998 | Trerotola | |
| 5,792,124 A | 8/1998 | Horrigan et al. | |
| 5,827,242 A | 10/1998 | Follmer et al. | |
| 5,873,882 A | 2/1999 | Straub et al. | |
| 5,876,414 A | 3/1999 | Straub | |
| 5,885,209 A | 3/1999 | Green | |
| 5,885,259 A | 3/1999 | Berg | |
| 5,891,114 A | 4/1999 | Chien et al. | |
| 5,893,869 A | 4/1999 | Barnhart et al. | |
| 5,895,398 A | 4/1999 | Wensel et al. | |
| 5,899,892 A | 5/1999 | Mortier et al. | |
| 5,916,192 A | 6/1999 | Nita et al. | |
| 5,935,112 A | 8/1999 | Stevens | |
| 5,938,645 A | 8/1999 | Gordon | |
| 5,951,539 A | 9/1999 | Nita | |
| 6,007,530 A | 12/1999 | Dornhofer et al. | |
| 6,056,837 A | 5/2000 | Lieber et al. | |
| 6,090,118 A | 7/2000 | McGuckin, Jr. | |
| 6,106,488 A | 8/2000 | Fleming et al. | |
| 6,143,009 A | 11/2000 | Shiber | |
| 6,152,909 A | 11/2000 | Bagaoisan et al. | |
| 6,171,295 B1 | 1/2001 | Garabedian et al. | |
| 6,197,014 B1 | 3/2001 | Samson et al. | |
| 6,197,016 B1 | 3/2001 | Fourkas et al. | |
| 6,217,557 B1 | 4/2001 | Hakansson et al. | |
| 6,221,038 B1 | 4/2001 | Brisken | |
| 6,228,046 B1 | 5/2001 | Brisken | |
| 6,258,052 B1 | 7/2001 | Milo | |
| 6,285,903 B1 | 9/2001 | Rosenthal et al. | |
| 6,322,534 B1 | 11/2001 | Shkolnik | |
| 6,355,027 B1 | 3/2002 | Le et al. | |
| 6,394,976 B1 | 5/2002 | Winston et al. | |
| 6,400,971 B1 | 6/2002 | Firanov et al. | |
| 6,451,036 B1 | 6/2002 | Heitzmann et al. | |
| 6,451,005 B1 | 9/2002 | Saitou et al. | |
| 6,481,439 B1 | 11/2002 | Lewis | |
| 6,482,217 B1 | 11/2002 | Pintor et al. | |
| 6,488,637 B1 | 12/2002 | Eder et al. | |
| 6,497,010 B1 | 12/2002 | Klor et al. | |
| 6,511,492 B1 | 1/2003 | Rosenbluth et al. | |
| 6,524,301 B1 | 2/2003 | Wilson et al. | |
| 6,524,303 B1 | 2/2003 | Garibaldi et al. | |
| 6,520,934 B1 | 3/2003 | Lee et al. | |
| 6,533,751 B2 | 3/2003 | Cragg et al. | |
| 6,554,820 B1 | 4/2003 | Wendlandt et al. | |
| 6,569,148 B2 | 5/2003 | Bagaoisan et al. | |
| 6,582,440 B1 | 6/2003 | Brumbach | |
| 6,613,017 B1 | 9/2003 | Mickley | |
| 6,663,613 B1 | 12/2003 | Evans et al. | |
| 6,666,874 B2 | 12/2003 | Heitzmann | |
| 6,669,670 B1 | 12/2003 | Muni et al. | |
| 6,719,717 B1 * | 4/2004 | Johnson | A61M 1/36 604/9 |
| 6,767,353 B1 | 7/2004 | Shiber | |
| 6,776,770 B1 | 8/2004 | Trerotola | |
| 6,796,976 B1 | 9/2004 | Chin et al. | |
| 6,805,692 B2 | 10/2004 | Muni et al. | |
| 6,824,550 B1 | 11/2004 | Pintor et al. | |
| 6,824,553 B1 | 11/2004 | Samson et al. | |
| 6,860,463 B2 | 2/2005 | Hartley | |
| 6,871,660 B2 | 3/2005 | Hampsch | |
| 6,929,633 B2 | 8/2005 | Evans et al. | |
| 6,936,025 B1 | 8/2005 | Evans et al. | |
| 6,966,896 B2 | 11/2005 | Kurth et al. | |
| 7,004,954 B1 | 2/2006 | Voss et al. | |
| 7,018,372 B2 | 3/2006 | Casey et al. | |
| 7,029,482 B1 | 4/2006 | Vargas et al. | |
| 7,112,298 B2 | 9/2006 | Kampa et al. | |
| 7,172,572 B2 | 2/2007 | Diamond et al. | |
| 7,204,810 B2 | 4/2007 | Hynes et al. | |
| 7,223,274 B2 | 5/2007 | Vargas et al. | |
| 7,235,088 B2 | 6/2007 | Pintor et al. | |
| 7,250,042 B2 | 7/2007 | Kataishi et al. | |
| 7,306,585 B2 | 12/2007 | Ross | |
| 7,335,216 B2 | 2/2008 | Bender et al. | |
| 7,431,717 B2 | 10/2008 | Gonzales | |
| 7,469,727 B2 | 12/2008 | Marshall | |
| 7,507,229 B2 | 3/2009 | Hewitt et al. | |
| 7,601,138 B2 | 10/2009 | Goebel et al. | |
| 7,635,353 B2 | 12/2009 | Guramy et al. | |
| 7,648,120 B1 | 1/2010 | Kota et al. | |
| 7,715,903 B2 | 5/2010 | Hartley et al. | |
| 7,722,552 B2 | 5/2010 | Aimi et al. | |
| 7,763,196 B2 | 7/2010 | Goebel et al. | |
| 7,780,649 B2 | 8/2010 | Shippert | |
| 7,842,055 B2 | 11/2010 | Pintor et al. | |
| 7,850,623 B2 | 12/2010 | Griffin et al. | |
| 7,938,820 B2 | 5/2011 | Webster et al. | |
| 7,942,852 B2 | 5/2011 | Mas et al. | |
| 7,947,012 B2 | 5/2011 | Spurchise et al. | |
| 7,998,104 B2 | 8/2011 | Chang | |
| 8,021,351 B2 | 9/2011 | Boldenow et al. | |
| 8,062,316 B2 | 11/2011 | Patel et al. | |
| 8,075,510 B2 | 12/2011 | Aklog et al. | |
| 8,114,106 B2 | 2/2012 | Straub | |
| 8,114,110 B2 | 2/2012 | Bednaret et al. | |
| 8,123,731 B2 | 2/2012 | Ryan | |
| 8,157,103 B2 | 4/2012 | Eagle et al. | |
| 8,157,760 B2 | 4/2012 | Criado et al. | |
| 8,241,264 B2 | 8/2012 | Sjögren et al. | |
| 8,267,897 B2 | 9/2012 | Wells | |
| 8,282,069 B2 | 10/2012 | Landry | |
| 8,298,591 B2 | 10/2012 | Srivastava et al. | |
| 8,308,655 B2 | 11/2012 | Grigoryants | |
| 8,317,773 B2 | 11/2012 | Appling et al. | |
| 8,353,850 B2 | 1/2013 | Ressemann et al. | |
| 8,361,095 B2 | 1/2013 | Osborne | |
| 8,366,408 B2 | 2/2013 | Wago et al. | |
| 8,382,660 B2 | 2/2013 | Okada | |
| 8,382,739 B2 | 2/2013 | Walak et al. | |
| 8,394,078 B2 | 3/2013 | Torrance et al. | |
| 8,403,912 B2 | 3/2013 | McFerran et al. | |
| 8,425,455 B2 | 4/2013 | Nentwick | |
| 8,430,845 B2 | 4/2013 | Wahr et al. | |

(56) References Cited

U.S. PATENT DOCUMENTS

| | | |
|---|---|---|
| 8,460,312 B2 | 6/2013 | Bose et al. |
| 8,468,919 B2 | 6/2013 | Christian et al. |
| 8,475,487 B2 | 7/2013 | Bonnette et al. |
| 8,485,969 B2 | 7/2013 | Grayzel et al. |
| 8,506,512 B2 | 8/2013 | Aklog et al. |
| 8,517,955 B2 | 8/2013 | Keast et al. |
| 8,535,283 B2 | 9/2013 | Heaton et al. |
| 8,545,432 B2 | 10/2013 | Renati et al. |
| 8,551,021 B2 | 10/2013 | Voeller et al. |
| 8,568,432 B2 | 10/2013 | Straub |
| 8,585,596 B1 | 11/2013 | Flaherty et al. |
| 8,608,754 B2 | 12/2013 | Wensel et al. |
| 8,617,103 B2 | 12/2013 | Vreeman |
| 8,663,259 B2 | 3/2014 | Levine et al. |
| 8,684,963 B2 | 4/2014 | Qiu et al. |
| 8,690,907 B1 | 4/2014 | Janardhan et al. |
| 8,696,698 B2 | 4/2014 | Chomas et al. |
| 8,708,933 B2 | 4/2014 | Cornish et al. |
| 8,734,374 B2 | 5/2014 | Aklog et al. |
| 8,758,325 B2 | 6/2014 | Webster et al. |
| 8,764,779 B2 | 7/2014 | Levine et al. |
| 8,784,337 B2 | 7/2014 | Voeller et al. |
| 8,831,707 B2 | 9/2014 | Tekulve et al. |
| 8,858,518 B2 | 10/2014 | Shafer et al. |
| 8,864,792 B2 | 10/2014 | Eckhouse et al. |
| 8,900,179 B2 | 12/2014 | Jenson et al. |
| 8,900,257 B2 | 12/2014 | Straub et al. |
| 8,992,506 B2 | 3/2015 | Gulachenski |
| 8,996,095 B2 | 3/2015 | Anderson et al. |
| 8,998,946 B2 | 4/2015 | Morero |
| 9,005,166 B2 | 4/2015 | Uber, III et al. |
| 9,014,786 B2 | 4/2015 | Carmeli et al. |
| 9,023,070 B2 | 5/2015 | Levine et al. |
| 9,067,332 B2 | 6/2015 | Lippert et al. |
| 9,067,333 B2 | 6/2015 | Lippert et al. |
| 9,089,672 B2 | 7/2015 | Hendriksen et al. |
| 9,107,691 B2 | 8/2015 | Fojtik |
| 9,126,018 B1 | 9/2015 | Garrison |
| 9,138,307 B2 | 9/2015 | Valaie |
| 9,168,353 B2 | 10/2015 | Chambers |
| 9,199,009 B2 | 12/2015 | Krensky et al. |
| 9,199,064 B2 | 12/2015 | Morero |
| 9,211,396 B2 | 12/2015 | Aboytes |
| 9,220,878 B2 | 12/2015 | Kajii |
| 9,238,124 B2 | 1/2016 | Grayzel et al. |
| 9,265,512 B2 | 2/2016 | Garrison et al. |
| 9,282,992 B2 | 3/2016 | Levine et al. |
| 9,289,546 B2 | 3/2016 | Erickson |
| 9,322,748 B1 | 4/2016 | Kimsey et al. |
| 9,339,282 B2 | 5/2016 | Green et al. |
| 9,345,508 B2 | 5/2016 | Hendrick |
| 9,345,856 B2 | 5/2016 | Witte |
| 9,345,858 B2 | 5/2016 | Flaherty et al. |
| 9,375,223 B2 | 6/2016 | Wallace |
| 9,398,946 B2 | 7/2016 | Valaie |
| 9,421,343 B2 | 8/2016 | Berthiaume et al. |
| 9,433,427 B2 | 9/2016 | Look et al. |
| 9,440,018 B2 | 9/2016 | Levin et al. |
| 9,446,216 B2 | 9/2016 | Olesky et al. |
| 9,480,813 B2 | 11/2016 | Fukuoka et al. |
| 9,504,805 B2 | 11/2016 | Vreeman |
| 9,510,854 B2 | 12/2016 | Mallaby |
| 9,539,022 B2 | 1/2017 | Bowman |
| 9,561,129 B2 | 2/2017 | Ross et al. |
| 9,592,372 B2 | 3/2017 | Myers |
| 9,616,172 B2 | 4/2017 | Ambrosina et al. |
| 9,616,195 B2 | 4/2017 | Lippert et al. |
| 9,616,213 B2 | 4/2017 | Furnish et al. |
| 9,662,137 B2 | 5/2017 | Jenson et al. |
| 9,707,380 B2 | 7/2017 | Qiu et al. |
| 9,724,491 B2 | 8/2017 | Solar et al. |
| 9,775,969 B2 | 10/2017 | Alvarez et al. |
| 9,801,643 B2 | 10/2017 | Hansen et al. |
| 9,808,277 B2 | 11/2017 | Nash et al. |
| 9,808,610 B2 | 11/2017 | Li et al. |
| 9,820,764 B2 | 11/2017 | Ulm, III |
| 9,826,998 B2 | 11/2017 | Ulm, III |
| 9,827,047 B2 | 11/2017 | Fudaba et al. |
| 9,833,593 B2 | 12/2017 | Kim et al. |
| 9,839,506 B2 | 12/2017 | Ulm, III |
| 9,848,882 B2 | 12/2017 | Lippert |
| 9,855,072 B2 | 1/2018 | Moberg et al. |
| 9,867,908 B2 | 1/2018 | Lareau et al. |
| 9,877,742 B2 | 1/2018 | Milner et al. |
| 9,878,076 B2 | 1/2018 | Gülcher et al. |
| 9,913,960 B2 | 3/2018 | Blanchard et al. |
| 9,931,129 B2 | 4/2018 | Walish et al. |
| 9,943,321 B2 | 4/2018 | Nita |
| 9,950,137 B2 | 4/2018 | Lippert et al. |
| 9,980,813 B2 | 5/2018 | Eller |
| 9,987,027 B2 | 6/2018 | Ben-Ami |
| 9,987,028 B2 | 6/2018 | Lowinger et al. |
| 10,010,698 B2 | 7/2018 | Watanabe et al. |
| 10,039,906 B2 | 8/2018 | Kume et al. |
| 10,086,169 B2 | 10/2018 | Grayzel et al. |
| 10,117,976 B2 | 11/2018 | Honda |
| 10,143,782 B2 | 12/2018 | Yurek et al. |
| 10,154,853 B2 | 12/2018 | To et al. |
| 10,179,224 B2 | 1/2019 | Yang et al. |
| 10,183,145 B2 | 1/2019 | Yang et al. |
| 10,183,146 B2 | 1/2019 | Yang et al. |
| 10,183,147 B2 | 1/2019 | Yang et al. |
| 10,183,151 B2 | 1/2019 | Alvarez et al. |
| 10,207,077 B2 | 2/2019 | Griggin et al. |
| 10,213,582 B2 | 2/2019 | Garrison et al. |
| 10,219,814 B2 | 3/2019 | Feltyberger et al. |
| 10,226,277 B2 | 3/2019 | Smith et al. |
| 10,238,833 B2 | 3/2019 | Christian et al. |
| 10,258,452 B2 | 4/2019 | Eckhouse et al. |
| 10,258,467 B2 | 4/2019 | Hou et al. |
| RE47,376 E | 5/2019 | Pokorney et al. |
| 10,278,678 B2 | 5/2019 | Peliks |
| 10,300,256 B2 | 5/2019 | Aboytes |
| 10,327,790 B2 | 6/2019 | Garrison et al. |
| 10,327,811 B2 | 6/2019 | Cannon et al. |
| 10,363,389 B2 | 7/2019 | Lippert et al. |
| 10,369,346 B2 | 8/2019 | Ryan et al. |
| 10,383,691 B2 | 8/2019 | Hendrick et al. |
| 10,383,751 B2 | 8/2019 | Ferrera et al. |
| 10,384,034 B2 | 8/2019 | Garrison et al. |
| 10,405,924 B2 | 9/2019 | Bowe |
| 10,441,745 B2 | 10/2019 | Yang et al. |
| 10,456,552 B2 | 10/2019 | Goyal |
| 10,456,557 B2 | 10/2019 | Guala et al. |
| 10,471,233 B2 | 11/2019 | Garrison et al. |
| 10,478,535 B2 | 11/2019 | Ogle |
| 10,499,944 B2 | 12/2019 | Mallaby |
| 10,531,883 B1 | 1/2020 | Deville et al. |
| 10,543,011 B2 | 1/2020 | Dormann |
| 10,569,049 B2 | 2/2020 | Garrison et al. |
| 10,603,467 B2 | 3/2020 | Alvarez et al. |
| 10,610,256 B2 | 4/2020 | Bowman |
| 10,646,239 B2 | 5/2020 | Garrison et al. |
| 10,653,434 B1 | 5/2020 | Yang et al. |
| 10,661,053 B2 | 5/2020 | Yang et al. |
| 10,668,192 B2 | 6/2020 | Raney et al. |
| 10,709,312 B2 | 7/2020 | Stigall et al. |
| 10,716,583 B2 | 7/2020 | Look et al. |
| 10,716,880 B2 | 7/2020 | Culbert et al. |
| 10,716,915 B2 | 7/2020 | Ogle et al. |
| 10,722,251 B2 | 7/2020 | Garrison et al. |
| 10,722,253 B2 | 7/2020 | Deville et al. |
| 10,722,683 B2 | 7/2020 | Solar et al. |
| 10,743,893 B2 | 8/2020 | Garrison et al. |
| 10,751,073 B2 | 8/2020 | Eckhouse et al. |
| 10,772,647 B2 | 9/2020 | Ben-Ami |
| 10,786,268 B2 | 9/2020 | Ben-Ami |
| 10,786,270 B2 | 9/2020 | Yang et al. |
| 10,792,402 B2 | 10/2020 | Heaton et al. |
| 10,799,265 B2 | 10/2020 | Graziani |
| 10,835,272 B2 | 11/2020 | Yang et al. |
| 10,835,278 B2 | 11/2020 | Wilke et al. |
| 10,835,711 B2 | 11/2020 | Yang et al. |
| 10,856,898 B2 | 12/2020 | Matsushita et al. |

(56) References Cited

U.S. PATENT DOCUMENTS

| | | |
|---|---|---|
| 10,864,351 B2 | 12/2020 | Garrison et al. |
| 10,874,423 B2 | 12/2020 | Tada et al. |
| 10,905,850 B2 | 2/2021 | Christian et al. |
| 10,918,834 B2 | 2/2021 | Sudin et al. |
| 10,959,750 B2 | 3/2021 | Wallace |
| 10,973,534 B2 | 4/2021 | Jeng |
| 10,980,555 B2 | 4/2021 | Panian |
| 10,980,968 B2 | 4/2021 | Christian et al. |
| 11,000,682 B2 | 5/2021 | Merritt et al. |
| 11,039,845 B2 | 6/2021 | Wallace |
| 11,065,018 B2 | 7/2021 | Buck et al. |
| 11,076,876 B2 | 8/2021 | Vale |
| 11,096,712 B2 | 8/2021 | Teigen et al. |
| 11,116,528 B2 | 9/2021 | Wallace et al. |
| 11,123,090 B2 | 9/2021 | Yang et al. |
| 11,135,049 B2 | 10/2021 | Gilson et al. |
| 11,147,949 B2 | 10/2021 | Yang et al. |
| 11,154,314 B2 | 10/2021 | Quick |
| 11,197,683 B1 | 12/2021 | Teigen et al. |
| 11,197,771 B2 | 12/2021 | Ferrera et al. |
| 11,207,096 B2 | 12/2021 | To et al. |
| 11,207,497 B1 | 12/2021 | Yee et al. |
| 11,224,457 B2 | 1/2022 | Brinkmann et al. |
| 11,234,723 B2 | 2/2022 | Ogle |
| 11,243,277 B2 | 2/2022 | Buck et al. |
| 11,253,292 B2 | 2/2022 | McGuckin, Jr. et al. |
| 11,259,821 B2 | 3/2022 | Buck et al. |
| 11,266,434 B2 | 3/2022 | McRae et al. |
| 11,305,048 B2 | 4/2022 | Kilcran et al. |
| 11,311,303 B2 | 4/2022 | Yang et al. |
| 11,318,282 B2 | 5/2022 | Garrison et al. |
| 11,337,712 B2 | 5/2022 | Teigen et al. |
| 11,364,043 B2 | 6/2022 | Wallace et al. |
| 11,395,665 B2 | 7/2022 | Yang et al. |
| 11,406,402 B2 | 8/2022 | Deville et al. |
| 11,413,054 B2 | 8/2022 | Ulm, III |
| 11,432,835 B2 | 9/2022 | Shaffer et al. |
| 11,439,799 B2 | 9/2022 | Buck et al. |
| 11,452,541 B2 | 9/2022 | Lippert et al. |
| 11,457,936 B2 | 10/2022 | Buck et al. |
| 11,464,528 B2 | 10/2022 | Brady et al. |
| 11,471,582 B2 | 10/2022 | Yee |
| 11,478,248 B2 | 10/2022 | Sultan et al. |
| 11,490,909 B2 | 11/2022 | Look et al. |
| 11,497,521 B2 | 11/2022 | Mallaby |
| 11,534,575 B2 | 11/2022 | Garrison et al. |
| 11,517,335 B2 | 12/2022 | Aboytes et al. |
| 11,547,426 B2 | 1/2023 | Deville et al. |
| 11,553,935 B2 | 1/2023 | Buck et al. |
| 11,554,005 B2 | 1/2023 | Merritt et al. |
| 11,559,382 B2 | 1/2023 | Merritt et al. |
| 11,565,082 B2 | 1/2023 | Yourgenlow |
| 11,617,865 B2 | 4/2023 | Ogle |
| 11,633,272 B2 | 4/2023 | Buck et al. |
| 11,633,570 B2 | 4/2023 | Garrison et al. |
| 11,638,637 B2 | 6/2023 | Buck et al. |
| 11,672,561 B2 | 6/2023 | Look et al. |
| 11,678,905 B2 | 6/2023 | Look et al. |
| 11,696,780 B2 | 7/2023 | Brehm et al. |
| 11,697,011 B2 | 7/2023 | Merritt et al. |
| 11,697,012 B2 | 7/2023 | Merritt et al. |
| 11,744,691 B2 | 7/2023 | Merritt et al. |
| 11,759,219 B2 | 9/2023 | Teigen et al. |
| 11,766,539 B2 | 9/2023 | Yee et al. |
| 11,771,867 B2 | 10/2023 | Ogle |
| 11,819,228 B2 | 11/2023 | Buck et al. |
| 11,844,921 B2 | 12/2023 | Merritt et al. |
| 11,849,963 B2 | 12/2023 | Quick |
| 11,850,349 B2 | 12/2023 | Yee |
| 11,865,291 B2 | 1/2024 | Merritt et al. |
| 11,878,108 B2 | 1/2024 | Cotton et al. |
| 11,890,180 B2 | 2/2024 | Merritt et al. |
| 11,918,765 B2 | 3/2024 | Horst et al. |
| 11,951,267 B2 | 4/2024 | Lippert et al. |
| 11,969,333 B2 | 4/2024 | Merritt et al. |
| 11,974,910 B2 | 5/2024 | Merritt et al. |
| 12,042,160 B2 | 7/2024 | Yang et al. |
| 2001/0031980 A1 | 10/2001 | Wensel et al. |
| 2001/0049486 A1 | 12/2001 | Evans et al. |
| 2002/0016565 A1 | 2/2002 | Zadno-Azizi et al. |
| 2002/0026145 A1 | 2/2002 | Bagaoisan et al. |
| 2002/0091372 A1 | 7/2002 | Cragg et al. |
| 2002/0156459 A1 | 10/2002 | Ye et al. |
| 2002/0169467 A1 | 11/2002 | Heitzmann et al. |
| 2002/0173812 A1 | 11/2002 | McGuckin et al. |
| 2002/0177800 A1 | 11/2002 | Bagaoisan et al. |
| 2002/0177899 A1 | 11/2002 | Eum et al. |
| 2003/0071285 A1 | 4/2003 | Tsukernik |
| 2003/0116731 A1 | 6/2003 | Hartley |
| 2003/0135193 A1 | 7/2003 | Hilgers et al. |
| 2003/0135198 A1 | 7/2003 | Berhow et al. |
| 2003/0153847 A1 | 8/2003 | Sandler et al. |
| 2003/0153874 A1 | 8/2003 | Tal |
| 2003/0195467 A1 | 10/2003 | Mickley |
| 2003/0212384 A1 | 11/2003 | Hayden |
| 2003/0225336 A1 | 12/2003 | Callister et al. |
| 2003/0225379 A1 | 12/2003 | Schaffer et al. |
| 2004/0006306 A1 | 1/2004 | Evans et al. |
| 2004/0019322 A1 | 1/2004 | Hoffmann |
| 2004/0059290 A1 | 3/2004 | Palasis |
| 2004/0138693 A1 | 7/2004 | Eskuri et al. |
| 2004/0153049 A1 | 8/2004 | Hewitt et al. |
| 2004/0172008 A1 | 9/2004 | Layer |
| 2004/0243102 A1 | 12/2004 | Berg et al. |
| 2005/0004534 A1 | 1/2005 | Lockwood et al. |
| 2005/0021002 A1 | 1/2005 | Deckman et al. |
| 2005/0049574 A1 | 3/2005 | Petrick et al. |
| 2005/0080400 A1 | 4/2005 | Corcoran et al. |
| 2005/0103332 A1 | 5/2005 | Gingles et al. |
| 2005/0124985 A1 | 6/2005 | Takayama et al. |
| 2005/0182386 A1 | 8/2005 | Aggerholm |
| 2005/0187570 A1 | 8/2005 | Nguyen et al. |
| 2005/0283165 A1 | 12/2005 | Gadberry |
| 2006/0030835 A1 | 2/2006 | Sherman et al. |
| 2006/0064036 A1 | 3/2006 | Osborne et al. |
| 2006/0074401 A1 | 4/2006 | Ross |
| 2006/0089618 A1 | 4/2006 | McFerran et al. |
| 2006/0095062 A1 | 5/2006 | Stephens |
| 2006/0111649 A1 | 5/2006 | Zhou |
| 2006/0124212 A1 | 6/2006 | Zhou |
| 2006/0184108 A1 | 8/2006 | Honebrink |
| 2006/0217664 A1 | 9/2006 | Hattler et al. |
| 2006/0224106 A1 | 10/2006 | Honchel |
| 2006/0247755 A1 | 11/2006 | Pal et al. |
| 2007/0016132 A1 | 1/2007 | Oepen et al. |
| 2007/0038225 A1 | 2/2007 | Osborne et al. |
| 2007/0043333 A1 | 2/2007 | Kampa et al. |
| 2007/0185521 A1 | 8/2007 | Bui et al. |
| 2007/0197956 A1 | 8/2007 | Le et al. |
| 2008/0058764 A1 | 3/2008 | Majercak et al. |
| 2008/0064984 A1 | 3/2008 | Pflueger et al. |
| 2008/0086051 A1 | 4/2008 | Voegele |
| 2008/0097251 A1 | 4/2008 | Babaev et al. |
| 2008/0154186 A1 | 6/2008 | Appling et al. |
| 2008/0167621 A1 | 7/2008 | Wagner et al. |
| 2008/0179344 A1 | 7/2008 | Michaels et al. |
| 2008/0188928 A1 | 8/2008 | Salahieh et al. |
| 2008/0234715 A1 | 9/2008 | Pesce |
| 2008/0262471 A1 | 10/2008 | Warnock |
| 2008/0300493 A1 | 12/2008 | Gatto et al. |
| 2008/0312639 A1 | 12/2008 | Weber |
| 2009/0030400 A1 | 1/2009 | Bose et al. |
| 2009/0157051 A1 | 6/2009 | Appling et al. |
| 2009/0182370 A1 | 7/2009 | Volobuyev et al. |
| 2009/0187143 A1 | 7/2009 | Vreeman |
| 2009/0216205 A1 | 8/2009 | Marshall et al. |
| 2009/0234321 A1 | 9/2009 | Shapland et al. |
| 2009/0270800 A1 | 10/2009 | Spurchise et al. |
| 2009/0270888 A1 | 10/2009 | Patel et al. |
| 2009/0287190 A1 | 11/2009 | Shippert |
| 2009/0312786 A1 | 12/2009 | Trask et al. |
| 2010/0023033 A1 | 1/2010 | Mauch et al. |
| 2010/0030256 A1 | 2/2010 | Dubrul et al. |
| 2010/0042118 A1 | 2/2010 | Garrison et al. |

(56) References Cited

U.S. PATENT DOCUMENTS

| | | |
|---|---|---|
| 2010/0049168 A1 | 2/2010 | Parker et al. |
| 2010/0057051 A1 | 3/2010 | Howat et al. |
| 2010/0063413 A1 | 3/2010 | Volz |
| 2010/0114017 A1 | 5/2010 | Lenker et al. |
| 2010/0125253 A1 | 5/2010 | Olson et al. |
| 2010/0204712 A1 | 8/2010 | Mallaby |
| 2010/0217235 A1 | 8/2010 | Thorstenson et al. |
| 2010/0256603 A1 | 10/2010 | Lippert et al. |
| 2010/0256604 A1 | 10/2010 | Lippert et al. |
| 2010/0312141 A1 | 12/2010 | Keast et al. |
| 2011/0034986 A1 | 2/2011 | Chou |
| 2011/0077620 A1 | 3/2011 | deBeer |
| 2011/0112567 A1 | 5/2011 | Lenker et al. |
| 2011/0137399 A1 | 6/2011 | Chomas et al. |
| 2011/0144592 A1 | 6/2011 | Wong et al. |
| 2011/0213290 A1* | 9/2011 | Chin ............... A61B 17/22 604/151 |
| 2011/0238041 A1 | 9/2011 | Lim et al. |
| 2012/0041474 A1 | 2/2012 | Eckhouse |
| 2012/0123327 A1 | 5/2012 | Miller |
| 2012/0179032 A1 | 7/2012 | Bromander et al. |
| 2012/0232326 A1 | 9/2012 | Habib |
| 2012/0277845 A1 | 11/2012 | Bowe |
| 2013/0012924 A1 | 1/2013 | Davis et al. |
| 2013/0018318 A1 | 1/2013 | Ravichandran et al. |
| 2013/0018359 A1 | 1/2013 | Coyle |
| 2013/0030461 A1 | 1/2013 | Marks et al. |
| 2013/0035628 A1 | 2/2013 | Garrison et al. |
| 2013/0046285 A1 | 2/2013 | Griffin et al. |
| 2013/0096551 A1 | 4/2013 | Govari et al. |
| 2013/0116701 A1 | 5/2013 | Wang et al. |
| 2013/0131499 A1 | 5/2013 | Chan et al. |
| 2013/0131641 A1 | 5/2013 | Jimenez et al. |
| 2013/0144328 A1 | 6/2013 | Weber et al. |
| 2013/0158511 A1 | 6/2013 | Aggerholm et al. |
| 2013/0172851 A1 | 7/2013 | Shimada et al. |
| 2013/0218073 A1 | 8/2013 | Ekdahl et al. |
| 2013/0245430 A1 | 9/2013 | Selmon et al. |
| 2014/0039461 A1 | 2/2014 | Anderson et al. |
| 2014/0046243 A1 | 2/2014 | Ray et al. |
| 2014/0046244 A1 | 2/2014 | Ray et al. |
| 2014/0074144 A1 | 3/2014 | Shrivastava et al. |
| 2014/0100531 A1 | 4/2014 | Ankrum et al. |
| 2014/0114287 A1 | 4/2014 | Beasley et al. |
| 2014/0128848 A1 | 5/2014 | Appling et al. |
| 2014/0163367 A1 | 6/2014 | Eskuri |
| 2014/0200608 A1 | 7/2014 | Brady et al. |
| 2014/0249508 A1 | 9/2014 | Wang et al. |
| 2014/0276470 A1 | 9/2014 | Lareau et al. |
| 2014/0276618 A1 | 9/2014 | Di Caprio et al. |
| 2014/0296868 A1 | 10/2014 | Garrison et al. |
| 2014/0296889 A1 | 10/2014 | Avneri et al. |
| 2014/0309533 A1 | 10/2014 | Yamashita et al. |
| 2014/0330286 A1 | 11/2014 | Wallace |
| 2014/0343537 A1 | 11/2014 | Eversull et al. |
| 2014/0350645 A1 | 11/2014 | Diller et al. |
| 2014/0358123 A1 | 12/2014 | Ueda |
| 2014/0371718 A1 | 12/2014 | Alvarez et al. |
| 2014/0379023 A1 | 12/2014 | Brady et al. |
| 2015/0025562 A1 | 1/2015 | Dinh et al. |
| 2015/0046148 A1 | 2/2015 | Oh et al. |
| 2015/0119859 A1 | 4/2015 | Cajamarca et al. |
| 2015/0133978 A1 | 5/2015 | Paul, Jr. |
| 2015/0157772 A1 | 6/2015 | Li et al. |
| 2015/0173782 A1 | 6/2015 | Garrison et al. |
| 2015/0174363 A1 | 6/2015 | Sutermeister et al. |
| 2015/0174368 A1 | 6/2015 | Garrison et al. |
| 2015/0269825 A1 | 9/2015 | Tran |
| 2015/0290390 A1 | 10/2015 | Ring et al. |
| 2015/0335857 A1 | 11/2015 | Ishikawa |
| 2015/0352325 A1 | 12/2015 | Quick |
| 2015/0359547 A1 | 12/2015 | Vale et al. |
| 2016/0000443 A1 | 1/2016 | Lilburn et al. |
| 2016/0030079 A1 | 2/2016 | Cohen |
| 2016/0051386 A1 | 2/2016 | Haarmann-Theimann |
| 2016/0058513 A1 | 3/2016 | Giorgi |
| 2016/0135829 A1 | 5/2016 | Holochwost et al. |
| 2016/0166265 A1 | 6/2016 | Nita |
| 2016/0213396 A1 | 7/2016 | Dowell et al. |
| 2016/0220741 A1 | 8/2016 | Garrison et al. |
| 2016/0346508 A1 | 12/2016 | Williams et al. |
| 2016/0346515 A1 | 12/2016 | Buller |
| 2016/0354532 A1 | 12/2016 | Olesky et al. |
| 2017/0000576 A1 | 1/2017 | Zirps |
| 2017/0007277 A1 | 1/2017 | Drapeau et al. |
| 2017/0020540 A1 | 1/2017 | Chou et al. |
| 2017/0035444 A1 | 2/2017 | Garrison et al. |
| 2017/0043124 A1 | 2/2017 | Vreeman |
| 2017/0072163 A1 | 3/2017 | Lim et al. |
| 2017/0072165 A1 | 3/2017 | Lim et al. |
| 2017/0100142 A1 | 4/2017 | Look et al. |
| 2017/0105743 A1 | 4/2017 | Vale et al. |
| 2017/0143416 A1 | 5/2017 | Guler et al. |
| 2017/0181835 A1 | 6/2017 | Kleshinski et al. |
| 2017/0252057 A1 | 9/2017 | Bonnette et al. |
| 2017/0259037 A1 | 9/2017 | Kern et al. |
| 2017/0333000 A1 | 11/2017 | Nystrom et al. |
| 2017/0340867 A1 | 11/2017 | Accisano |
| 2018/0015254 A1 | 1/2018 | Cragg et al. |
| 2018/0050135 A1 | 2/2018 | Reinboth |
| 2018/0207397 A1 | 7/2018 | Look et al. |
| 2018/0207412 A1 | 7/2018 | Malek et al. |
| 2018/0228502 A1 | 8/2018 | Shaffer et al. |
| 2018/0242962 A1 | 8/2018 | Walen et al. |
| 2018/0242989 A1 | 8/2018 | Nita |
| 2018/0242999 A1 | 8/2018 | Thatipelli |
| 2018/0256860 A1 | 9/2018 | Lippert et al. |
| 2018/0263642 A1 | 9/2018 | Nita |
| 2018/0280079 A1 | 10/2018 | Bazilian |
| 2018/0289925 A1 | 10/2018 | Palmer et al. |
| 2018/0296233 A1 | 10/2018 | Schwager |
| 2018/0296236 A1 | 10/2018 | Goldfarb et al. |
| 2018/0304040 A1 | 10/2018 | Jalgaonkar |
| 2018/0338770 A1 | 11/2018 | Mogi et al. |
| 2018/0353194 A1 | 12/2018 | Shaffer et al. |
| 2019/0022363 A1 | 1/2019 | Grayzel et al. |
| 2019/0070387 A1 | 3/2019 | Goyal |
| 2019/0105477 A1 | 4/2019 | Heilman et al. |
| 2019/0105478 A1 | 4/2019 | Malek et al. |
| 2019/0108540 A1 | 4/2019 | Look et al. |
| 2019/0183517 A1 | 6/2019 | Ogle |
| 2019/0269368 A1 | 9/2019 | Hauck et al. |
| 2019/0275290 A1 | 9/2019 | Yamashita et al. |
| 2019/0290884 A1 | 9/2019 | Kanemasa et al. |
| 2019/0329003 A1 | 10/2019 | Watanabe |
| 2019/0336142 A1 | 11/2019 | Torrie |
| 2019/0351182 A1 | 11/2019 | Chou et al. |
| 2019/0381221 A1 | 12/2019 | Ogle |
| 2019/0381223 A1 | 12/2019 | Culbert et al. |
| 2020/0009350 A1 | 1/2020 | Goyal |
| 2020/0015840 A1 | 1/2020 | Mallaby |
| 2020/0022712 A1 | 1/2020 | Deville et al. |
| 2020/0023160 A1 | 1/2020 | Chou et al. |
| 2020/0046368 A1 | 2/2020 | Merritt et al. |
| 2020/0094027 A1 | 3/2020 | Davis |
| 2020/0171276 A1 | 6/2020 | Onozuka |
| 2020/0171277 A1 | 6/2020 | Garrison et al. |
| 2020/0179576 A1 | 6/2020 | Wood |
| 2020/0188630 A1 | 6/2020 | Fujita et al. |
| 2020/0205845 A1 | 7/2020 | Yang et al. |
| 2020/0222672 A1 | 7/2020 | Davis et al. |
| 2020/0269014 A1 | 8/2020 | Rottenberg et al. |
| 2020/0276411 A1 | 9/2020 | Ogle et al. |
| 2020/0289136 A1 | 9/2020 | Chou |
| 2020/0337716 A1 | 10/2020 | Garrison et al. |
| 2020/0345904 A1 | 11/2020 | Casey et al. |
| 2020/0345975 A1 | 11/2020 | Snyder |
| 2020/0345979 A1 | 11/2020 | Loh et al. |
| 2020/0352494 A1 | 11/2020 | Gable et al. |
| 2020/0368494 A1 | 11/2020 | Parmar |
| 2020/0397957 A1 | 12/2020 | Teigen et al. |
| 2021/0008351 A1 | 1/2021 | Snyder et al. |
| 2021/0045622 A1 | 2/2021 | Petroff et al. |
| 2021/0045758 A1 | 2/2021 | Garrison et al. |

(56) References Cited

U.S. PATENT DOCUMENTS

| | | |
|---|---|---|
| 2021/0052296 A1 | 2/2021 | Garrison |
| 2021/0069467 A1 | 3/2021 | Garrison et al. |
| 2021/0106792 A1 | 4/2021 | Rafiee |
| 2021/0128182 A1 | 5/2021 | Teigen et al. |
| 2021/0128883 A1 | 5/2021 | Gill et al. |
| 2021/0146094 A1 | 5/2021 | Christian et al. |
| 2021/0162184 A1 | 6/2021 | Lippert et al. |
| 2021/0186537 A1 | 6/2021 | Buck et al. |
| 2021/0187176 A1 | 6/2021 | Zambianchi et al. |
| 2021/0213241 A1 | 7/2021 | Christian et al. |
| 2021/0228845 A1 | 7/2021 | Lippert et al. |
| 2021/0283371 A1 | 9/2021 | Guimaraes et al. |
| 2021/0315598 A1 | 10/2021 | Buck et al. |
| 2021/0316127 A1 | 10/2021 | Buck et al. |
| 2021/0346656 A1 | 11/2021 | Lippert et al. |
| 2021/0353314 A1 | 11/2021 | Porter et al. |
| 2021/0361366 A1 | 11/2021 | Murphy et al. |
| 2022/0047849 A1 | 2/2022 | Yee et al. |
| 2022/0096104 A1 | 3/2022 | Ogle |
| 2022/0105312 A1 | 4/2022 | Davis |
| 2022/0105314 A1 | 4/2022 | Horst et al. |
| 2022/0105318 A1 | 4/2022 | Davis et al. |
| 2022/0118225 A1 | 4/2022 | Snyder et al. |
| 2022/0151646 A1 | 5/2022 | Dholakia et al. |
| 2022/0218365 A1 | 7/2022 | Deville et al. |
| 2022/0218366 A1 | 7/2022 | Deville et al. |
| 2022/0226550 A1 | 7/2022 | Zambianchi et al. |
| 2022/0240959 A1 | 8/2022 | Quick |
| 2022/0241485 A1 | 8/2022 | Nakagawa et al. |
| 2022/0280147 A1 | 9/2022 | Davis et al. |
| 2022/0280753 A1 | 9/2022 | Garrison et al. |
| 2022/0296850 A1 | 9/2022 | Lippert et al. |
| 2022/0305189 A1 | 9/2022 | Chavan et al. |
| 2022/0346814 A1 | 11/2022 | Quick |
| 2022/0361901 A1 | 11/2022 | De Leon et al. |
| 2023/0015259 A1 | 1/2023 | Buck et al. |
| 2023/0061728 A1 | 3/2023 | Davis et al. |
| 2023/0064188 A1 | 3/2023 | Davis et al. |
| 2023/0069826 A1 | 3/2023 | Keating et al. |
| 2023/0074586 A1 | 3/2023 | Verri et al. |
| 2023/0082226 A1 | 3/2023 | Lippert et al. |
| 2023/0093602 A1 | 3/2023 | Higgins et al. |
| 2023/0165596 A1 | 6/2023 | Aboytes et al. |
| 2023/0211122 A1 | 7/2023 | Luna et al. |
| 2023/0226318 A1 | 7/2023 | Yourgenlow |
| 2023/0248498 A1 | 8/2023 | Buck et al. |
| 2023/0248499 A1 | 8/2023 | Buck et al. |
| 2023/0248500 A1 | 8/2023 | Buck et al. |
| 2023/0248501 A1 | 8/2023 | Buck et al. |
| 2023/0248502 A1 | 8/2023 | Buck et al. |
| 2023/0248503 A1 | 8/2023 | Buck et al. |
| 2023/0248504 A1 | 8/2023 | Buck et al. |
| 2023/0355371 A1 | 11/2023 | Buck et al. |
| 2024/0016505 A1 | 1/2024 | Horowitz et al. |
| 2024/0100299 A1 | 3/2024 | Schabert |
| 2024/0173042 A1 | 5/2024 | Yang et al. |
| 2024/0197978 A1 | 6/2024 | Yee |

FOREIGN PATENT DOCUMENTS

| | | |
|---|---|---|
| CN | 101252958 A | 8/2008 |
| CN | 101321552 A | 12/2008 |
| CN | 101340849 A | 1/2009 |
| CN | 101795631 A | 8/2010 |
| CN | 201596219 U | 10/2010 |
| CN | 102159146 | 8/2011 |
| CN | 102205161 | 10/2011 |
| CN | 102319097 A | 1/2012 |
| CN | 102844071 A | 12/2012 |
| CN | 102847220 A | 1/2013 |
| CN | 203263993 U | 11/2013 |
| CN | 103648574 A | 3/2014 |
| CN | 103764214 A | 4/2014 |
| CN | 204158457 U | 2/2015 |
| CN | 104548316 A | 4/2015 |
| CN | 104622538 A | 5/2015 |
| CN | 104884117 | 9/2015 |
| CN | 104918578 | 9/2015 |
| CN | 105120776 A | 12/2015 |
| CN | 105208945 | 12/2015 |
| CN | 105208951 A | 12/2015 |
| CN | 204909516 U | 12/2015 |
| CN | 107405159 A | 11/2017 |
| CN | 107441615 | 12/2017 |
| CN | 107614048 | 1/2018 |
| CN | 110548209 | 12/2019 |
| CN | 110652645 | 1/2020 |
| CN | 110916768 | 3/2020 |
| CN | 113797424 | 12/2021 |
| DE | 8900059 | 5/1989 |
| DE | 202005007570 | 9/2005 |
| DE | 102017004383 | 7/2018 |
| EP | 0 150 666 | 8/1985 |
| EP | 0 330 843 | 12/1993 |
| EP | 0 582 533 | 2/1994 |
| EP | 0 309 471 | 8/1996 |
| EP | 0 937 481 | 8/1999 |
| EP | 1 349 486 | 3/2008 |
| EP | 2 937 108 | 10/2015 |
| EP | 2 211 732 | 5/2018 |
| EP | 3 698 740 | 8/2020 |
| EP | 3 534 838 | 1/2021 |
| GB | 2042128 | 9/1980 |
| JP | 2002-535049 | 10/2002 |
| JP | 2006-087643 | 4/2006 |
| JP | 2006-102222 | 4/2006 |
| JP | 2013-504388 | 2/2013 |
| JP | 5953461 | 7/2016 |
| JP | 2017-042222 | 3/2017 |
| WO | WO 95/009659 | 4/1995 |
| WO | WO 2000/000100 | 1/2000 |
| WO | WO 2002/065897 | 8/2002 |
| WO | WO 2004/008974 | 1/2004 |
| WO | WO 2004/009171 | 1/2004 |
| WO | WO 2006/101170 | 9/2006 |
| WO | WO 2006/124307 | 11/2006 |
| WO | WO 2009/054968 | 4/2009 |
| WO | WO 2009/125575 | 10/2009 |
| WO | WO 2009/132218 | 10/2009 |
| WO | WO 2010/048649 | 5/2010 |
| WO | WO 2011/011493 | 1/2011 |
| WO | WO 2012/052159 | 4/2012 |
| WO | WO 2014/151209 | 9/2014 |
| WO | WO 2016/001712 | 1/2016 |
| WO | WO 2016/018781 | 2/2016 |
| WO | WO-2016126974 A1 * | 8/2016 ............ A61B 17/22 |
| WO | WO 2017/147493 | 8/2017 |
| WO | WO 2018/019829 | 2/2018 |
| WO | WO 2018/169032 | 9/2018 |
| WO | WO 2019/115809 | 6/2019 |
| WO | WO 2019/178165 | 9/2019 |
| WO | WO 2019/213179 | 11/2019 |
| WO | WO 2019/222518 | 11/2019 |
| WO | WO 2019/246583 | 12/2019 |
| WO | WO 2020/145928 | 7/2020 |
| WO | WO 2021/016213 | 1/2021 |
| WO | WO 2021/064955 | 4/2021 |
| WO | WO 2021/090821 | 5/2021 |
| WO | WO 2021/105658 | 6/2021 |
| WO | WO 2023/159063 | 8/2023 |
| WO | WO 2023/248224 | 12/2023 |

OTHER PUBLICATIONS

Arko et al., Jul. 2019, Mechanical Power Aspiration with the Indigo® System: Rethinking Clot Removal, Insert to Endovascular Today, 18(7):33-40.
Bose et al., Aug. 2008, The Penumbra System: A Mechanical Device for the Treatment of Acute Stroke due to Thromboembolism, AJNR Am J Neuroradiol, 29:1409-1413.
Boston Scientific, 2015, Angiojet™ Thrombectomy System, Clears Thrombus. Right, from the start., product brochure, 24 pp.

(56) References Cited

OTHER PUBLICATIONS

Boston Scientific, 2015, Angiojet™ Ultra Thrombectomy System, Power Pulse™ Delivery, product brochure, 2 pp.
Crowner et al., Sep. 2019, Percutaneous thrombectomy using a novel single-session device for acute ilio-caval deep vein thrombosis, Journal of Vascular Surgery Cases and Innovative Techniques, 5(3):302-304.
Dennis et al., eds., 1895, System of Surgery v. 2, Lea Brothers & Co., Philadelphia, pp. 96-97, 919-926.
Dopheide et al., Jan. 2018, Early clinical outcomes of a novel rheolytic directional thrombectomy technique for patients with iliofemoral deep vein thrombosis, VASA, 47(1):56-62.
Dragstedt et al., 2013, Utility of thrombectomy in primary percutaneous coronary intervention, Intervent Cardiol Clin, 2:361-374.
Engelberger et al., Nov. 8, 2011, Catheter-Based Reperfusion Treatment of Pulmonary Embolism, Circulation, 124(19):2139-2144.
Invatec, Diver C.E. Max, product brochure, downloaded Dec. 18, 2023 from htps:www.acar.cz/img/kardio/invatec/diver.pdf, 2 pp.
Medtronic, 2013, Export™ Aspiration Catheter, instructions for use, 8 pp.
Nikoubashman et al., 2018, Under pressure: comparison of aspiration techniques for endovascular mechanical thrombectomy, Am J Neuroradiol, 39(5):905-909.
Park, Mar. 2015, A Suction Thrombectomy Technique: A Rapid and Effective Method for Intra-Arterial Thrombolysis, Journal of Cerebrovascular and Endovascular Neurosurgery, 17(1):13-19.
Schaerf et al., Oct.-Nov. 2016, Percutaneous Vacuum-Assisted Thrombectomy Device Usedfor Removal of Large Vegetations on Infected Pacemaker and Defibrillator Leads as an Adjunct to Lead Extraction, Journal of Atrial Fibrillation, 9(3):15-17.
Shidham et al., Sep. 29, 2009, Preparation and Using Phantom Lesions to Practice Fine Needle Aspiration Biopsies, Journal of Visualized Experiments, 31(e1404)1-7.
Silk Road Medical Inc., Jan. 2017, Instructions for Use: ENROUTE® Transcarotid Neuroprotection System (NPS), 20 pp.
Taleb et al., 2014, Review of current technologies for thromboembolism management, Minerva Cardioangiol, 62:343-357.
UCLAhealth.org, Spring 2014, Vacuum Device Offers Alternative to Surgery for Patients with Potentially Deadly Clots, 62:1-2.
Vascular Access, 2013, Occlusion Management Guideline for Central Venous Access Devices (CVADs), Journal of the Canadian Vascular Access Association, 7(Supplement 1):1-36.
Apollo Irrigation Tubing Product Label, Dec. 15, 2014, Trademark Snap Shot.
AXS Universal, Jun. 2017, Aspiration Set product brochure, 2 pp.
Behrens et al., Dec. 2015, Venous Thromboembolic Disease: The Use of the Aspiration Thrombectomy Device AngioVac, Seminars in Interventional Radiology, 32(4):374/378.
ClotTriever USPTO Trademark Specimen, Apr. 20, 2017, 1 p.
ClotTriever USPTO Trademark Status, Feb. 25, 2017, 3 pp.
ClotTriever USPTO Trademark/Service Mark Statement of Use, Feb. 25, 2017, 8 pp.
Donaldson et al., Aug. 2015, Thrombectomy Using Suction Filtration and Veno/venous Bypass: Single Center Experience with a Novel Device, Catheterization and Cardiovascular Interventions, 86:E81/E87.
FlowTriever USPTO Statement of Use, Mar. 6, 2015.
FlowTriever USPTO Trademark Specimen, Apr. 21, 2015, 1 p.
FlowTriever USPTO Trademark Status, Mar. 6, 2015, 3 pp.
Fojtik et al., May/Jun. 2013, Cardiovascular Innovations: Novel mechanical aspiration system to improve thrombus aspiration speed, force, and control, Cardiovascular Revascularization Medicine, 3:160-163.
Froehler, May 18, 2018, Comparison of Vacuum Pressures and Forces Generated by Different Catheters and Pumps for Aspiration Thrombectomy in Acute Ischemic Stroke, Interventional Neurology, 6(3/4):199-206.
Inari Medical, May 20, 2019, A Venous Solution, FlowTriever® product brochure, https://web.archive.org/web/20190520001027/ https:/www.inarimedical.com/, 7 pp.
Kohi et al., 2016, Catheter directed interventions for acute deep vein thrombosis, Cardiovasc Diagn Ther, 6(6):599-611.
Michelson et al., 2017, Use of a Modified Cardiopulmonary Bypass Circuit for Suction Embolectomy with the AngioVac Device, J Extra Corpor Technol., 49:299-303.
Moriarty et al., Oct. 2016, Removal of Caval and Right Atrial Thrombi and Masses Using the AngioVac Device: Initial Operative Experience, J Vasc Interv Radiol, 27:1584-1591.
Ojeda, Dec. 27, 2018, Breakthrough blood clot treatment, screenshot of YouTube video, https://www.youtube.com/watch?v=niRpRNy7Pvl&t=76s, 1p.
Pasha et al., Jun. 2014, Successful management of acute massive pulmonary embolism using Angiovac suction catheter technique in a hemodynamically unstable patient, Cardiovascular Revascularization Medicine, 15:240-243.
Resnick et al., May 2016, Single/Center Experience Using AngioVac with Extracorporeal Bypass for Mechanical Thrombectomy of Atrial and Central Vein Thrombi, J Vasc Interv Radiol., 27:723-729.
Salsamendi et al., Aug. 2015, Single Center Experience with the AngioVac Aspiration System, Cardiovasc Intervent Radiol, 38:998-1004.
Silver et al., Jul. 2018, Acute DVT: are we overtreating or undertreating? Endovascular today, 17(7):84-87.
Smith et al., Mar. 2014, Vacuum/Assisted Thrombectomy Device (AngioVac) in the Management of Symptomatic Iliocaval Thrombosis, J Vasc Interv Radiol, 25:425-430.
Soverow et al., Apr. 2016, Acute Myocardial Infarction/Thrombectomy, Interventional Cardiology Clinics, 5(2):P259-269.
UreSil® Global Product Catalog CT, Interventional Radiology, Ultrasound and Emergency Department, Jan. 2, 2019, 24 pp.
US Securities and Exchange Commission Annual Report for the 2015 Fiscal Year Penumbra, Inc., Mar. 8, 2016, 290 pp.
Weisberg, May 14, 2019, St. Peter's Hospital First in Upstate New York to Perform New, Minimally Invasive Treatment for Blood Clots, St. Peter's News, 3 pp.

* cited by examiner

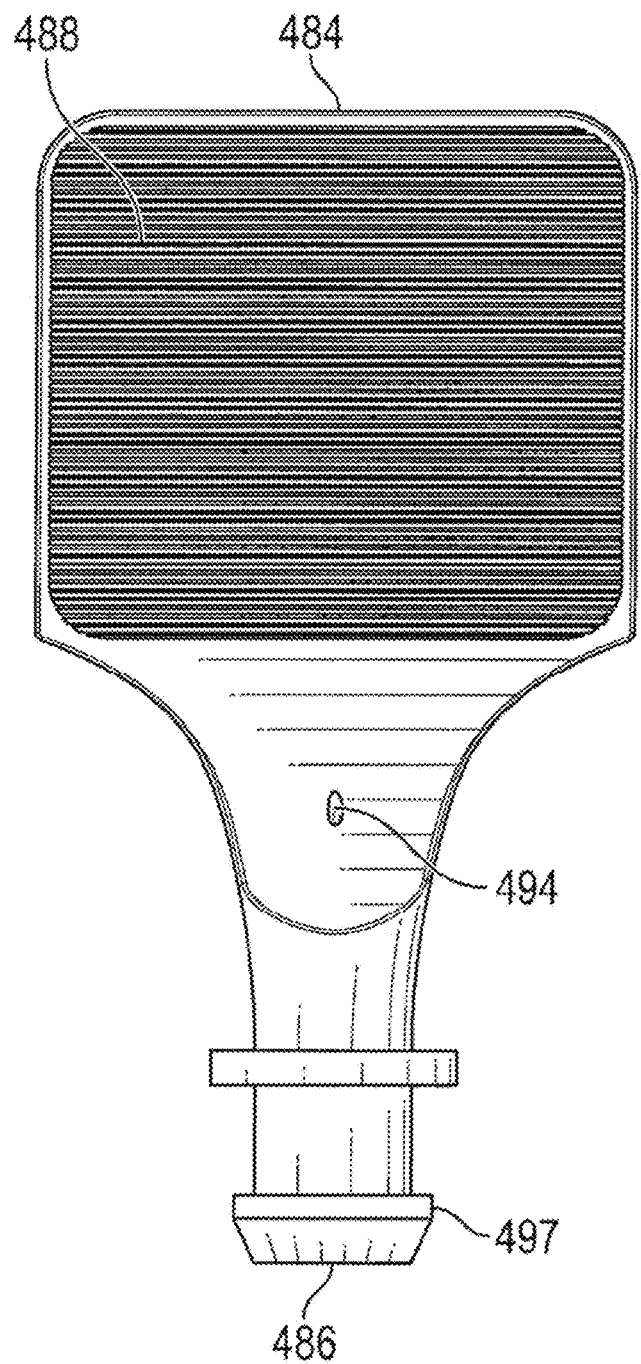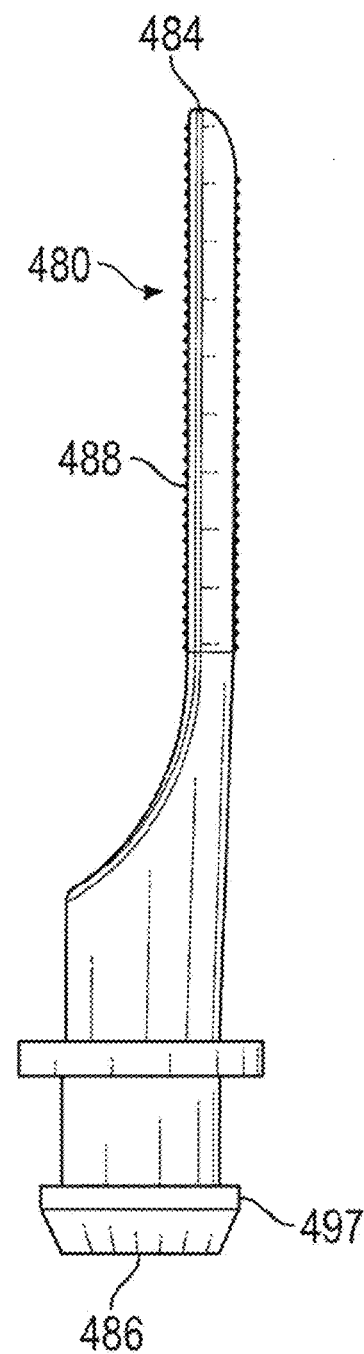
FIG. 11B  FIG. 11C

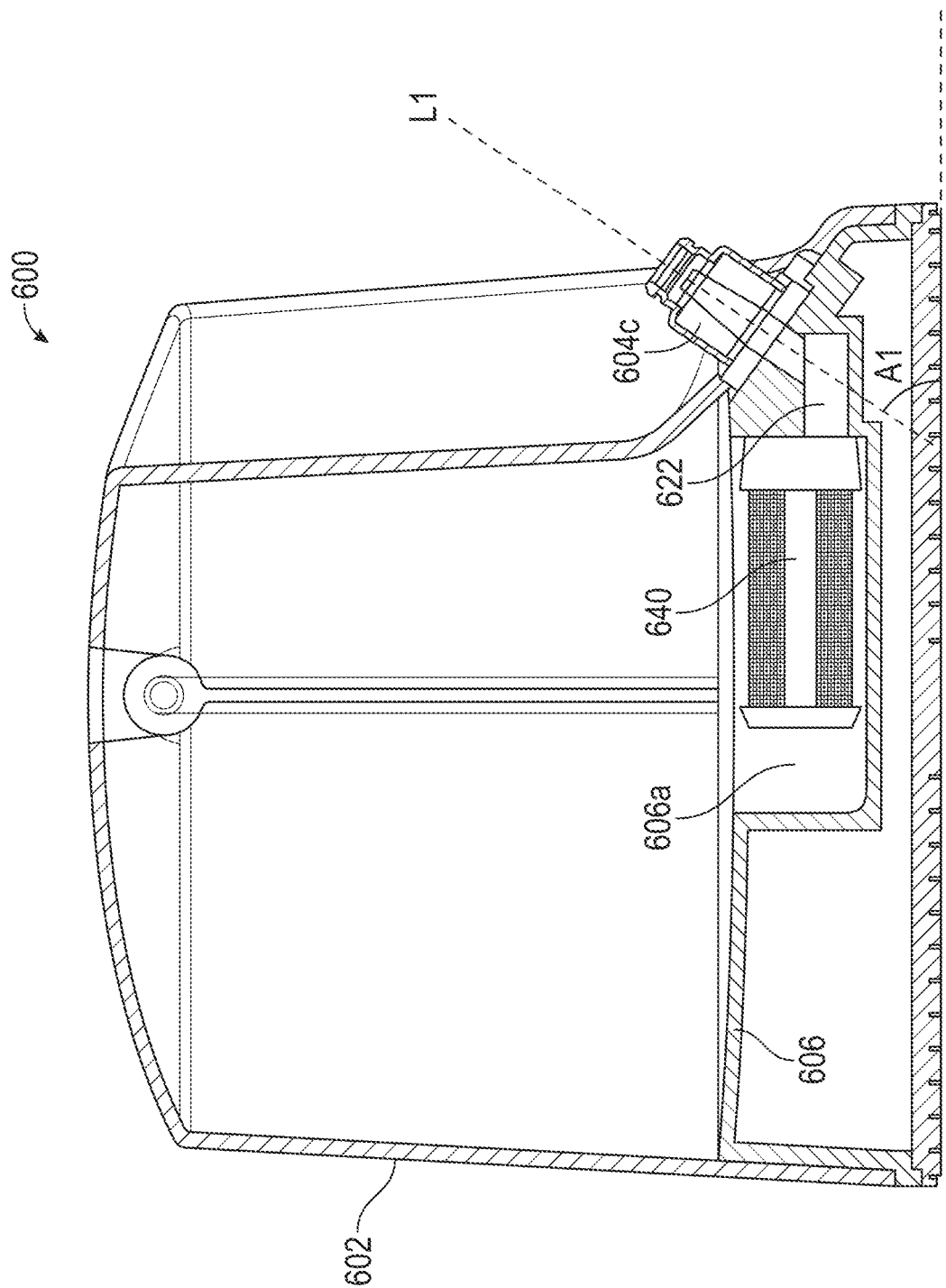

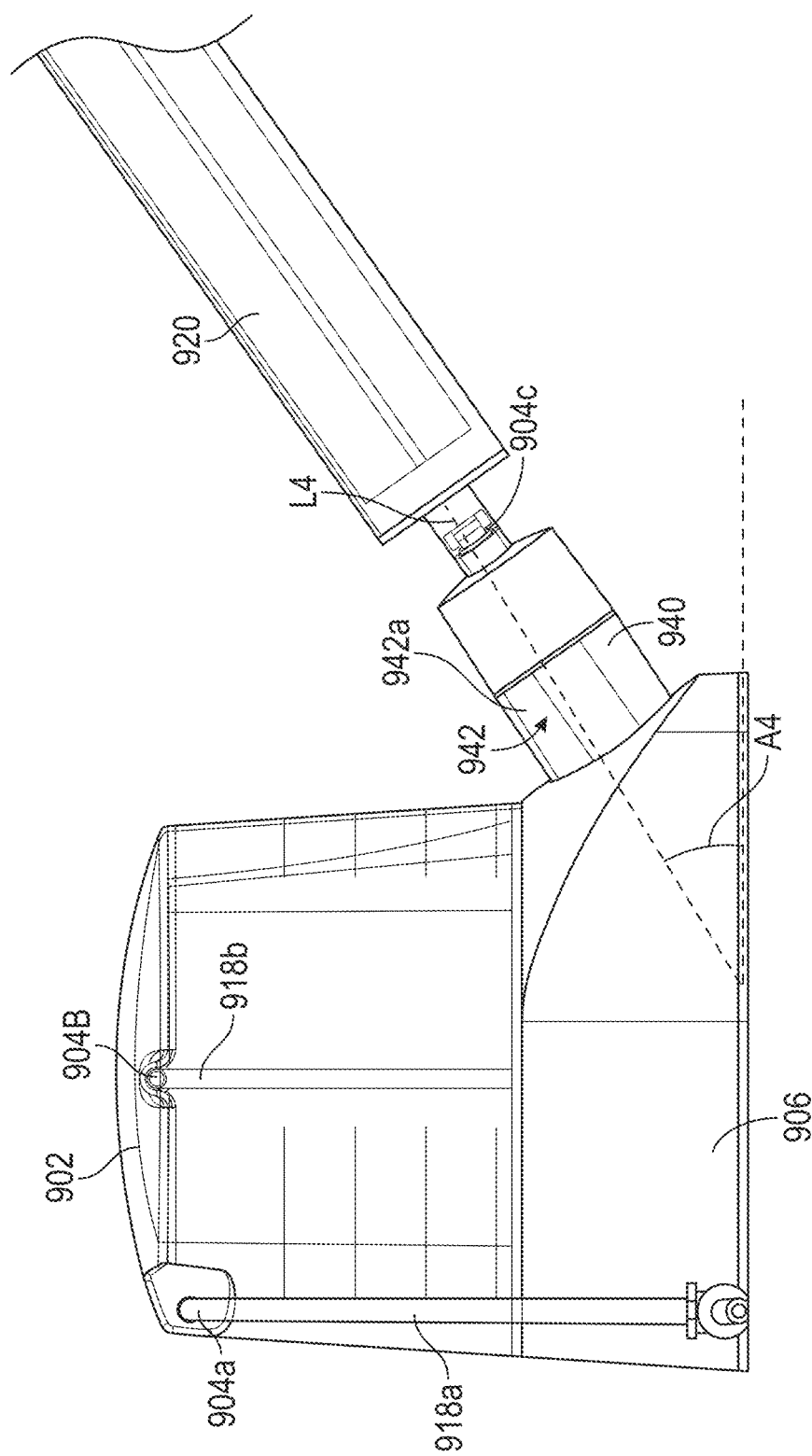

DEVICES FOR BLOOD CAPTURE AND REINTRODUCTION DURING ASPIRATION PROCEDURE

BACKGROUND

Thrombotic restrictions and occlusions within a patient's blood vessels are a significant medical problem and often require intervention to remove these restrictions and blockages to restore health to patients. While applicable to a wide range of vascular applications in both the arterial and venous systems, including a variety of small vessels, the following background illuminates the problems primarily through the example of patients suffering with Pulmonary Embolisms.

Venous thromboembolic disease (VTE) is a worldwide crisis. There are over 10 million cases of deep vein thrombosis (DVT) and pulmonary embolism (PE) diagnosed globally per year, with 1 million cases occurring in the United States and over 700,000 in France, Italy, Germany, Spain, Sweden, and the United Kingdom combined each year. There are approximately 60,000 to 100,000 deaths from PE in the United States each year. DVT and PE are part of the same continuum of disease, with over 95% of emboli originating in the lower extremities. When PE occurs, the severity depends on the embolic burden and its effect on the right ventricle as well as underlying cardiopulmonary comorbidities. Death can result from the acute increase in pulmonary artery (PA) pressure with increased right ventricular (RV) afterload and dysfunction.

Patients with high-risk pulmonary embolism (PE) were treated primarily with thrombolytic therapy delivered systemically or more locally through Catheter Directed Thrombolytics. These approaches result in multiple catheterization lab visits, lengthy hospital stays and often lead to bleeding complications. Newer approaches to PE treatment include single session thrombectomy treatments without the use of thrombolytics. These thrombectomy treatments include delivering a catheter into the PA to remove the thrombus through aspiration, and secondary tools may also macerate or disrupt the thrombus prior to aspiration. While thrombectomy results in fewer bleeding complications and reduced hospital stays compared to thrombolytics, there is much to be improved upon given the challenges of the procedure itself, including the ability to capture a broad spectrum of thrombus types and reduce the total volume of blood loss during the procedure.

The thrombectomy catheter is introduced through an introducer puncture in a large diameter vein. A flexible guide wire is passed through the introducer into the vein and the introducer is removed. The flexible guidewire provides a rail for a flexible guide catheter to be advanced through the right atrium into the right ventricle and into the pulmonary artery. The flexible guidewire is removed and replaced with a stiff guidewire. The large diameter thrombectomy catheter with support dilator is then advanced over the stiff guidewire to the pulmonary artery and the dilator is removed. If the large diameter thrombectomy catheter is not successful in accessing or aspirating thrombus in a more distal portion of the vessel, a smaller diameter catheter may be inserted through the large diameter catheter.

In addition, peripheral arterial occlusive (PAO) disease occurs in more than 4% of individuals over age 40 and markedly increases in incidence after the age of 70. Acute PAO is usually due to thrombosis of the peripheral vasculature and is associated with a significant risk of limb loss. In order to preserve the limb, therapy for acute PAO centers on the rapid restoration of arterial patency and blood flow such as through mechanical thrombectomy in procedures similar to those described above.

Clot aspiration using certain commercial vacuum-assisted thrombectomy systems may sometimes need to be terminated due to the risk of excessive blood loss by the patient, especially when using large aspiration catheters. During aspiration thrombectomy, when the catheter tip falls out of contact with the thrombus or other occlusive material, the tip is exposed to healthy blood and full flow of blood through the catheter ensues. Under such conditions, the total volume of blood loss is excessive, and in some cases, may result in premature termination of the procedure. For example, during a procedure when the catheter enters healthy blood and full aspiration flow ensues, the blood loss rate can be on the order of 20-30 cc per second with an 24 French size catheter. In order to minimize blood loss, the catheter should not run in unrestricted mode for more than approximately 10 to 15 seconds. The aggregate blood loss may reach an unacceptable level before sufficient clot is removed.

SUMMARY

There is provided in accordance with one aspect of the present disclosure a blood reintroduction system. The blood reintroduction system can include a sterile canister configured to collect blood, an inlet configured to be fluidly connected to a first tubing in fluid communication with an aspiration system configured to apply aspiration to a vasculature of a patient, a first outlet configured to be fluidly connected to a second tubing in fluid communication with an aspiration pump, and/or any vacuum source such as a syringe, and a second outlet configured to interact with a blood reintroduction device. The blood reintroduction device can be configured to withdraw the blood collected inside the sterile canister. The blood reintroduction device can include a filter positioned inside a flow path extending through the second outlet.

In some aspects, the filter can be positioned anywhere between the sterile canister and the vasculature of the patient.

In some aspects the filter is positioned inside the sterile canister.

In some aspects, the filter is positioned outside the sterile canister.

In some aspects, the filter is in fluid communication with the syringe.

In some aspects, the filter is in fluid communication with patient tubing and/or a patient port.

The inlet may be configured to direct an incoming stream of blood along an inside surface of the canister. In one implementation, the canister may have a curved wall such as in a cylindrical canister. The inlet may be configured to direct an incoming stream of blood along a circumferential path along the inside surface of the canister.

In some aspects, the filter is positioned between a chamber defined by the sterile canister and an opening of the second outlet. The filter can be configured to filter the blood before the blood is withdrawn from the sterile canister via the second outlet.

In some aspects, the inlet can be positioned on an upper portion of the sterile canister.

In some aspects, the first outlet can be positioned on an upper portion of the canister.

In some aspects, the canister further includes a base defining a blood collection cavity.

In some aspects, the filter is at least partially disposed inside the cavity. The second outlet can be positioned adjacent to the cavity.

In some aspects, the blood reintroduction device includes a syringe.

In some aspects, the blood reintroduction device includes a venous line in fluid communication with vasculature of the patient. A pump fluidly connected to the venous line can be configured to advance the blood withdrawn from the sterile canister into the vasculature of the patient.

In some aspects, the aspiration system includes a thrombectomy catheter and an aspiration catheter configured to be advanced through the thrombectomy catheter.

In some aspects, aspiration from the aspiration pump or any vacuum source, such as a syringe, is configured to draw blood from the first tubing into the sterile canister.

In some aspects, a longitudinal axis of the second outlet is positioned at an acute angle relative to a base of the sterile canister.

In some aspects, a longitudinal axis of the second outlet is positioned at a right angle relative to a base of the sterile canister.

In some aspects, the first and second tubing are configured to permit the sterile canister to reside within a sterile field.

In accordance with another aspect of the present disclosure, there is provided a method of capturing blood for reintroduction into a vasculature of a patient during an aspiration procedure. The method can include providing a canister to be placed in fluid communication with the vasculature of a patient. The canister can include an inlet, a first outlet, and a second outlet. The method can also include applying aspiration to the canister via the first outlet, and aspirating blood from the patient and into the canister via a first tubing connected to the inlet. The method can include filtering the blood collected inside the canister using a filter positioned in fluid communication between an opening of the second outlet and at least a portion of an internal space of the canister. The method can include withdrawing filtered blood from the canister via the second outlet.

In some aspects, the method can include introducing the filtered blood withdrawn from the canister into the vasculature of a patient.

In some aspects, applying aspiration to the canister via the first outlet includes connecting the first outlet with an aspiration pump via a second tubing.

In some aspects, aspirating blood from the patient and into the canister via the first tubing connected to the inlet includes inserting a thrombectomy catheter into the vasculature of the patient and advancing an aspiration catheter inside the thrombectomy catheter.

In some aspects, filtering the blood collected inside the canister using the filter positioned between the opening of the second outlet and at least the portion of the internal space of the canister includes flowing the blood through the filter to cause filtering of solid material.

In some aspects, the solid material comprises a blood clot and/or a thrombus.

In some aspects, withdrawing filtered blood from the canister via the second outlet includes coupling a syringe to the second outlet and withdrawing blood into the syringe.

In some aspects, withdrawing filtered blood from the canister via the second outlet includes connecting a first end of a venous line into the vasculature of the patient and a second end of the venous line to the second outlet. The method can also include pumping the filtered blood through the venous line using a pump fluidly connected to the venous line.

In some aspects, filtering the blood collected inside the canister using the filter positioned between the opening of the second outlet and at least the portion of the internal space of the canister includes collecting solid matter inside the filter.

In some aspects, withdrawing filtered blood from the canister via the second outlet can be done without interrupting application of aspiration to the canister via the first outlet.

In some aspects, the method can include prefiltering the blood prior to aspirating the blood into the canister using a second filter positioned along the first tubing.

In some aspects, filtering the blood collected inside the canister using the filter includes filtering solid materials of a first size, prefiltering the blood prior to aspirating the blood into the canister using the second filter includes filtering solid materials of a second size. In some aspects, the second size can be greater than the first size. In some aspects, the solid materials can include a thrombus.

In some aspects, aspirating blood from the patient and into the canister can include positioning the inlet to direct a flow of blood to an interior wall of the canister.

In some aspects, aspirating blood from the patient and into the canister includes collecting the blood within a base of the canister, the base comprising a first portion and a second portion, the first portion comprising an inclined surface and the second portion defining a dip.

In some aspects, filtering the blood collected inside the canister using the filter includes positioning at least a portion of a distal end of the filter within the dip so that the distal end of the filter is in contact with the blood collected in the dip.

In accordance with another aspect of the present disclosure, there is provided a blood reintroduction system. The blood reintroductions system can include a housing having a chamber configured to collect blood, an inlet configured to fluidly connect the chamber to a first tubing in fluid communication with an aspiration catheter, a first outlet configured to fluidly connect the chamber to a second tubing in fluid communication with an aspiration pump, and a second outlet configured to interact with a blood reintroduction device.

In some aspects, the blood reintroduction system is configured to reside within a sterile field.

In some aspects, the blood reintroduction system can include a filter positioned between an interior portion of the housing and an opening of the second outlet.

In some aspects, the blood reintroduction device is configured to withdraw blood collected inside the housing.

In some aspects, the blood reintroduction device includes a syringe.

In some aspects, the second outlet includes a luer fitting.

In some aspects, the aspiration catheter is configured to apply aspiration to a vasculature of a patient.

In some aspects, the housing includes a base defining a floor. The floor can include a first portion and a second portion. The first portion can include an inclined surface and the second portion can define a dip. The inclined surface of the first portion can facilitate flow of the blood collected inside the housing towards the dip defined by the second portion.

In some aspects, the blood reintroduction system can further include a filter. The filter can include a proximal end and a distal end. The distal end of the filter can be positioned at least partially within the dip defined by the second portion of the floor.

In some aspects, the blood reintroduction device can be configured to withdraw blood collected inside the canister while aspiration is applied by the aspiration pump.

In some aspects, the blood reintroductions system can include a filter positioned between the inlet and the aspiration catheter, the filter configured to capture thrombus as blood flows through the first tubing.

In some aspects, the blood reintroduction device includes a second tubing comprising a first end and a second end, the first end connected to the second outlet and the second end in fluid communication with a vasculature of a patient.

In some aspects, the second tubing can be in fluid communication with a pump, the pump configured to move the blood from the chamber to the vasculature of the patient via the tubing.

In some aspects, the blood reintroduction device includes a filter assembly having a filter housing, a filter positioned inside the filter housing and a cap configured to secure the filter housing to the housing of the blood reintroduction system.

In some aspects, the cap can be movable between at least an open position where the filter housing is not secured to the housing of the blood reintroduction system, and a closed position where the filter housing is secured to the housing of the blood reintroduction system.

In some aspects, at least a portion of the filter assembly can be positioned within the chamber and wherein at least a portion of the filter is in contact with the blood when blood is collected inside the chamber.

In accordance with another aspect of the present disclosure, there is provided a canister for use in a blood reintroduction system. The canister can include a housing, a base including a floor, the floor defining an inclined surface and a blood collection low point. The housing and the base can define a chamber configured to collect blood. The canister can include an inlet configured to be fluidly connected to a first tubing in fluid communication with a thrombectomy catheter. The inlet can be oriented to direct flow of blood along an interior side wall of the housing. The canister can include a first outlet configured to be fluidly connected to a second tubing in fluid communication with an aspiration pump, and a second outlet configured to interact with a blood reintroduction device. The blood reintroduction device can be configured to withdraw the blood collected inside the chamber. The canister can include a filter disposed between an opening of the second outlet and the chamber.

In some aspects, the inlet and the first outlet are positioned on an upper portion of the housing.

In some aspects, the inlet and the first outlet are positioned in an elevated position relative to the second outlet.

In some aspects, the filter includes a proximal end and a distal end. The distal end of the filter can be positioned adjacent the blood collection low point.

In some aspects, the filter and a bottom surface of the base define an acute angle.

In accordance with another aspect of the present disclosure, there is provided a filter assembly for use in a blood reintroduction system. The filter assembly can include a filter housing including a proximal end and a distal end, a cap removably secured to the proximal end of the filter housing, and a filter including a proximal end and a distal end. The filter can be positioned inside the filter housing. The filter assembly can include a luer fitting secured to the cap and configured to be in fluid communication with a blood reintroduction device. The filter housing can be configured to be at least partially disposed inside a canister.

In some aspects, a longitudinal axis of the filter housing can be positioned at an acute angle relative to a base of the canister.

In some aspects, the filter includes a filter having a pore size between 20 and 200 microns.

BRIEF DESCRIPTION OF THE DRAWINGS

FIGS. 11A-11C show a proximal handle for a dilator.

FIGS. 15A-15C show another example of a blood reintroduction system.

FIGS. 18A-18B show another example of a blood reintroduction system.

DETAILED DESCRIPTION

Figure 1:
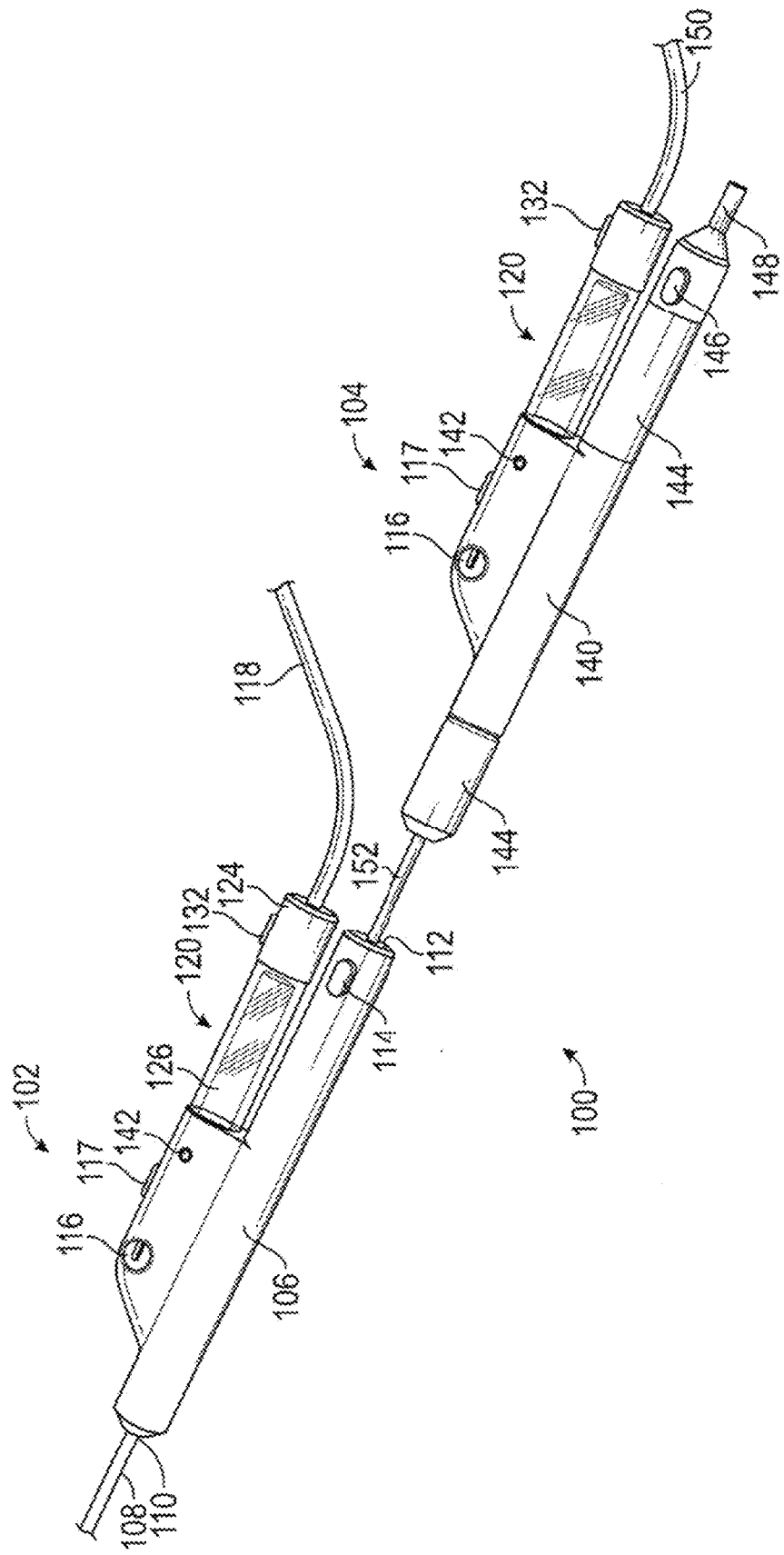
FIG. 1 is a schematic view of an alternative aspiration system having a first thrombectomy catheter and a second thrombectomy catheter extending therethrough.
Figure 2A:
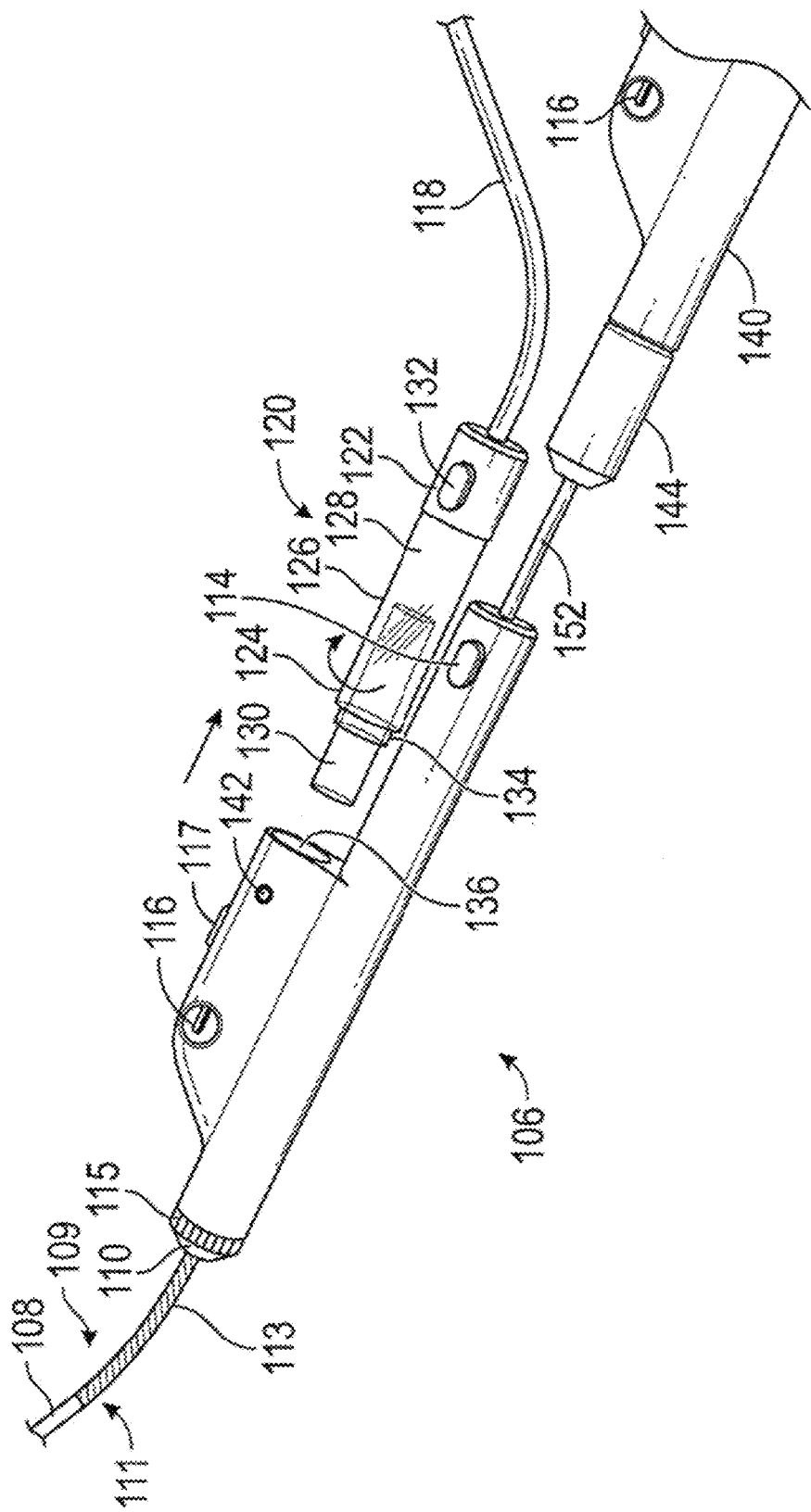
FIG. 2A is a schematic view of the proximal handle for the first thrombectomy catheter of FIG. 1.

Referring to FIGS. 1 and 2A, there is illustrated a further implementation of an aspiration system 100. The system includes a first thrombectomy catheter 102, such as a large bore aspiration catheter, and a second aspiration catheter 104 which is optionally advanceable through the first thrombectomy catheter 102 as has been discussed, or used by itself.

Thrombectomy catheter 102 comprises a proximal handle 106 having an elongate flexible tubular catheter body 108 extending distally therefrom. The proximal end 110 of the tubular body 108 may be permanently carried by the proximal handle 106 or may be provided with a releasable connector for detachable connection to a complementary connector on the handle 106.

In one implementation, the tubular body 108 or 152 or both are provided with a flexible neck 109 extending between proximal end 110 and a transition 111. The flexible neck 109 has a greater flexibility than the adjacent portion of the tubular body 108 distal to the transition 111. The flexible neck 109 may have a length of at least about 2 cm and often at least about 4 cm, but generally no more than about 20 cm or 10 cm or less.

The sidewall of the catheter body 108 within flexible neck 109 includes a helical coil 113 having adjacent filars spaced apart to both improve flexibility, and also allow visualization between adjacent windings of the coil. At least the flexible neck 109 includes a sidewall window such as the spaces between adjacent coil windings which may be in the form of an optically transparent outer tubular layer, such as any of a variety of optically transparent shrink tubing polymers. This allows visualization of clot through the side wall as it passes through the neck 109 before it enters the proximal handle. The transparent window on the larger catheter 108 also allows visualization of the distal tip of the inner catheter 152 as it passes the window. This may be facilitated by placing a visual marker on the distal end of the inner catheter 152 such as a colored annular band.

For example, in an implementation having a 24 French tubular body 108, the smaller tubular body 152 (e.g. 16 French catheter) may be provided with a visual indicium such as a white tip on the distal end, that can be visualized through the sidewall window as it passes through the flexible neck 109. The flexible neck 109 may also be provided on the catheter shaft 152.

The spring coil 113 may extend distally to a point of termination within about one or 2 cm of the transition 111, and, and one implementation, at the transition 111. Distally of the transition, the sidewall of tubular body 108 may include a tubular braid, importing greater stiffness and higher push ability than the helical coil 113.

The proximal end of the catheter may be provided with a rotation control such as a rotatable knob 115 which may be rotationally fixed to the catheter and rotatable with respect to the handle housing. This facilitates relative rotation between the catheter and the housing for any of the large or small bore catheters disclosed herein.

A central lumen extending through the tubular catheter body 108 is in communication with a flow path extending through the proximal handle 106 to a proximal access port 112. The flow path between the tubular catheter body 108 and the proximal access port 112 is preferably linear, to axially movably receive the second catheter 104 which may or may not be utilized in a given procedure. To accommodate the absence of second catheter 104 and seal the port 112, the proximal handle 106 is preferably provided with a homeostasis valve 114 such as a Thuohy-Borst valve.

A manifold switch 116 controls two way or three way a manifold valve (illustrated in FIG. 4) for selectively controlling fluid flow as discussed further below. An aspiration control 117 is provided to turn aspiration on and off. Alternatively, manifold switch 116 can be configured to turn aspiration one and off.

A filter assembly 120 includes housing 122 with a side wall 124, at least a portion of which includes a transparent window 126. Window 126 permits a viewing of the contents (e.g. aspirated clot) of a filter chamber 128, which contains a filter 130.

The filter assembly 120 is configured to place the filter 130 in the flow path between the tubular catheter body 108 and the aspiration tubing 118. Preferably the filter chamber can be closed to maintain negative pressure conveyed from a pump via aspiration tubing 118, or opened to permit insertion or removal of the filter 130. In the illustrated implementation, the filter assembly 120 is removably connected to the handle 106. A connector 134 such as a first thread on the housing 122 is releasably engageable with a complementary connector 136 such as a complementary thread on the handle 106. A vent (aperture) to atmosphere may be provided in communication with the filter chamber, to reduce foaming of blood in response to reduced pressure.

An implementation may include an integrated flow control module in the proximal handle 106. Thus, an adjustable flow regulator (not illustrated) may be positioned in the flow path, to enable controllable toggling of the aspiration between a low flow mode and a high flow mode. In the illustrated implementation, optional flow regulator is positioned downstream of the filter 130, and contained within the housing 122 of the filter assembly 120. A flow regulator control 132 is provided, to control the flow rate. Preferably, as has been discussed, the flow regulator is configured to regulate fluid flow through the flow path at a default low flow rate. Activation of the flow control 132 adjust the flow to the high flow rate mode. Flow control 132 may be a momentary button, slider switch, trigger, knob or other structure that is preferably defaulted to the low flow mode.

In any of the catheters disclosed herein, carrying the filter chamber 128 on the catheter or at least spaced apart from the remote vacuum pump and vacuum canister provides enhanced aspiration performance. The location of a conventional aspiration pump may be far enough away from the patient to require a length of aspiration tubing between the pump and the catheter to be as much as 50 inches or 100 inches or more. The pump typically includes an aspiration canister for blood collection. When aspiration is desired, a valve is opened to place the low pressure canister in communication with the catheter by way of the aspiration tubing, to aspirate material from the patient. But the length of the aspiration tubing operates as a flow restrictor, causing a delay between the time of activating the vacuum button and actual application of suction to the clot.

In some embodiments, the catheter handle 106 or 140 contains a filter chamber 128 for example, which is in communication with the vacuum canister on the pump by way of elongate aspiration tubing 118. The momentary aspiration control 117 is in between the filter chamber 128 and the catheter, which, in the default off position, allows the entire length of the aspiration tubing 118 and the filter chamber 128 to reach the same low pressure as the aspiration canister on the pump. The flow restriction between the pump canister 129 and the filter chamber 128 is greater than the flow restriction between the filter chamber 128 and the patient.

In an alternate configurations, 117 may be a vent to atmosphere which allows the clot canister to be evacuated. Element 142 can alternatively be an injection port such as for injecting contrast media, saline, or drugs.

Thus, the only remaining flow restrictor between a source of vacuum (filter chamber 128) and the patient is the relatively short aspiration pathway between the valve in the proximal handle and the distal end of the catheter. When the momentary aspiration control 117 is activated, the flow restriction and enclosed volume on the patient side of the filter chamber is low relative to the flow restriction and enclosed volume through aspiration tubing 118 on the pump side of the filter chamber 128.

This dual chamber configuration produces a rapid spike in negative pressure experienced at the distal end of the catheter upon activation of the aspiration control 117. The response time between activating the aspiration control 117 and realizing suction actually experienced at the clot is significantly faster and allows significantly higher initial flow than the response time realized in a conventional system having only a vacuum chamber located at the pump.

The spike of negative pressure experienced at the distal end of the catheter will fade as pressure equilibrium is reached between the filter chamber and canister. When the momentary aspiration control 117 is closed, the vacuum pump will gradually bring the pressure in the filter chamber 128 back down to the level in the vacuum canister at the pump.

Figure 3A:
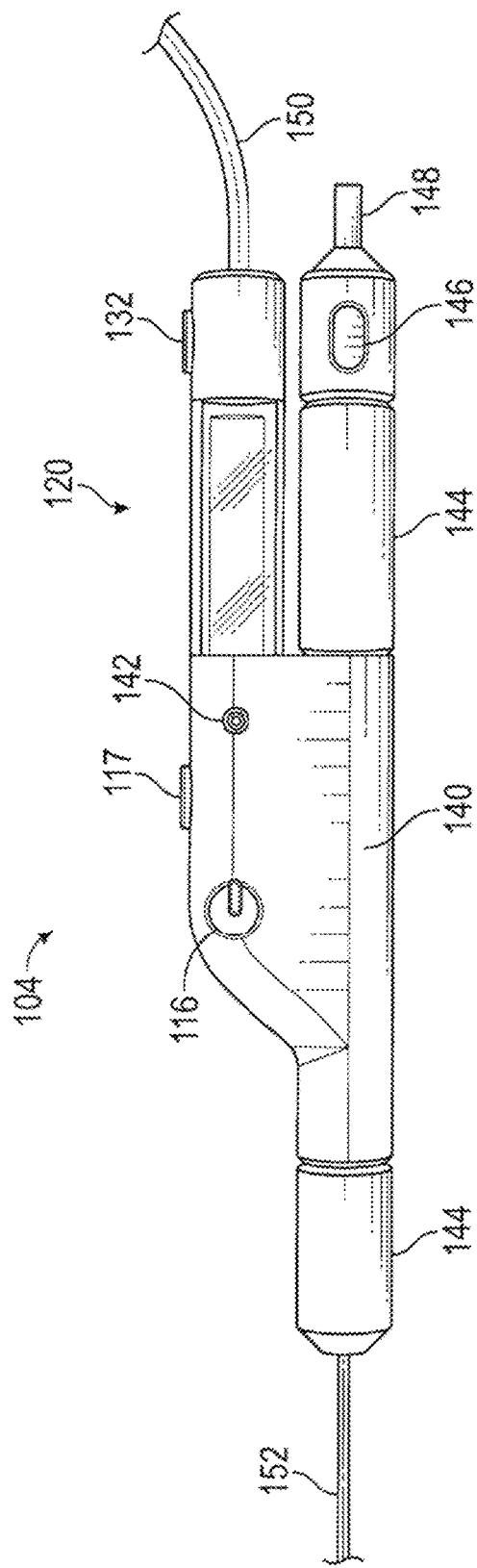
FIG. 3A is a schematic view of the proximal handle for the second thrombectomy catheter of FIG. 1.
Figure 3B:
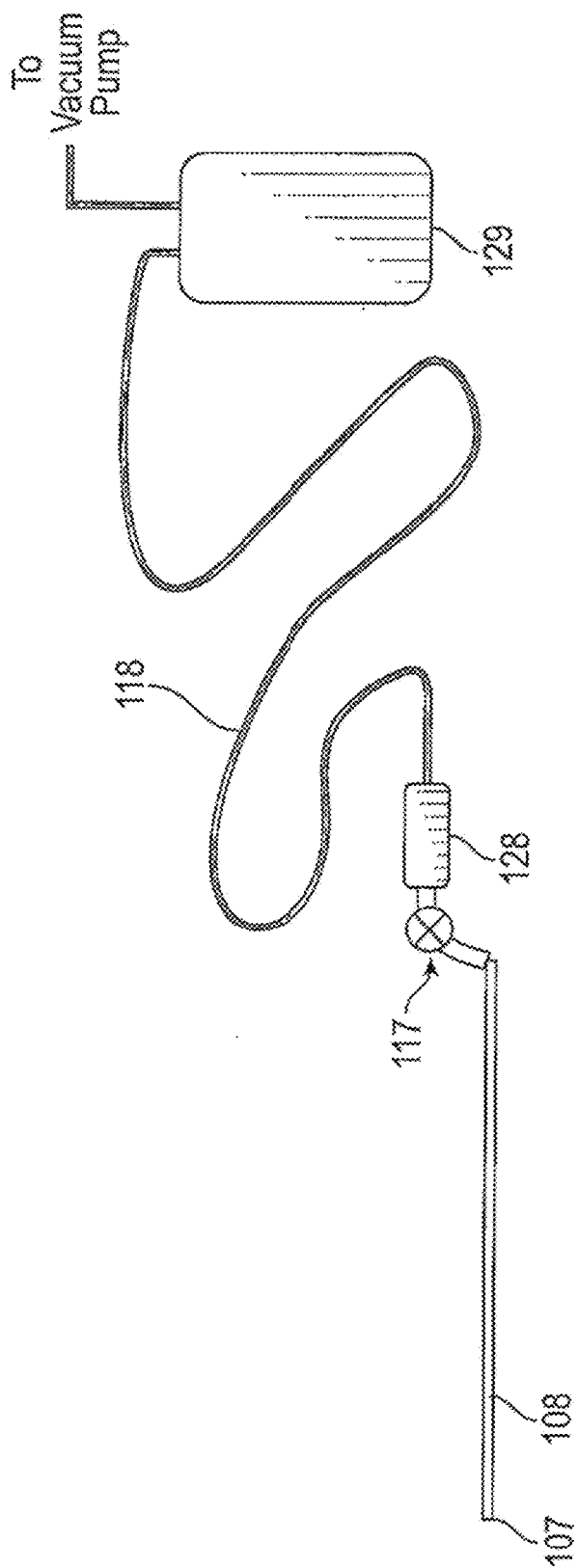
FIG. 3B is a simplified flow diagram of the dual vacuum chamber aspiration system.
Figure 3C:
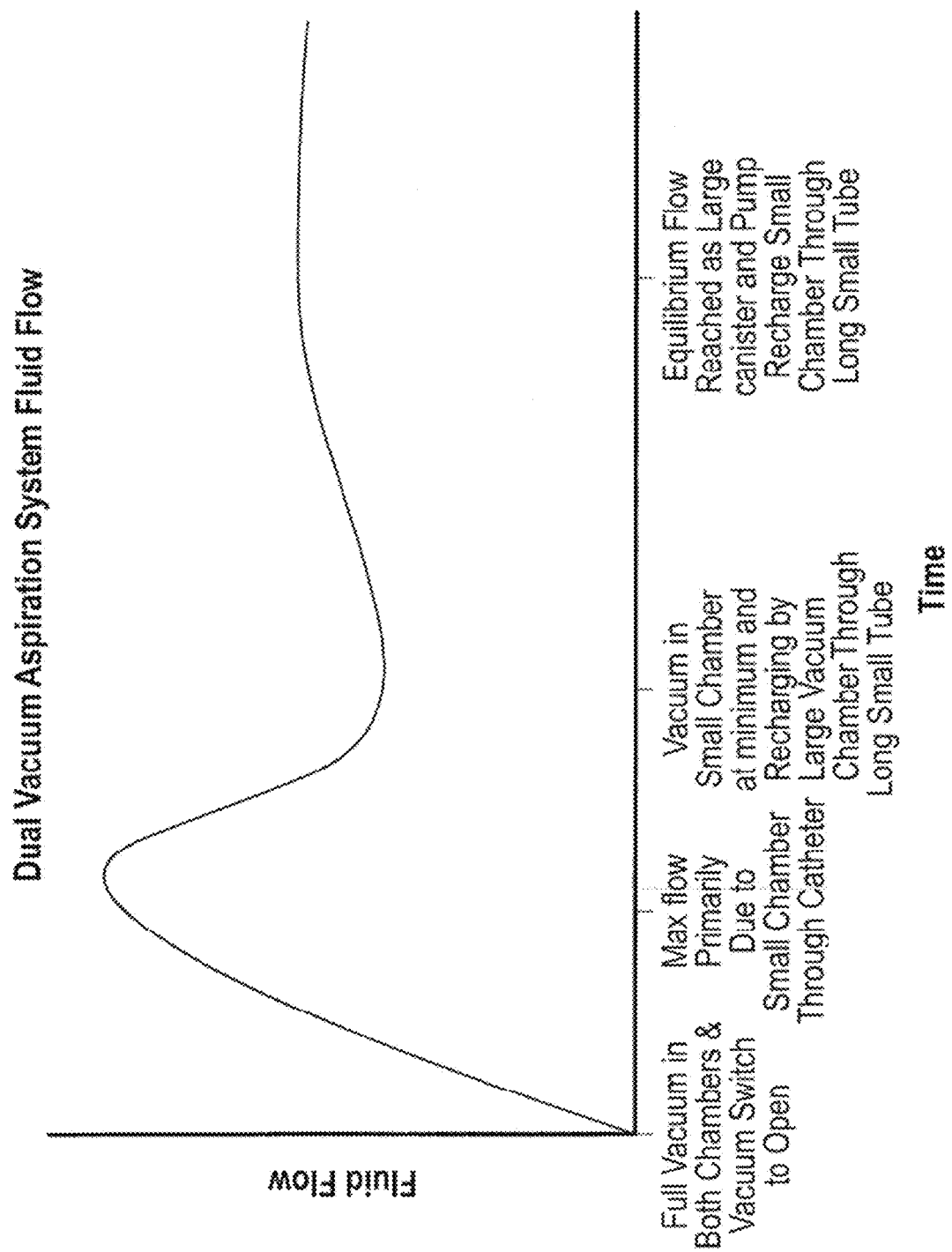
FIG. 3C is a qualitative fluid flow rate diagram at the catheter tip, following opening of the momentary vacuum control valve.

A simplified fluid flow diagram is illustrated in FIG. 3B, and a qualitative flow rate diagram is illustrated in FIG. 3C. The flow restriction between chamber 128 and the distal and 107 of catheter 108 is small relative to the flow restriction between the vacuum canister 129 and the vacuum chamber 128. This allows a negative pressure peak experienced at distal end 107 almost instantaneously upon activation of vacuum switch 117. The flow rate of material into the catheter 108 rapidly reaches a peak and subsides as vacuum chamber 128 fills with aspirated material. The vacuum in chamber 128 declines to a minimum, and slowly recharges by the large vacuum chamber 129 and associated pump through tubing 118. In use, a clinician may choose to allow the momentary vacuum switch 117 to close at or shortly following the maximum flow rate, just giving a short burst or spike of vacuum to facilitate spiration of thrombus into the catheter 108.

FIGS. 14A-23 illustrate views of various examples of blood reintroduction systems. It will be understood that any of the features, structures, materials, methods, or steps that is described and/or illustrated in any embodiment in any of the blood reintroduction systems of any one of FIGS. 14A-23 can be used with or instead of any feature, structure, material, method, or step that is described, illustrated, and/or contemplated herein.

Figure 14A:
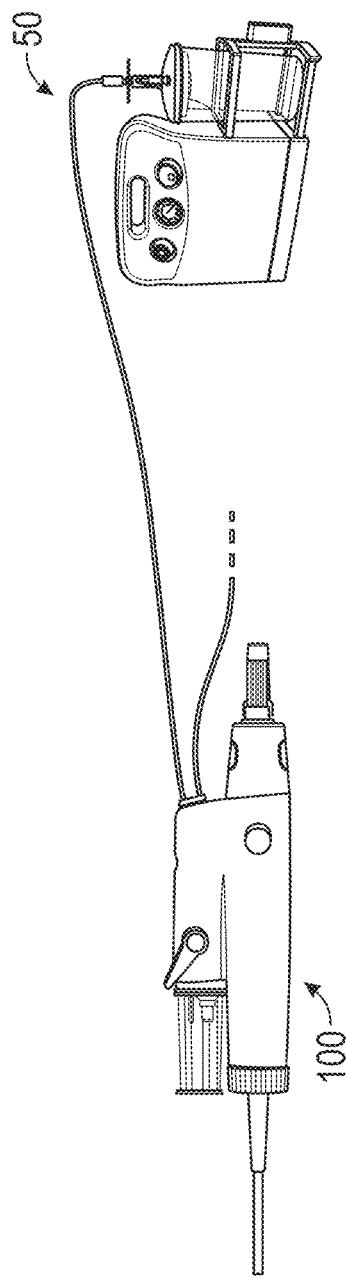
FIGS. 14A-14B show an example of a blood reintroduction system.
Figure 14B:
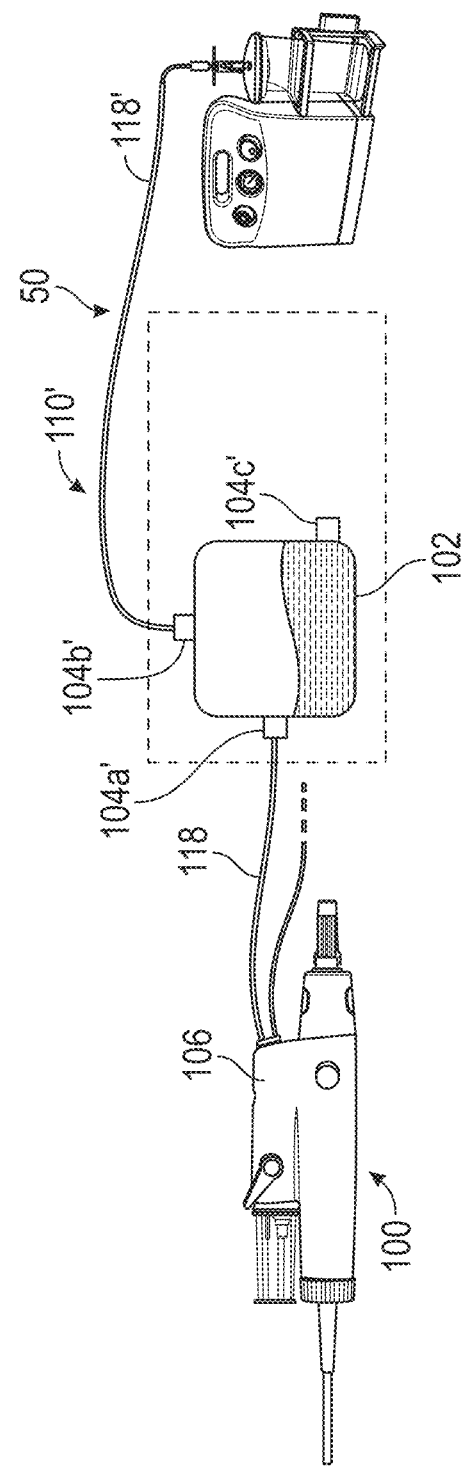

A blood reintroduction system 110' can be positioned between the aspiration system 100 and the aspiration pump 50, as shown in FIG. 14B. The blood reintroduction system 110' can include a canister 102' having one or more ports in fluid communication with the aspiration system 100 and/or the aspiration pump 50. For example, the canister 102' can include an inlet 104a', a first outlet 104b', and a second outlet 104c'. In some cases, the canister 102' and the aspiration system 100 are in fluid communication via the aspiration tubing 118. One end of the aspiration tubing 118 can be connected to the handle 106, which is described in relation to FIGS. 1-2A, and the other end can be connected to, for example, the inlet 104a'. The canister 102' and the aspiration pump 50 can be in fluid communication via tubing 118'. One end of the tubing 118' can be connected to, for example, the first outlet 104b' and the other end can be connected to the aspiration pump 50, which is described in relation to FIG. 1-8. In some cases, the port 104c' can act as an extraction port for clinicians to extract blood collected inside the canister 102'. Blood can be extracted from the canister 102' via the second outlet 104c' using, for example, a syringe. The aspiration pump 50 can provide aspiration via the tubing 118' and the tubing 118. The aspiration can facilitate collection of blood and debris inside the canister 102'. In some cases, the blood reintroduction system 110' can be positioned within a sterile field.

To facilitate the extraction of blood at the second outlet 104c' (e.g., the extraction port) and to prevent air from being drawn into the syringe, the canister 102' can include a tapering bottom portion. For example, the interior bottom portion of the canister 102' can taper such as conically, narrow end towards the bottom portion, or otherwise inclined, to improve the flow of blood towards a low point of the canister 102' in communication with the second outlet 104c'. Beneficially, this can improve the concentration of blood at or near the second outlet 104c' allowing clinicians to extract blood from the canister 102' via the second outlet 104c'. The canister 102' can also include one or more support structures for maintaining an upright position or securing the canister to a patient and/or pole/bedrail. In some cases, the canister 102' can include a downwardly extending skirt and/or legs to allow the canister 102' to sit on a surface and remain in its upright position so that the outlet 104c' communicates directly with the lowest point of the canister 102'. The body of the canister 102' or support structures removably or permanently carried by the canister 102' can also be shaped to conform to the shape of a patient's body. For example, a base of the canister 102' can be contoured to sit across the top of a patient's legs. In some cases, the canister can include one or more support structures, such as a hook, for removably placing the canister on an IV pole and/or bedrail.

In some cases, the blood reintroduction system 110' can include a flop tube (not shown). The flop tube can include weight on one end which can cause that end to gravitate towards a typically hemispherical bottom interior wall of the canister 102' regardless of the orientation of the canister 102'. The weight of the flop tube can beneficially place the opening of the flop tube in contact with a bottom portion of the canister 102' thus ensuring that the syringe draws fluids from a bottom a bottom portion of the canister 102' and preventing the syringe from drawing air.

Blood extracted from the canister 102' via the second outlet 104c' can be reintroduced to a patient. For example, blood extracted by the extraction device, such as the syringe, can be injected directly or indirectly to a patient. In some cases, the blood can be injected into the vasculature of a patient. The blood can also be injected into a patient from the syringe to, for example, a venous line connected to a patient. In some cases, the blood reintroduction system 110' can include a venous line (not shown) connected to a patient on one end and to the second outlet 104c' on the other end. The venous line can beneficially facilitate fluid reinfusion into a patient by drawing blood collected inside the canister 102' to the patient via the venous line. In such cases, it may not be necessary for clinicians to manually extract blood from the canister 102' and reinfuse the blood to the patient. That is, blood collected inside the canister 102' can be automatically reinfused by flowing though the venous line into the vasculature of a patient or a flow path into a vasculature of patient, such as flow path 32 which is described in relation to FIGS. 1 and 3. The venous line can be in fluid communication with a pump to facilitate blood reinfusion by flowing blood from the canister 102' to the patient.

Figure 15A:
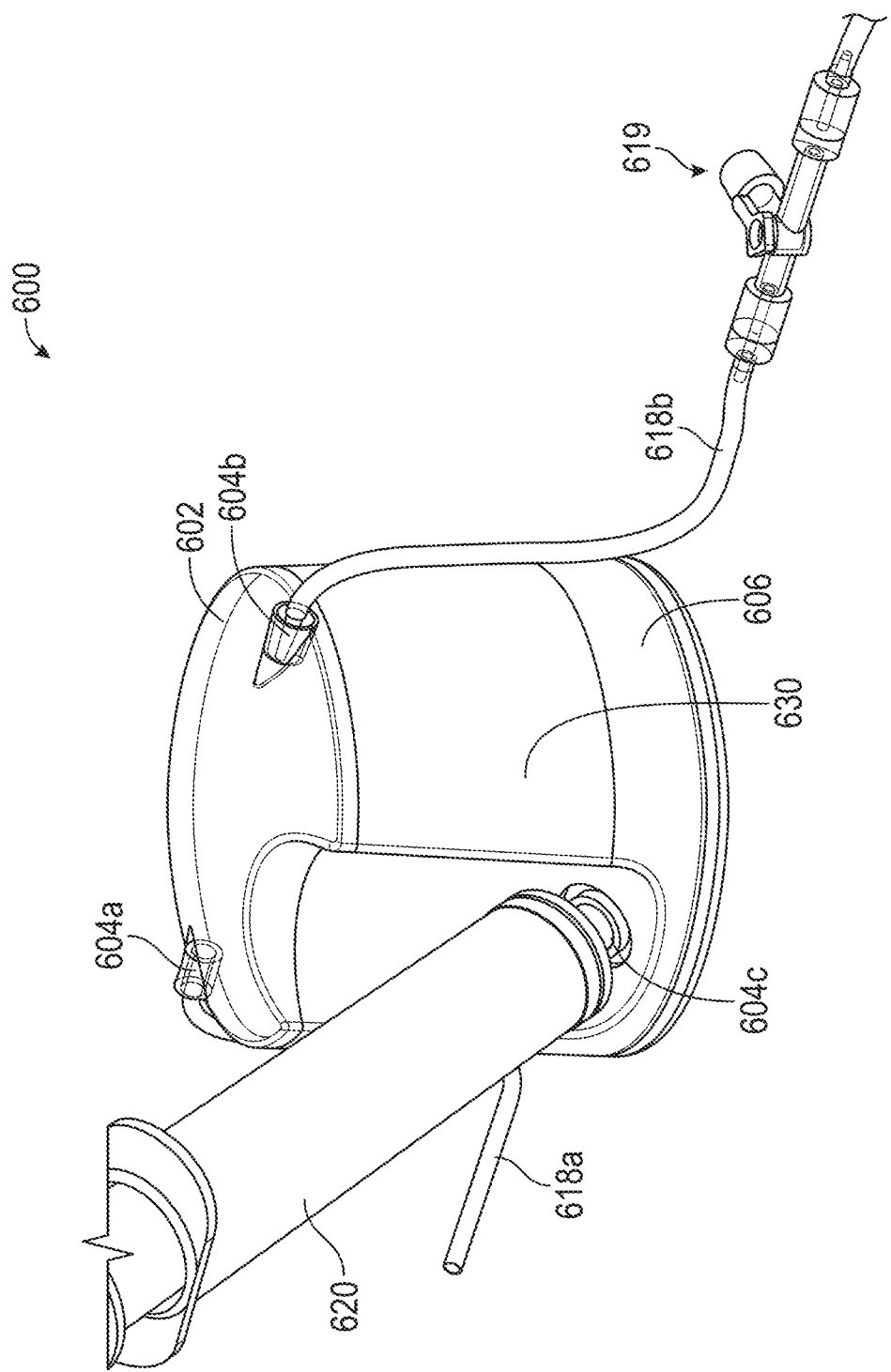
Figure 15B:
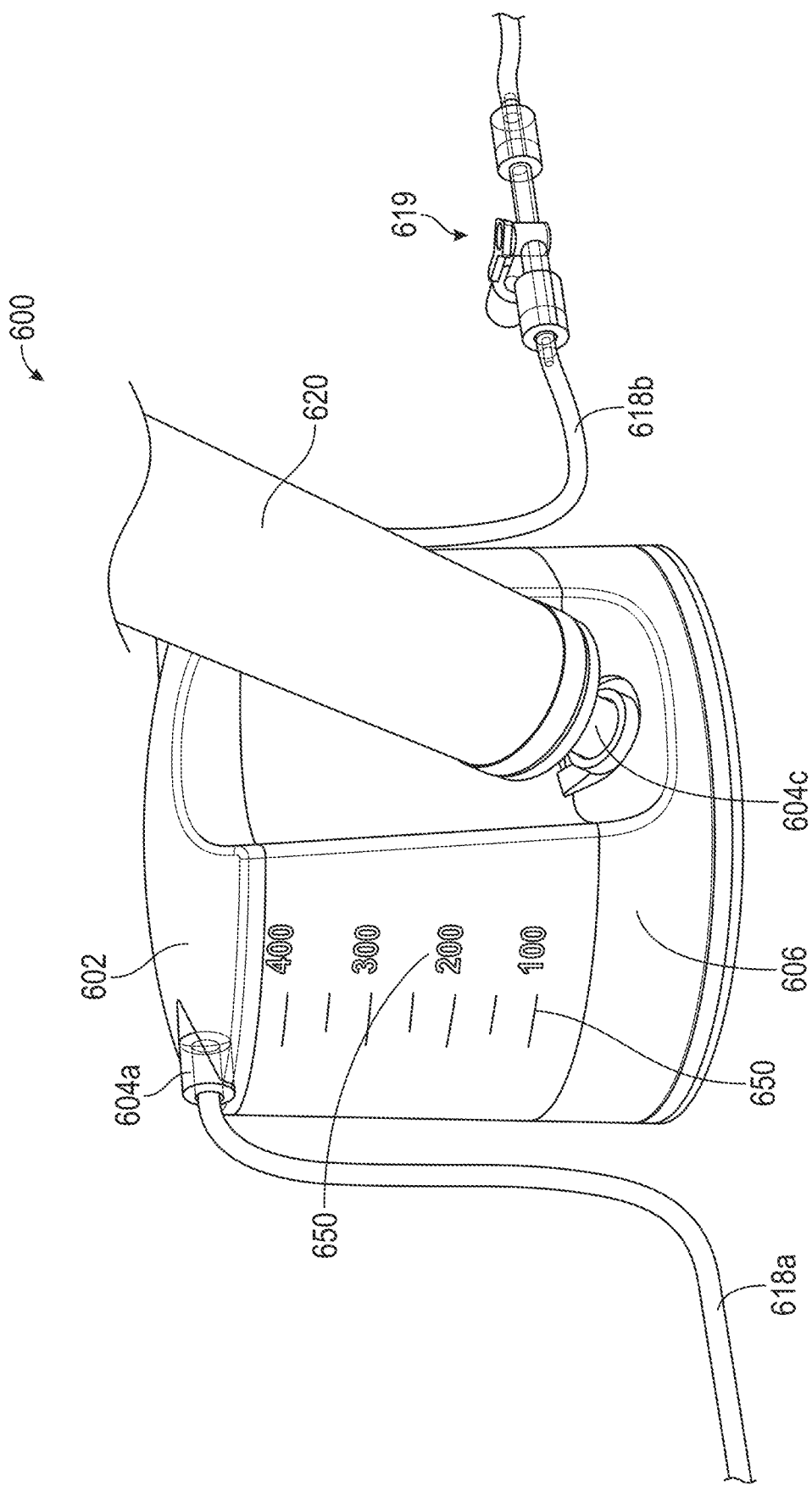

FIGS. 15A-15C show an example of a blood reintroduction system. The blood reintroduction system 600 can include a canister 602, an inlet 604a, a first outlet 604b, a second outlet 604c, and a base 606. The canister 602 can include graduations to easily visualize and/or measure the amount of blood collected within the canister 602. For example, the canister 602 can include one or more graduations 650 which can beneficially provide an indication of the amount of fluid 630 (e.g., blood) collected inside the canister 602. The inlet 604a and the first outlet 604b can be connected to other medical devices via tubing. For example, a first aspiration tubing 618a can be connected to the inlet 604a, and a second aspiration tubing 618b can be connected to the first outlet 604b. The first aspiration tubing 618a can place the canister 602 and an aspiration system, such as aspiration system 100 (as described in relation to FIG. 1) in fluid communication with each other. The first and second aspiration tubing 618a, 618b can include high pressure braided tubing. In some cases, the blood reintroduction system 600 can be positioned within a sterile field.

Blood drawn into the canister 602 via the first aspiration tubing 618a can collect on a bottom portion of the canister 602. The second aspiration tubing 618b can place an upper air space within the canister 602 and an aspiration pump, such as aspiration pump 50 (as described in relation to FIGS. 1-8) in fluid communication with each other. The vacuum generated by the aspiration pump 50 can beneficially facilitate aspiration of blood from the first aspiration tubing 618a to the canister 602. Although reference is made to the second aspiration tubing 618b being in fluid communication with an aspiration pump, the second tubing 618b can be in communication with any vacuum source. For example, the second tubing 618b can be in communication with a syringe. In operation, the negative pressure exerted by the syringe can facilitate aspiration via the first tubing 618a.

The interior surface of the canister 602 can include a coating to provide one or more of a variety of properties to the canister 602. In some instances, the coating may be configured to enhance visualization through at least a portion of the canister 602. The coating may be configured to inhibit blood accumulation or increase blood repellant properties. In some instances, the canister 602 may comprise a coating to inhibit foam formation during an aspiration procedure. The coatings may be located at least partially along an interior surface of the canister 602. The coating can be both hydrophobic and oleophobic. In some instances, the coating may have some hydrophilic features on a portion of the polymer to increase oleophobic properties.

The first aspiration tubing 618a and the second aspiration tubing 618b can include one or more valves. For example, the first aspiration tubing 618a and/or the second aspiration tubing 618b can include one or more stopcock valves 619. Opening and/or closing the stopcock valve 619 along the first aspiration tubing 618a and/or the second aspiration tubing 618b can beneficially allow users to control aspiration and/or the flow of blood through the first aspiration tubing 618a and/or the second aspiration tubing 618b. Opening the stopcock 619 can open the first aspiration tubing 618a and/or the second aspiration tubing 618b to atmosphere to facilitate withdrawal of blood by allowing venting of atmospheric air into the canister 602 regulate and/or equalize pressure while withdrawing blood via a syringe 620.

In some cases, the inlet 604a and the first outlet 604b can be positioned on a top portion of the canister 602. The inlet 604a and the first outlet 604b can be positioned on opposite ends of the canister 602. Positioning the first outlet 604b on a top portion of the canister 602 can beneficially prevent the first outlet 604b, which is in fluid connection with an aspiration pump, such as aspiration pump 50 which is described in relation to FIGS. 1-8, from aspirating fluid 630 and instead allow the fluid 630 to collect inside the canister 602. The second outlet 604c can be positioned on or in communication with a bottom portion of the canister 602 such as the lowest point in the chamber to optimize blood removal. In some cases, the second outlet 604c can include a luer fitting. The second outlet 604c can receive a medical device, such as the syringe 620. For example, a syringe can be used to extract fluid 630 (e.g., blood) collected inside the canister 602 by inserting the syringe 620 inside the second outlet 604c and extracting the fluid 630. To prevent fluid 630 from escaping the canister 602 via the second outlet 604c, the second outlet 604c can include a self-closing valve such as a displaceable membrane which obstructs the outflow path unless displaced such as by the distal tip of the syringe coupled to the outlet 604c. The membrane can be disposed inside the second outlet 604c and block the flow of liquid from an interior of the canister 602 to the exterior.

The syringe 620 can be used to extract fluid 630 from the canister 602 via the second outlet 604c. This can beneficially allow users to withdraw fluids 630 (e.g., blood) collected inside the canister 602 for infusion into a patient without significant, or any, interruption in the aspiration procedure and/or any disconnection of any components of the blood reintroduction system 600. That is, a physician or user may simply engage the syringe 620 to the second outlet 604c at any point during the aspiration procedure to withdraw blood from the canister 602 and reintroduce the blood to the patient. This can allow blood to be withdrawn from the canister 602 while still applying aspiration to the canister 602 and/or any of the devices and/or components in fluid communication with the canister 602 (e.g., the first tubing 618a, the inlet 604a, an aspiration catheter, etc.). Positioning of the blood reintroduction system 600 within a sterile field can significantly reduce the risk of blood contamination prior to reintroduction of the blood into the patient.

Fluid 630 extracted from inside the canister 602 via the second outlet 604c can be reintroduced to a patient. For example, the fluid 630 extracted by the extraction device, such as the syringe 620, can injected directly or indirectly to a patient. In some cases, the fluid 630 can be injected into the vasculature of a patient. The fluid 630 can also be injected to a patient from the syringe 620 to, for example, a venous line connected to a patient. In some cases, the blood reintroduction system 600 can include a venous line (not shown) connected to a patient on one end and to the second outlet 604c on the other end. The venous line can beneficially facilitate fluid reinfusion into a patient by drawing fluid 630 collected inside the canister 602 to the patient via the venous line. In such cases, it may not be necessary for clinicians to manually extract fluid 630 from the canister 602 and reinfuse the fluid 630 to the patient. That is, fluid 630 collected inside the canister 602 can be automatically reinfused by flowing though the venous line into the vasculature of patient or a flow path into a vasculature of patient, such as flow path 32 which is described in relation to FIGS. 1 and 3. Reinfusion may be assisted by a pump in between the outlet 604c and the patient (not illustrated).

In some cases, the blood reintroduction system 600 can include one or more filters. The one or more filters can be positioned upstream of the second outlet 604c, at the second outlet 604c, at the syringe 620, and/or along a flow path (e.g., a venous line between the second outlet 604c and the patient) before reinfusion of the fluid 630 to the patient. In some cases, the one or more filters can be positioned between a downstream opening of the second outlet 604c and an upstream internal space of the canister 602.

For example, the blood reintroduction system 600 can include a filter 640, as shown in in FIG. 15C. The filter 640 can be positioned inside a cavity 606a of the base 606. In some cases, a shape and/or dimensions of the cavity 606a are larger than a shape and/or dimensions of the filter 640 to allow the cavity 606a to receive and secure the filter 640. The filter 640 can prevent solid material, such as a blood clot and/or thrombus, collected inside the canister 602 from reaching the second outlet 604c. This can beneficially prevent solid matter from being extracted via the second outlet 604c using an extraction device, such as the syringe 620. The filter 640 can trap solid matter while allowing fluids, such as fluid 630 (e.g., blood), to flow through the filter 640. In some cases, a cavity 622 is positioned between the filter 640 and the second outlet 604c, as shown in FIG. 15C. The space between the filter 640 and the second outlet 604c provided by the cavity 622 can collect the fluid 630 exiting the filter 640 (e.g., filtered blood). The filter 640 can beneficially allow filtering of the blood prior to introduction of the blood into the patient.

Although reference is made to the filter 640 being positioned inside the cavity 606a of the base 606, the filter 640 can be positioned anywhere along a flow path extending from the inlet 604a to the second outlet 604. In some cases, the filter 640 can be positioned anywhere between the canister 602 and the vasculature of the patient. In some cases, the blood reintroduction system 600 can include more than one filter 640. For example, the system 600 can include a first filter positioned distal to the inlet 604a and a second filter proximal to the inlet 604b. The first and second filters can include the same or different filter ratings. For example, the first filter can include pores larger than the pores of the second filter. This can prevent clots and/or particles larger than a porosity of the first filter from reaching the canister 602. The use of two or more filters can beneficially prevent any solid material, such as a blood clots and/or thrombus, from reaching the second outlet 604c. In some cases, the first filter can be part or otherwise positioned within the handle 106 of the aspiration system 100 (as described in relation to FIG. 1), and the second filter can include the filter 640 (as described in relation to FIGS. 15A-15C). This configuration, in some instances, may advantageously permit pre-filtered blood to into the blood reintroduction system 600 to provide an additional filtration layer prior to blood withdrawal and reintroduction into a patient.

In some cases, a longitudinal axis of the second outlet 604c can incline from a plane defined by the base 606 at an angle. For example, a longitudinal axis L1 of the second outlet 604c and the base 606 can form an angle A1, as shown in FIG. 15C. In some cases, the angle A1 can be an acute angle. For example, the angle A1 can be between about 10° and about 80°. For example, the angle A1 can be between about 100 and about 40°, between about 200 and about 50°, between about 300 and about 60°, between about 400 and about 70°, or between about 500 and about 80°. In some cases, the angle can be about 45°. The angle A1 can ensure that the extraction mechanism (e.g., the needle) of the syringe 620 can connect to a bottom portion of the canister 602, such as the low point in cavity 622 without mechanical interference from the sidewall of the canister 602. This can beneficially allow the syringe 620 to draw fluid 630 collected on a bottom portion of the canister 602 and prevent the syringe 620 from drawing air.

Figure 16:
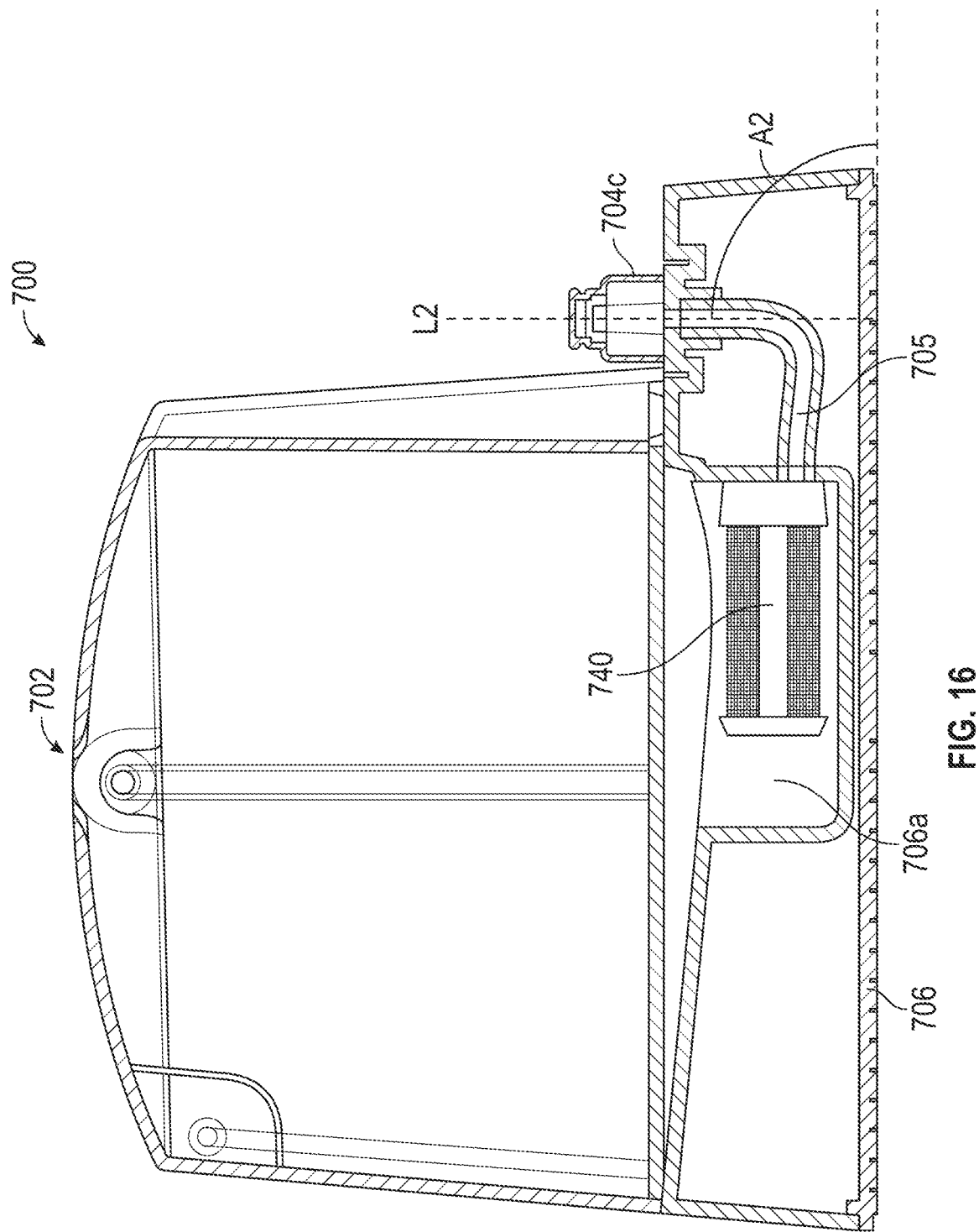
FIG. 16 shows another example of a blood reintroduction system.

FIG. 16 shows another example of a blood reintroduction system. Like the blood reintroduction system 600, the blood reintroduction system 700 can include a canister 702, an inlet, a first outlet, a second outlet 704c, and a base 706. The inlet and the first outlet can be connected to other medical devices via tubing. For example, a first aspiration tubing can be connected to the inlet, and a second aspiration tubing can be connected to the first outlet. The first aspiration tubing can place the canister 702 and an aspiration system, such as aspiration system 100 (as described in relation to FIG. 1) in fluid communication with each other. Blood drawn into the canister 702 via the first aspiration tubing can collect on a bottom portion of the canister 702. The second aspiration tubing can place the canister 702 and an aspiration pump, such as aspiration pump 50 (as described in relation to FIGS. 1-8) in fluid communication with each other. The vacuum generated by the aspiration pump 50 can beneficially facilitate aspiration of blood from the first aspiration tubing to the canister 702.

Like the blood reintroduction system 600, the blood reintroduction system 700 can include one or more filters. The one or more filters can be positioned upstream of the second outlet 704c, at the second outlet 704c, at a syringe, and/or along a flow path (e.g., a venous line between the second outlet 704c and the patient) before reinfusion of the fluid to the patient. In some cases, the one or more filters can be positioned between an outlet opening of the second outlet 704c and an internal volume of the canister 702. For example, the blood reintroduction system 700 can include a filter 740. The filter 740 can be positioned inside a cavity 706a of the base 706. In some cases, a shape and/or dimensions of the cavity 706a are larger than a shape and/or dimensions of the filter 740 to allow the cavity 706a to receive and secure the filter 740. The filter 740 can prevent solid matter, such as thrombus, collected inside the canister 702 from reaching the second outlet 704c. This can beneficially prevent solid matter from being extracted via the second outlet 704c using an extraction device, such as a syringe. The filter 740 can trap solid matter while allowing fluids (e.g., blood), to flow past the filter 740. In some cases, the second outlet 704c can include an extension tube 705 in fluid communication with the filter 740. The extension tube 705 can be sealed to one end of the filter 740, as shown in FIG. 16. A lumen inside the extension tube 705 can direct the fluid exiting the filter 740 (e.g., filtered blood) to the second outlet 704c.

In some cases, the second outlet 704c can extend from a base 706 at an angle. For example, a longitudinal axis L2 of the second outlet 704c and the base 706 can form an angle A2, as shown in FIG. 16. Unlike the angle A1 of the blood reintroduction system 600, the angle A2 of the blood reintroduction system 700 can include a right angle. For example, the angle A2 can be between about 90° and about 45°, between about 90° and about 75°, or between about 80° and about 70°. The angle A2 can ensure that the syringe can couple to the outlet port on extension tube 705 without mechanical interference from the canister 702. This can beneficially allow the syringe to draw filtered fluid through the extension tube 705 and prevent the syringe from drawing air.

Figure 17:
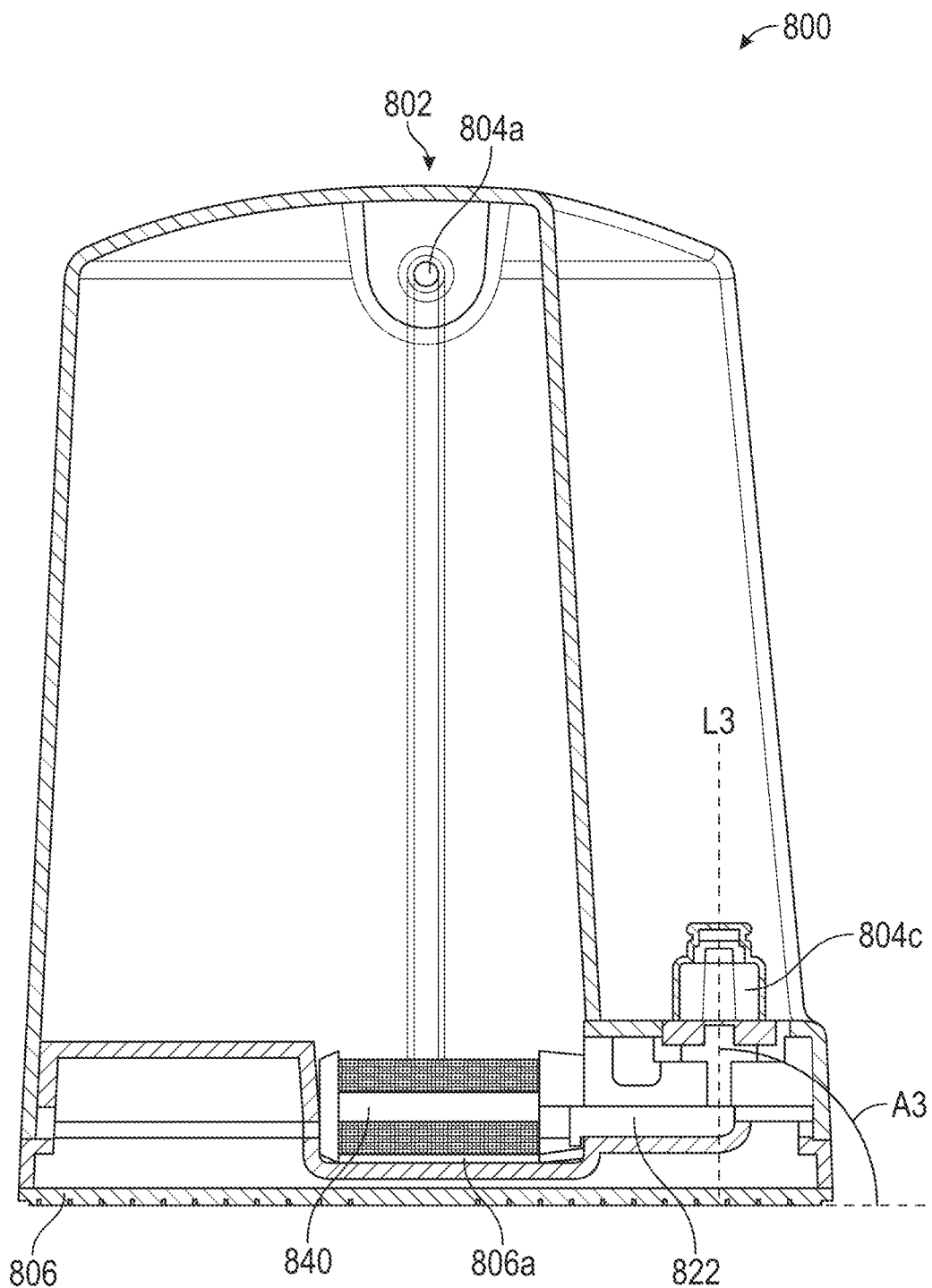
FIG. 17 shows another example of a blood reintroduction system.

FIG. 17 shows another example of a blood reintroduction system. Like the blood reintroduction systems 600 and 700, the blood reintroduction system 800 can include a canister 802, an inlet 804a, a first outlet, a second outlet 804c, and a base 806. The inlet 804a and the first outlet can be connected to other medical devices via tubing. For example, a first aspiration tubing can be connected to the inlet 804a, and a second aspiration tubing 818b can be connected to the first outlet. The first aspiration tubing can place the canister 802 and an aspiration system, such as aspiration system 100 (as described in relation to FIG. 1) in fluid communication with each other. Blood drawn into the canister 802 via the first aspiration tubing can collect on a bottom portion of the canister 802. The second aspiration tubing can place the canister 802 and an aspiration pump, such as aspiration pump 50 (as described in relation to FIGS. 1-8) in fluid communication with each other. The vacuum generated by the aspiration pump 50 can beneficially facilitate aspiration of blood from the first aspiration tubing to the canister 802.

Like the blood reintroduction systems 600 and 700, the blood reintroduction system 800 can include one or more filters. The one or more filters can be positioned upstream of the second outlet 804c, at the second outlet 804c, at a syringe, and/or along a flow path (e.g., a venous line between the second outlet 804c and the patient) before reinfusion of the fluid to the patient. In some cases, the one or more filters can be positioned between a downstream opening of the second outlet 804c and an internal volume of the canister 802. For example, the blood reintroduction system 800 can include a filter 840. The filter 840 can be positioned inside a cavity 806a of the base 806. In some cases, a shape and/or dimensions of the cavity 806a are larger than a shape and/or dimensions of the filter 840 to allow the cavity 806a to receive and secure the filter 840. The filter 840 can prevent solid matter, such as thrombus, collected inside the canister 802 from reaching the second outlet 804c. This can beneficially prevent solid matter from being extracted via the second outlet 804c using an extraction device, such as a syringe. The filter 840 can trap solid matter while allowing fluids (e.g., blood), to flow past the filter 840. Like the blood reintroduction system 600, the blood reintroduction system 800 can include a cavity 822 positioned between the filter 840 and the second outlet 804c, as shown in FIG. 17. The space between the filter 840 and the second outlet 804c provided by the cavity 822 can collect the fluid exiting the filter 840 (e.g., filtered blood).

In some cases, a longitudinal axis L3 of the second outlet 804c and a base 806 can form an angle A3. Like the angle A2 of the blood reintroduction system 700, the angle A3 of the blood reintroduction system 800 can include a right angle relative to the plane of the base. For example, the angle A3 can be between about 90° and about 45°, between about 90° and about 75°, or between about 80° and about 70°. The angle A3 can ensure that the extraction mechanism (e.g., the needle) of the syringe can couple to the outlet port 804c on the cavity 822 without mechanical interference from the canister 802. This can beneficially allow the syringe to draw filtered fluid through the cavity 822 and prevent the syringe from drawing air.

Figure 18A:
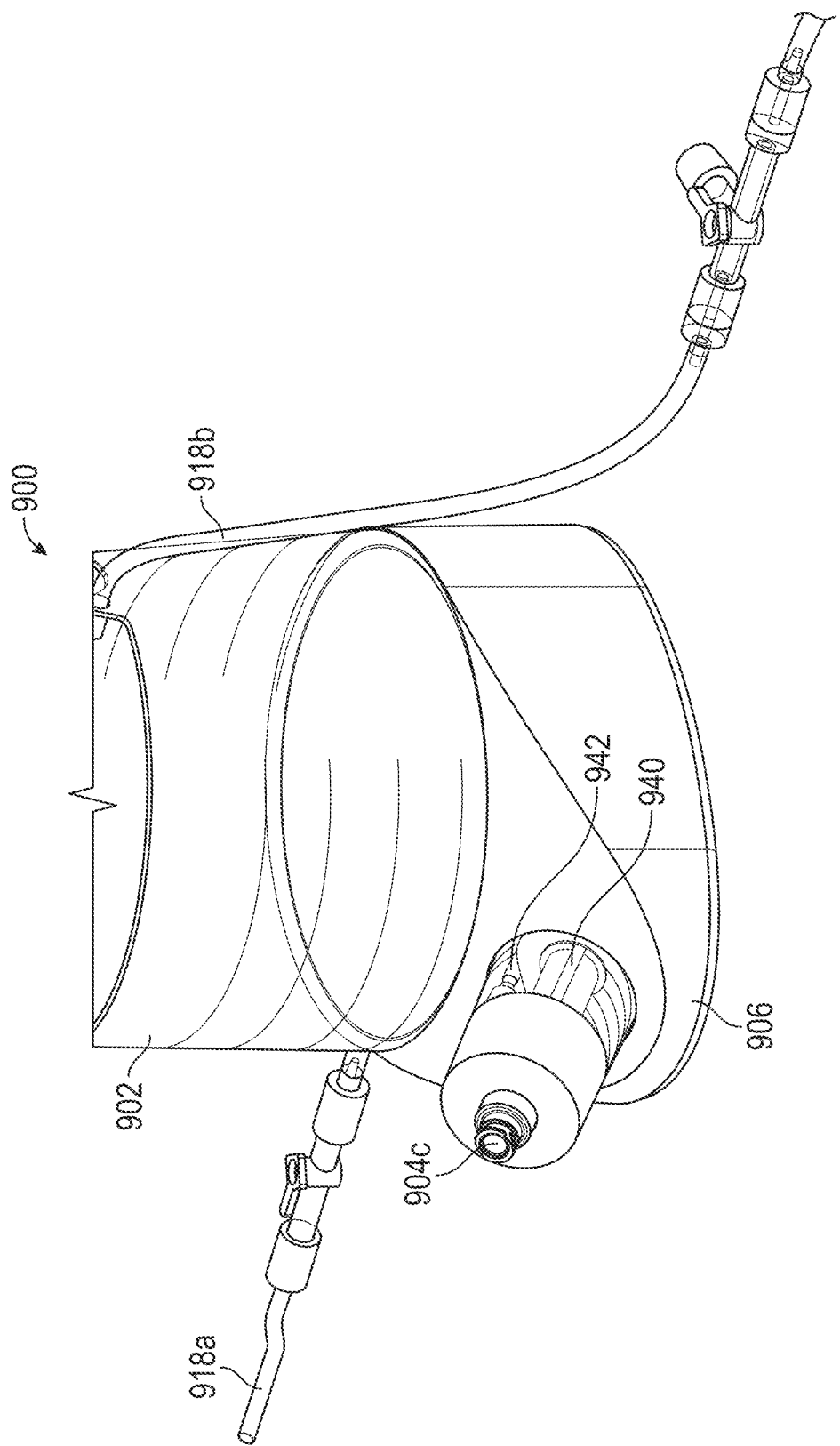

FIGS. 18A-18B show another example of a blood reintroduction system. Like the blood reintroduction systems 600, 700, and 800, the blood reintroduction system 900 can include a canister 902, an inlet 904a, a first outlet 904b, a second outlet 904c, and a base 906. The inlet 904a and the first outlet 904b can be connected to other medical devices via tubing. For example, a first aspiration tubing 918a can be connected to the inlet 904a, and a second aspiration tubing 918b can be connected to the first outlet 904b. The first aspiration tubing 918a can place the canister 902 and an aspiration system, such as aspiration system 100 (as described in relation to FIG. 1) in fluid communication with each other. Blood drawn into the canister 902 via the first aspiration tubing 918a can collect on a bottom portion of the canister 902. The second aspiration tubing 918b can place the canister 902 and an aspiration pump, such as aspiration pump 50 (as described in relation to FIGS. 1-8) in fluid communication with each other. The vacuum generated by the aspiration pump 50 can beneficially facilitate aspiration of blood from the first aspiration tubing 918a to the canister 902.

Like the blood reintroduction systems 600, 700, and 800, the blood reintroduction system 900 can include one or more filters. The one or more filters can be positioned upstream of the second outlet 904c, at the second outlet 904c, at a syringe 920, and/or along a flow path (e.g., a venous line between the second outlet 904c and the patient) before reinfusion of the fluid (e.g., blood) to the patient. In some cases, the one or more filters can be positioned between an opening of the second outlet 904c and an internal space of the canister 902. For example, the blood reintroduction system 900 can include a filter 940. Unlike the filters 640, 740, and 840, of the blood reintroduction systems 600, 700, and 800, the filter 940 of the blood reintroduction system 900 can be positioned outside the canister 902. For example, the filter 940 can be positioned inside a canister connector 942. The canister connector 942 can extend from the base 906. The canister connector 942 can include a window 942a, such as a transparent side wall, to permit visualization of any debris trapped on an upstream surface of the filter membrane. In some cases, a shape and/or dimensions of the canister connector 942 are larger than a shape and/or dimensions of the filter 940 to allow the canister connector 942 to receive and secure the filter 940. The filter 940 can prevent solid matter, such as thrombus, collected inside the canister 902 from reaching the second outlet 904c. This can beneficially prevent solid matter from being extracted via the second outlet 904c using an extraction device, such as the syringe 920. The filter 940 can trap solid matter while allowing fluids, such as fluid (e.g., blood), to flow past the filter 940.

In some cases, a longitudinal axis L4 of the second outlet 904c and/or the canister connector 942, and the base 606 can form an angle A4, as shown in FIG. 18B. Like the angle A1 of the blood reintroduction system 600, the angle A4 of the blood reintroduction system 900 can be between about 10° and about 80°. For example, the angle A4 can be between about 10° and about 40°, between about 20° and about 50°, between about 30° and about 60°, between about 40° and about 70°, or between about 50° and about 80°.

Figure 19A:
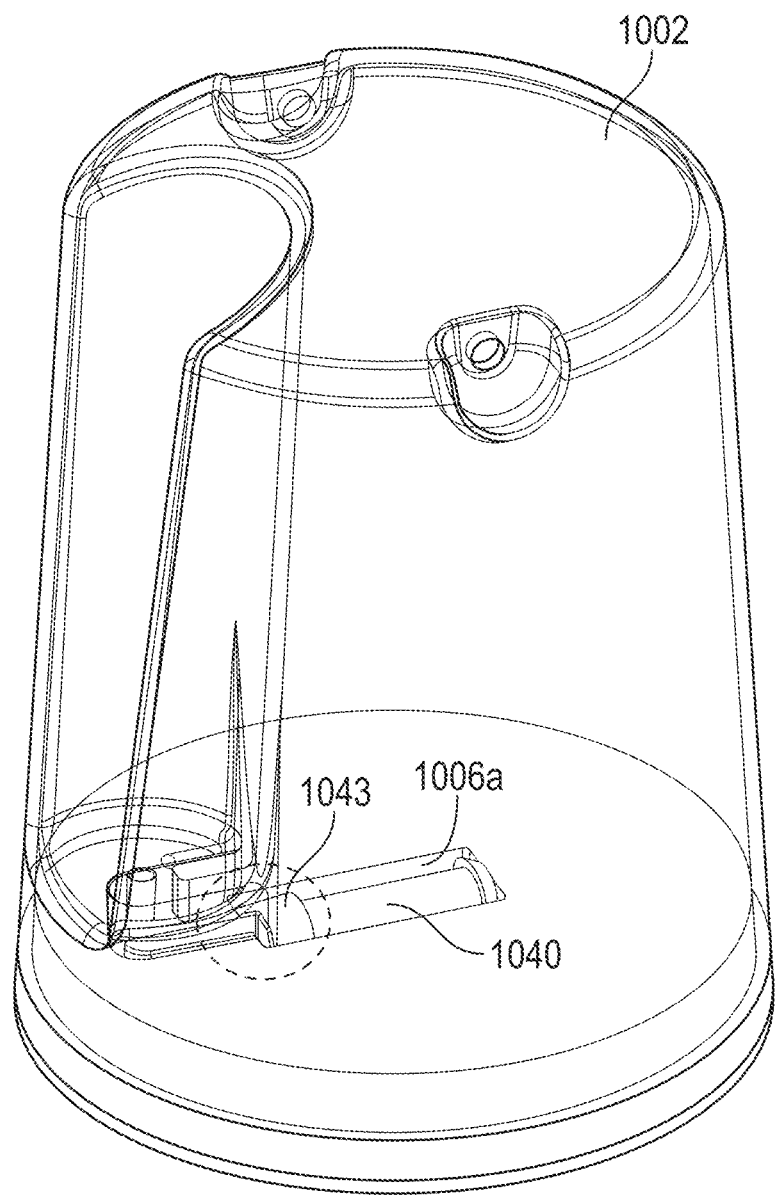
FIG. 19A shows an example of a canister for use with a blood reintroduction system.
Figure 19B:
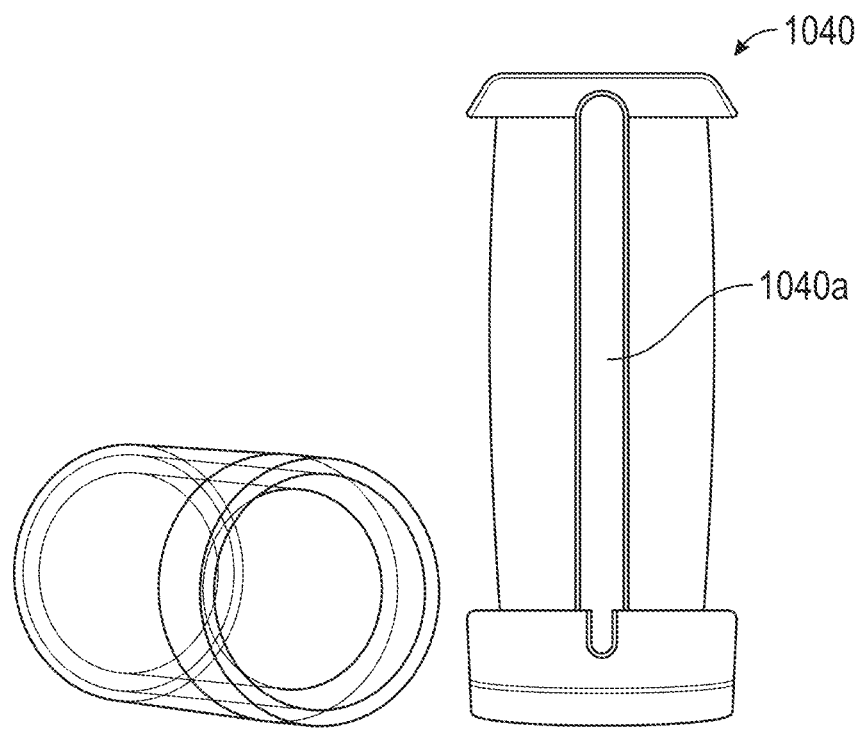
FIG. 19B shows an example of a filter for use with a blood recirculation system.
Figure 19C:
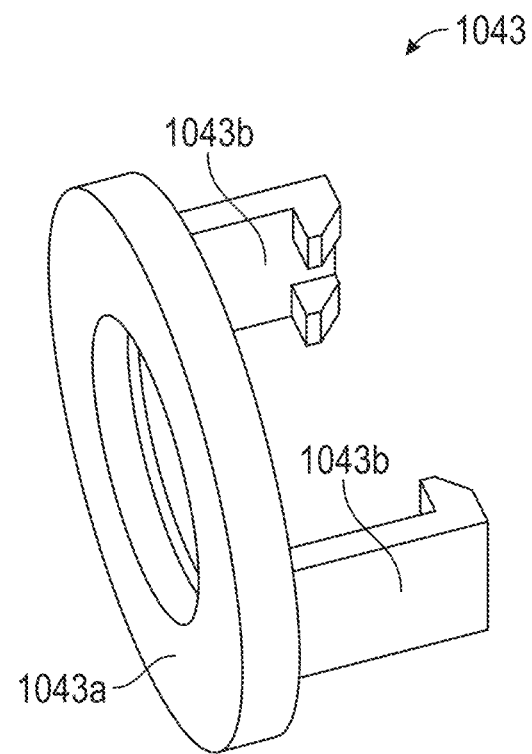
FIG. 19C shows an example of a filter lock for use with a filter and a blood recirculation system.

FIG. 19A shows an example of a canister 1002 for use with a blood reintroduction system (e.g., blood reintroduction systems 600, 700, 800, 900). A securing mechanism can be used to secure a filter, such as filters 640, 740, 840, inside a canister. For example, a filter lock 1043 can be used to secure a filter 1040, which is shown in FIG. 19B and which can be identical or similar to filters 640, 740, 840, and/or 940), inside the cavity 1006a. The filter 1040 an include a support element 1040a extending across a length of the filter 1040. The support element 1040 can beneficially prevent collapse of the filter when vacuum is applied. The filter 1040 can be a substantially planar porous membrane, or tubular (e.g., cylindrical) as shown in FIG. 19B, with an upstream surface on the outside and a downstream surface on the inside. The filter lock 1043 can include a cap 1043a and one or more arms 1043b extending from the cap, as shown in FIG. 19C. In some cases, the arms 1043b can extend from the cap 1043a perpendicularly. The cap 1043a can be secured to the cavity 1006a and the arms 1043b can secure the filter 1040. The filter lock 1043 can beneficially secure the filter 1040 inside the cavity 1006a and prevent the filter 1040 from moving inside the canister 1002.

Figure 20A:
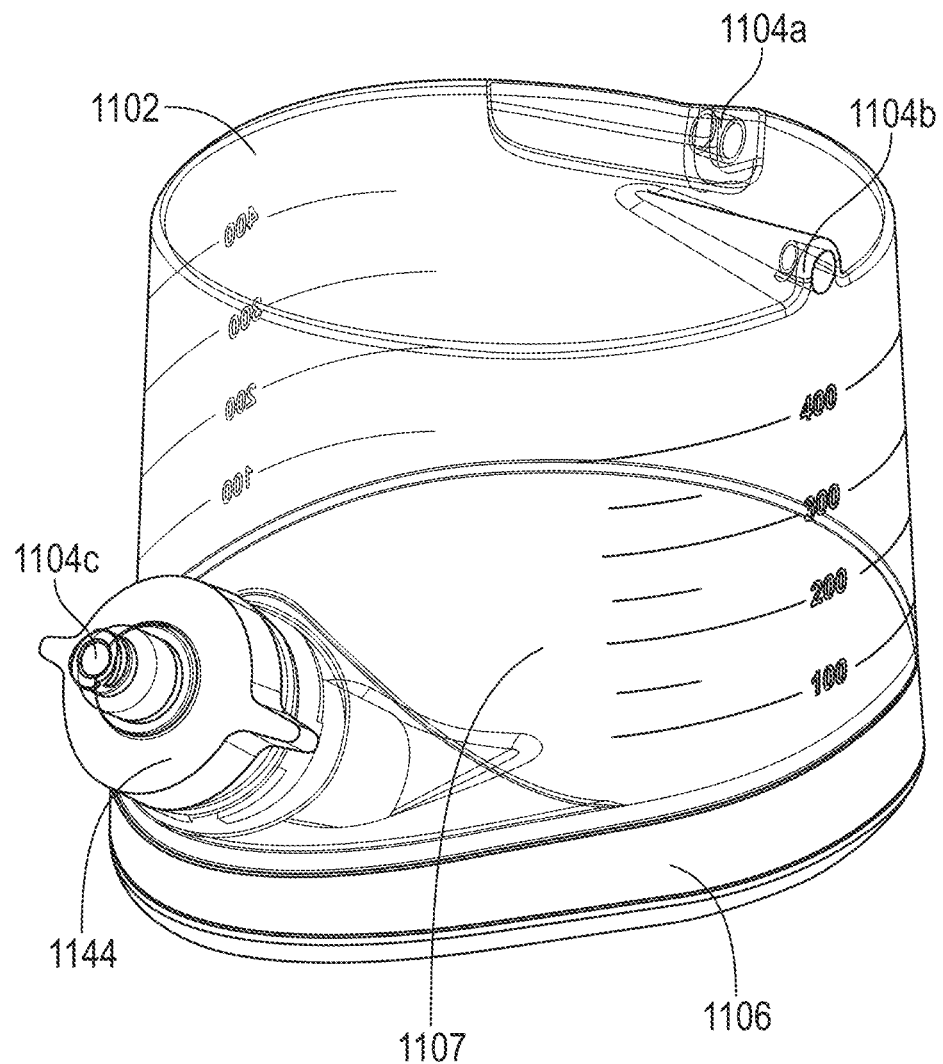
FIGS. 20A-20C show an example of a canister for use with a blood reintroduction system.
Figure 20B:
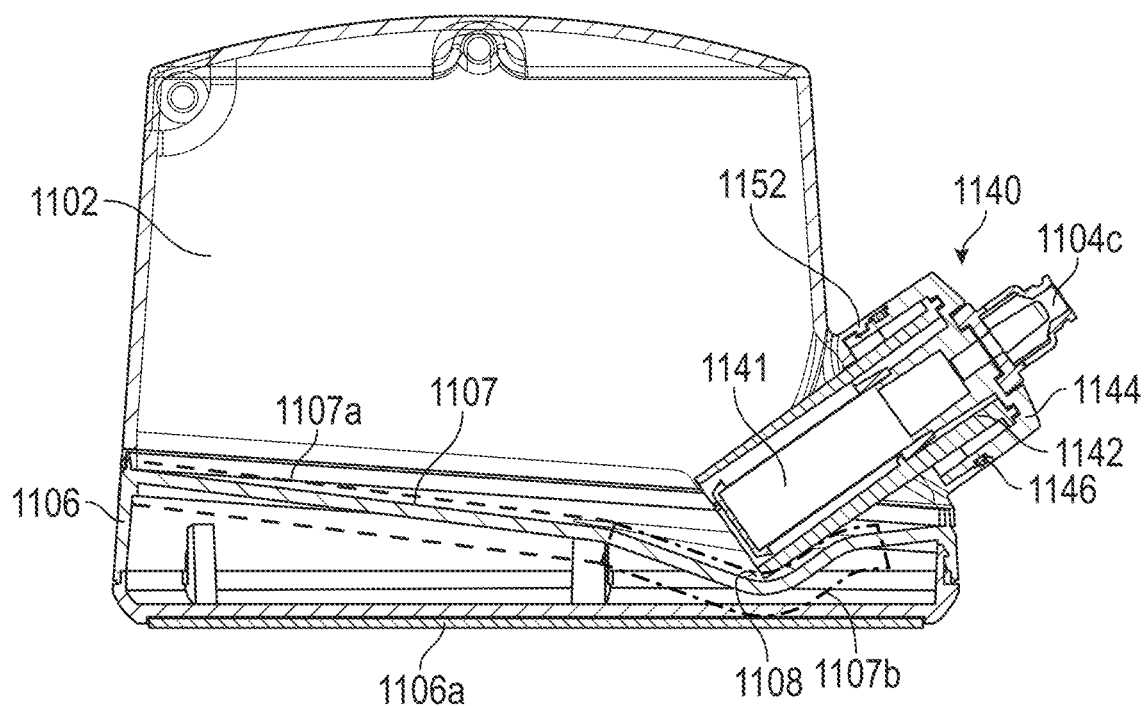
Figure 20C:
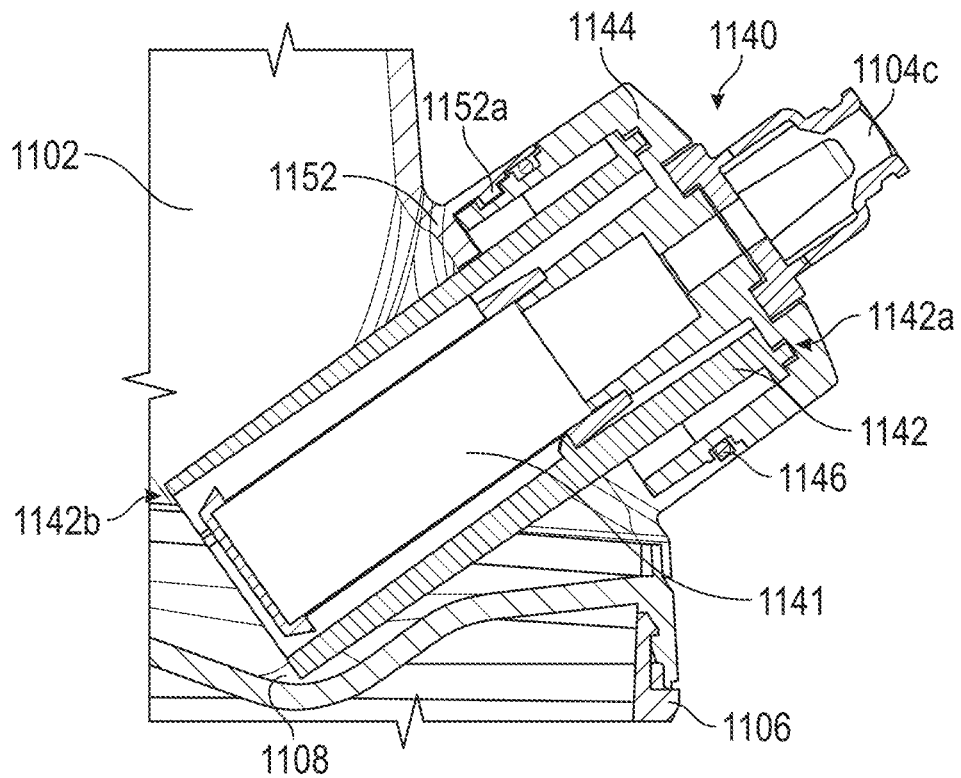
Figure 21A:
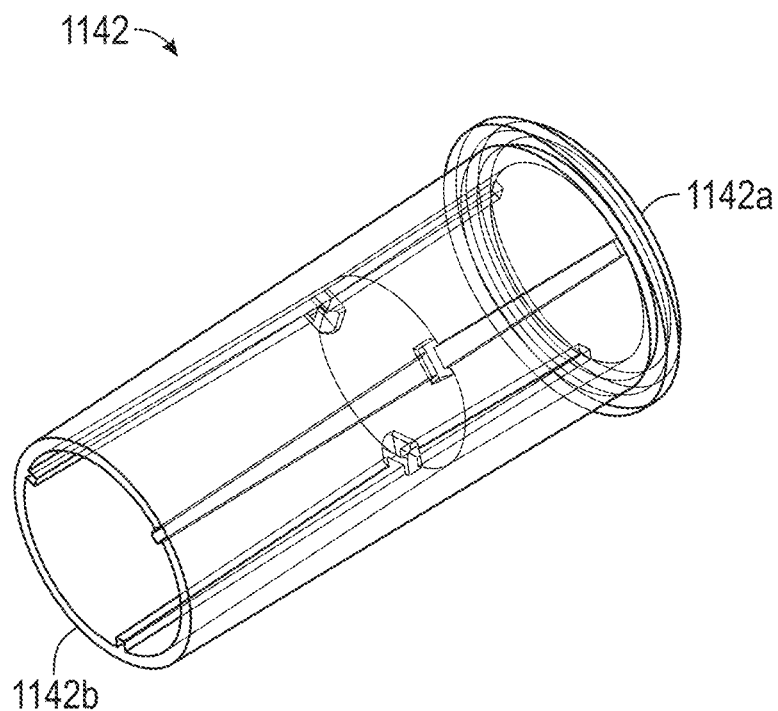
FIGS. 21A-21B show an example of a filter housing for use in a filter assembly.
Figure 21B:
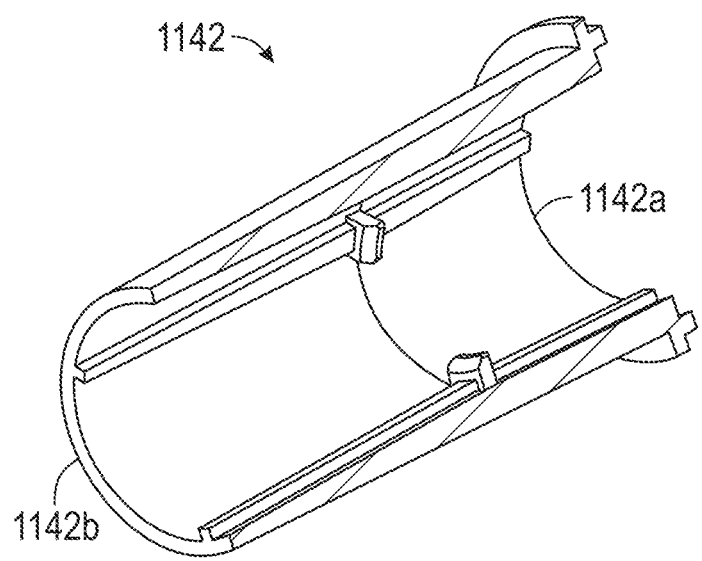

FIGS. 20A-20C show another example of a canister 1102. The canister 1102 can be used, for example, in a blood reintroduction system, such as blood reintroduction systems 600, 700, 800, 900, 100 which are described in relation to FIGS. 15A-18B. The canister 1102 can include an inlet 1104a, a first outlet 1104b, a second outlet 1104c, all in communication with a chamber defined by the canister 1102, and a base 1106. In some cases, the base 1106 can form a floor 1107 exposed to an interior volume of the canister 1102. In some cases, the floor 1107 can include one or more portions. For example, the floor 1107 can include a first portion 1107a and a second portion 1107b. The first portion 1107a can be inclined to facilitate flowing of the fluids (e.g., blood) collected inside the canister 1102 towards the second portion 1107b. The second portion 1107b may be the lowest point in the enclosed volume of the canister 1102 and can define a dip 1108. In some cases, a lower portion 1106a of the base 1106 can include a friction enhancing surface structure and/or material to prevent the canister 1102 from moving and-or slipping. The lower portion 1106a can include a silicone rubber coating, layer, and or feet which can beneficially provide a gripping surface.

A filter assembly 1140 is carried by and can be positioned at least partially inside the canister 1102. For example, the filter assembly 1140 can be positioned inside a canister connector 1152 at least partially formed by the canister 1102. In some cases, the canister connector 1152 can extend from the canister 1102. The base 1106 and the canister connector 1152 can form an acute angle similar or identical to angels A1 and/or A4, which are described in relation to FIGS. 15C and 18B respectively. As shown in FIGS. 21A-22B, the filter assembly 1140 can include a filter housing 1142 and a cap 1144. The filter housing 1142 can include a proximal end 1142a and a distal end 1142b. The cap 1144 can be attached to the proximal end 1142a of the filter housing 1142. In some cases, the cap 1144 can be attached to the filter housing 1142 using a threaded engagement or adhesive.

The filter assembly 1140 can also include a filter 1141. The filter 1141 can be positioned inside the filter housing 1142, as shown in FIGS. 20A and 20B. The filter 1141 can include a membrane including a 10, 15, 20, 30, 40, 50, 100, and/or a 200-micron rating. The filter can include a membrane including a rating of at least 100 microns. In some cases, the filter 1141 includes a cylindrical side wall defining a hollow interior. The filter 1141 can include a membrane wrapped around the hollow center of the cylindrical scaffold.

Figure 22A:
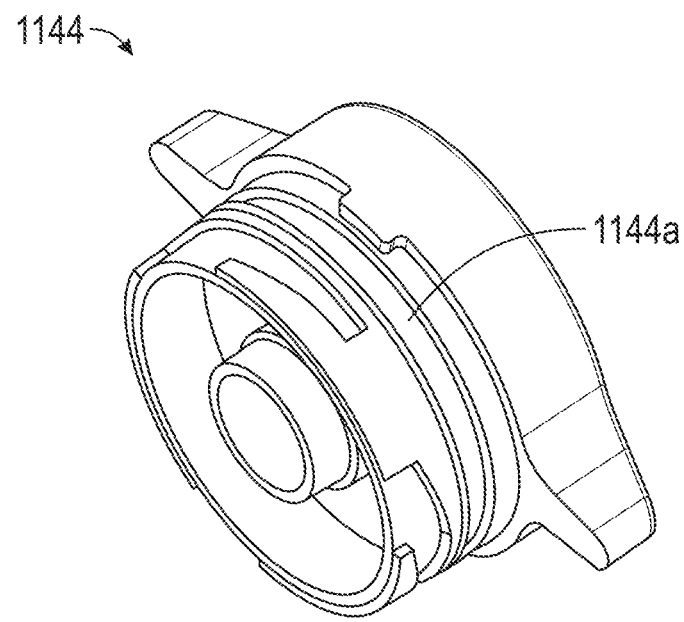
FIGS. 22A-22B show an example of a cap for use in a filter assembly.
Figure 22B:
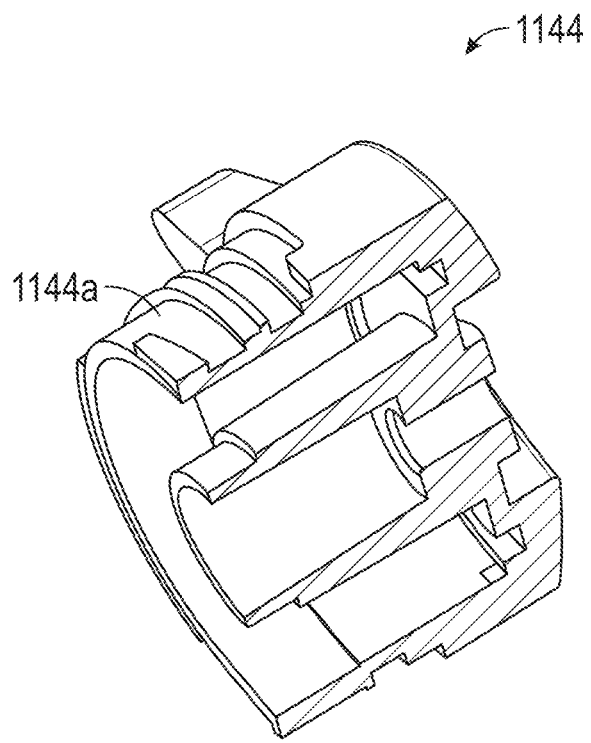
Figure 22C:
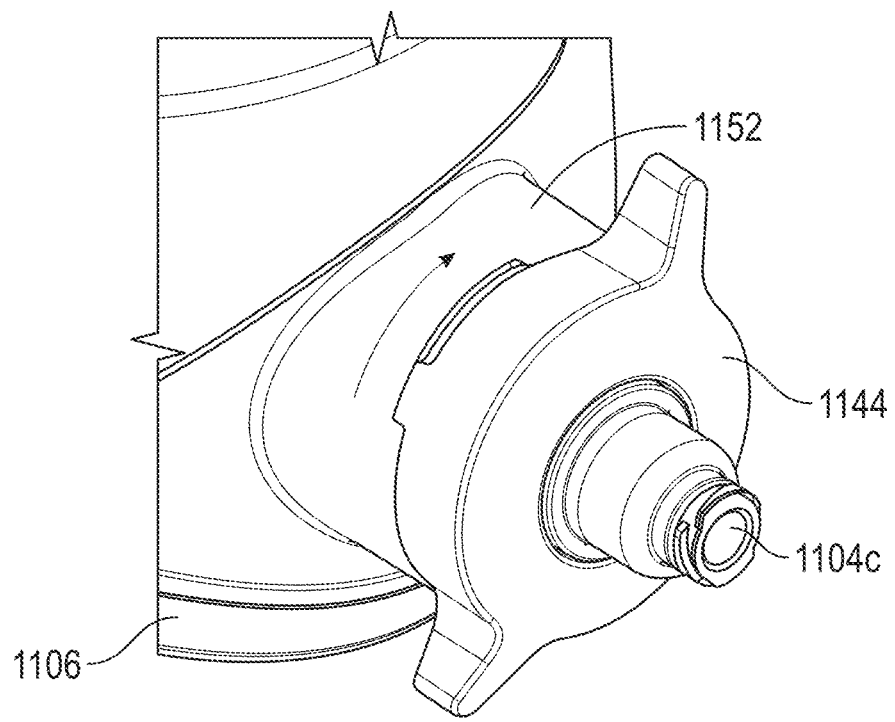
FIGS. 22C-23 show the cap shown in FIGS. 22A-22B attached to a canister.
Figure 22D:
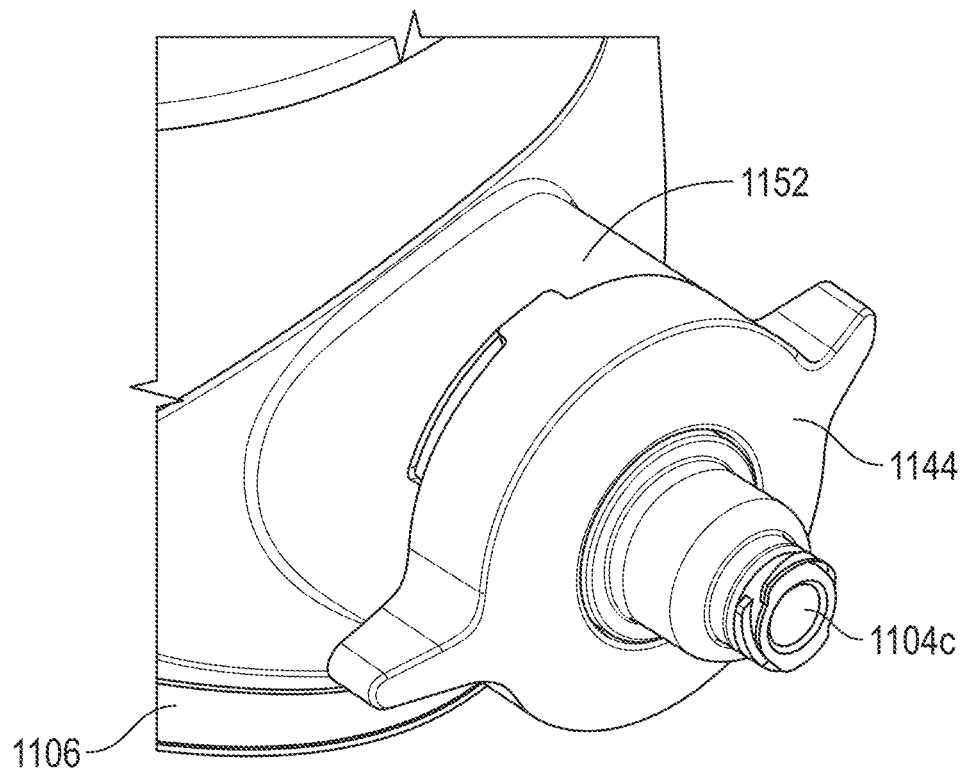
Figure 23:
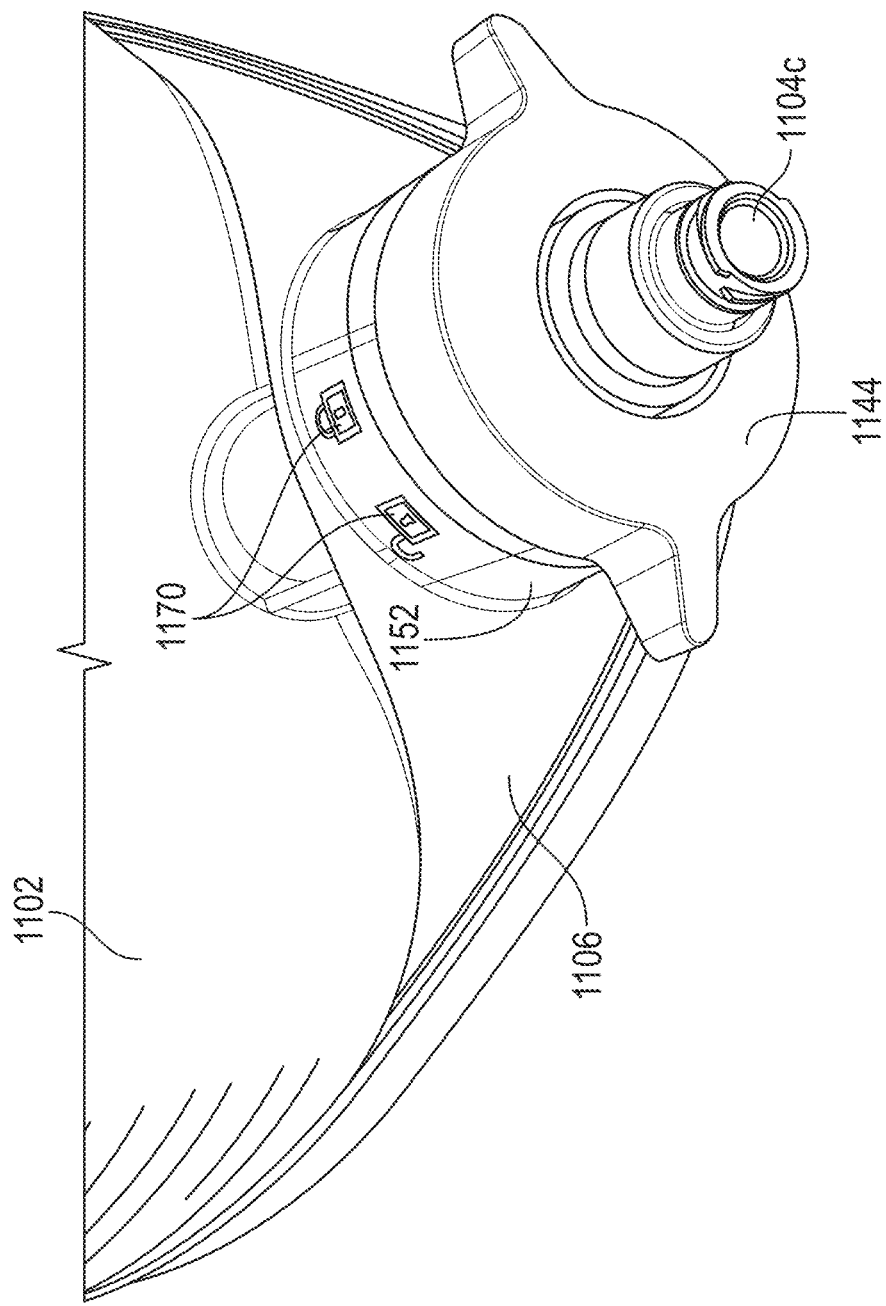

The cap 1144 can include a thread 1144a, as shown in FIGS. 22A and 22B, which can facilitate attachment of the filter assembly 1140 to the canister connector 1152. An exterior portion of the canister connector 1152 can include a thread 1152a. The thread 1152a can receive the thread 1144a of the cap 1144 thus securing the cap 1144 to the canister connector 1152. The cap 1144 can be secured to the canister connector 1152 by, for example, rotating the cap 1144 from a first, unlocked position, as shown in FIG. 22C, to a second, locked position, as shown in FIG. 22D, thereby securing the threads 1152a, 1144a to each other. An O-ring 1146 can be positioned between the cap 1144 and the canister connecter 1152 to create a seal between the cap 1144 and the canister connecter 1152 when the cap 1144 is secured to the canister connector 1152. In some cases, the canister connector 1152 and/or the cap 1144 can include one or more visual and/or tactile elements 1170, as shown in FIG. 23, for indicating whether the cap 1144 is in the unlocked position (e.g., not secured to the canister connector 1152) and/or a locked position (e.g., secured to the canister connector 1152).

While the cap 1144 and the canister connector 1152 are illustrated with a threaded interlocking system, it will be understood that the cap 1144 and the canister connector 1152 may incorporate any suitable interlocking mechanism (e.g., an adhesive, snap-fit, interference fit, etc.) to engage the cap 1144 with the canister connector 1152. The interlocking mechanism can beneficially allow physicians and/or users to remove and replace the filter assembly 1140 and/or the filter 1141 if, for example, the filter 1141 gets clogged during use.

In some cases, the second outlet 1104c can include a valve such as a luer fitting. The second luer fitting can be secured to the cap 1144. Blood can be extracted from the canister 1102 via the luer fitting using an extraction device such as a syringe. The syringe can be similar or identical to syringes 620, and/or 920. The filter 1141 can prevent solid matter, such as thrombus, collected inside the canister 1102 from reaching the luer fitting. This can beneficially prevent solid matter from being extracted via the luer fitting using the extraction device. The filter 1141 can trap solid matter while allowing fluids (e.g., blood), to flow through the filter 1141 and into the extraction device.

In embodiments where the second outlet 1104c includes a luer fitting, the luer fitting can allow the second outlet 1104c to receive and secure other luer fitting. For instance, a syringe with a luer fitting can be connected and secured to the luer fitting of the second outlet 1104c. The luer fitting can beneficially allow for the precise control of withdrawal of fluids from the canister 1102. The luer fitting can also provide a secure connection to the syringe and/or tubing and prevent leaks at the second outlet 1104c. The luer fitting can include different sizes and dimensions to accommodate different syringes and/or tubing.

The filter 1141 allows absorption of fluids and extraction of the fluids using the extraction device (e.g., syringe) when the filter 1141 is in fluid contact with the fluids inside the canister 1102. To improve and maintain contact between the filter 1141 and the fluids collected inside the canister 1102, the distal end 1142b of the filter housing 1142 and the distal end of the filter 1141 can positioned at least partially in the low spot such as dip 1108 formed by the second portion 1107b of the floor 1107. The inclined surface of the first portion 1107a can facilitate flow of the fluids toward the dip 1108 formed by the second portion 1107b and allow the distal tip of the filter 1141 to contact the bottom-most part of the floor 1107. This can beneficially enhance contact between the distal tip of the filter 1141 and the fluids, thus allowing extraction of the fluids using the extraction device and preventing users from extracting air. The inclined first portion 1107a can allow any blood inside the canister 1102 to be immediately directed towards the dip 1108 where the filter 1141 is closest to the floor 1107.

A bottom edge of the filter 1141 can be transverse to a longitudinal axis of the filter housing 1142. In some cases, once the filter 1141 gets wet (e.g., the filter 1141 contacts the blood collected inside the canister 1102), it can absorb the blood collected in the canister 1102. This can beneficially allow the extraction device, such as a syringe, to withdraw blood from the filter 1141 even when only a portion of the filter 1141 is in contact with the blood inside the canister 1102. The proximity of the distal end of the filter 1141 to the dip 1108 reduces the amount of blood required for the filter 1141 to first contact the blood. In some cases, as little as 50 cc of blood may collect inside the dip 1108 before the blood contacts the distal end of the filter 1141.

A flow path extending between the dip 1108 and the second outlet 1104c can allow blood to collected at or near the dip 1108, flow through the filter 1141, and exit the canister 1102 via the second outlet 1104c. Physicians and/or users can extract blood from the canister 1102 using the syringe as long as any part of the filter 1141 is in contact with the blood collected in the dip 1108. The syringe can draw the blood absorbed by the filter 1141 through the sidewalls of the filter 1141 until the blood is drawn into the syringe via the second outlet 1104c. As blood is withdrawn using the syringe, any remaining blood inside the canister 1102 can flow to the dip 1108 where it can be absorbed by the filter 1141 and/or subsequently withdrawn using the syringe. This can beneficially prevent the blood from settling inside a portion of the canister 1102 where the blood may be prevented from being withdrawn using the syringe.

In any of the embodiments disclosed herein, blood can flow into the canister 1102 through an inlet aligned a top portion of the canister 1102. The blood can wash along the sidewall of the canister 1102. This can allow physicians and/or users to easily identify the presence of blood inside the canister 1102. The sidewalls of the canister 1102 can provide a smooth pathway (e.g., decrease sheer stress and/or improve laminar flow) for the blood to flow towards the floor 1107 which can beneficially prevent and/or decrease hemolysis. For example, the inlet 1104a can be oriented so that blood is directed to an interior of the sidewall of the canister 1102 as blood flows from the aspiration catheter into the canister 1102. This can allow a circumferential blood flow along the inter of sidewall. The circumferential blood flow can result in the blood flowing along the sidewall before eventually collecting on the floor 1107 of the canister 1107. The circumferential blood flow can beneficially minimize turbulence and/or splashes. In some cases, the flow of blood exiting the inlet 1104a can form a tangent relative to the interior of the sidewall.

Figure 2B:
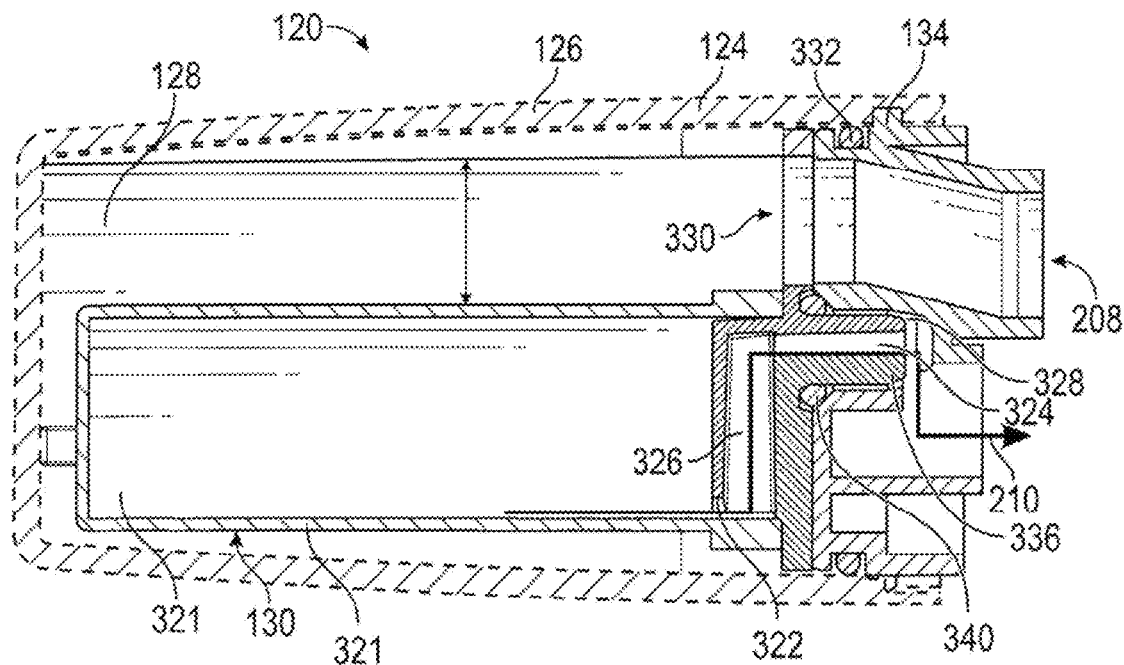
FIGS. 2B-2E illustrate interface details between a filter assembly and a proximal handle.
Figure 2C:
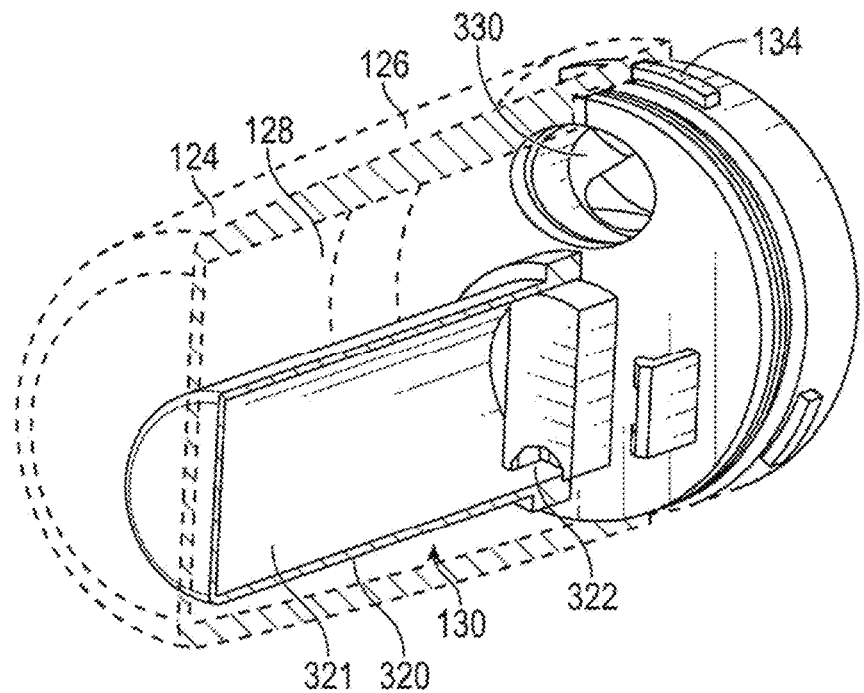

Additional details of the filter assembly and related structures are illustrated in FIGS. 2B to 2E. Referring to FIG. 2B, the filter assembly 120 includes a tubular sidewall 124 having a transparent window 126. In some implementations the entire tubular sidewall 124 can be a transparent window. The side wall 124 encloses a filter 130 as has been discussed. The filter 130 includes a tubular filter sidewall 320 defining an interior chamber 321 for filtered blood. Filtered blood is drawn in the direction of vacuum line 210 through a first vacuum aperture 322 and into a flow path 324 having a vertical offset 326 in the flow path 324. The vertical offset 326 allows removal of blood from the bottom of the chamber, through a flow path and out through a second vacuum aperture more centralized with respect to a central axis of the tubular sidewall 124 and in communication with vacuum line 210.

The filter 130 is displaced downward with respect to a central longitudinal axis of the tubular sidewall 124, leaving the filter chamber 128 having a chamber height 129 at least as great as the inside diameter of a filter line aperture 330 leading to filter line 208. This allows clot to move from filter line 208 into the filter chamber 128 without restriction, and optimizes the volume of filter chamber 128 on top of the filter 130 for viewing through the window 126.

A connector 134 may be carried by the filter assembly 120, such as in the form of a bayonet mount, or other releasable attachment to the proximal handle housing. A first seal 332 such as an annular elastomeric ring may be provided between the tubular sidewall 124 and the complementary surface on the proximal handle housing.

A second vacuum aperture 328 is in communication with the first vacuum aperture 322 by way of the flow path 324. Second vacuum aperture 328 may be carried on an axially extending tubular projection 336 which may be removably received within a complementary recess on the proximal handle housing.

A second seal 340 such as an elastomeric ring may be provided surrounding the flow path 324, for providing a seal between the filter assembly and the proximal handle. In the illustrated implementation, the second seal 340 surrounds the tubular projection 336 and is configured to seal against an adjacent complementary surface on the proximal handle in the as mounted orientation.

Figure 2D:
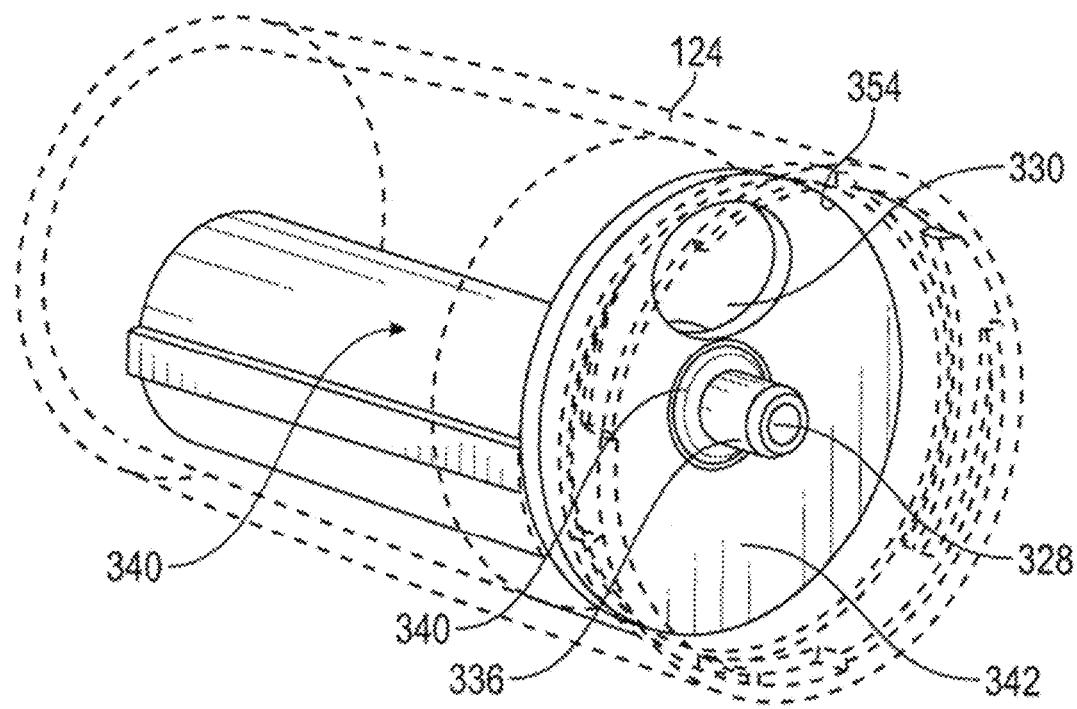
Figure 2E:
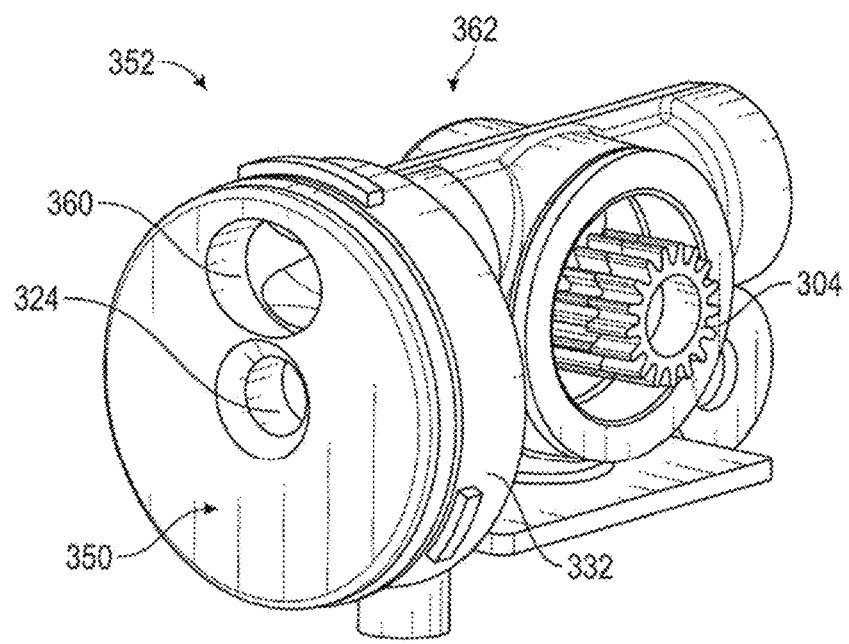

Referring to FIG. 2D, the filter assembly 120 additionally includes a filter base 342 through which filter line aperture 330 extends. The flow path 324 additionally extends through the filter base 342, and, in the illustrated implementation, exits the tubular projection 336 carrying the second vacuum aperture 328.

A complementary docking platform 350 is carried by the proximal handle, having complementary connector to connector 134 for rapid attachment and detachment of the filter assembly 120 from the proximal handle. In the illustrated embodiment, at least a first flange 352 may be received through an opening 354 on the filter assembly 120. Rotation of the filter assembly 120 moves the first flange into interference fit with a second flange 356 to secure the filter assembly 120 to the docking platform 350 on the proximal handle. Two or three or four or more similar flange and complementary opening pairs may be provided around the periphery of the components. In the illustrated implementation, the circumferential arc length of the flange and corresponding opening on one of the three pairs is greater than the other two pairs to function as a key, so that the filter assembly can only be secured to the docking platform in a single rotational orientation.

The docking platform 350 includes a filter line aperture 360 for communicating with filter line 208, and a vacuum line aperture 362 for placing the filter 130 in communication with a source of vacuum. The docking platform 350 may be connected to a two way valve 362 or a three way valve as is discussed elsewhere herein depending upon the desired functionality. The valve may carry a rotatable drive gear 304 to rotate the interior rotatable valve gate as is discussed in additional detail below. Alternatively, a lever or other control on the housing may be configured to rotate a shaft directly coupled to the rotatable part of the valve.

A valved flow path may also be provided for venting the filter chamber 128 directly to atmosphere. The valve may be opened such as by depressing a momentary button, which is biased in the closed direction. This can create an abrupt change in pressure at the distal end of the catheter, which may facilitate clot aspiration. This can also be used to discharge vacuum Referring to FIG. 3A, additional details of the handle 140 of the second catheter 104 are disclosed. The handle 140 extends between a proximal end and a distal end. An elongate flexible tubular body 152 extends distally from the distal end of the handle 140 and is configured to advance distally through the proximal handle 106 and the tubular body 108 of thrombectomy catheter 102.

A steering dial 144 may be provided to place one or more steering wires under tension, to deflect a deflection zone near the distal end of the tubular body 152. A manifold switch 116 may be provided to control the flow of fluid as will be discussed below. The handle additionally comprises an aspiration control 117 such as a slider switch, for turning aspiration on or off. A max button 132 may be provided for delivering a momentary pulse of high aspiration rate as has been discussed.

Figure 4:
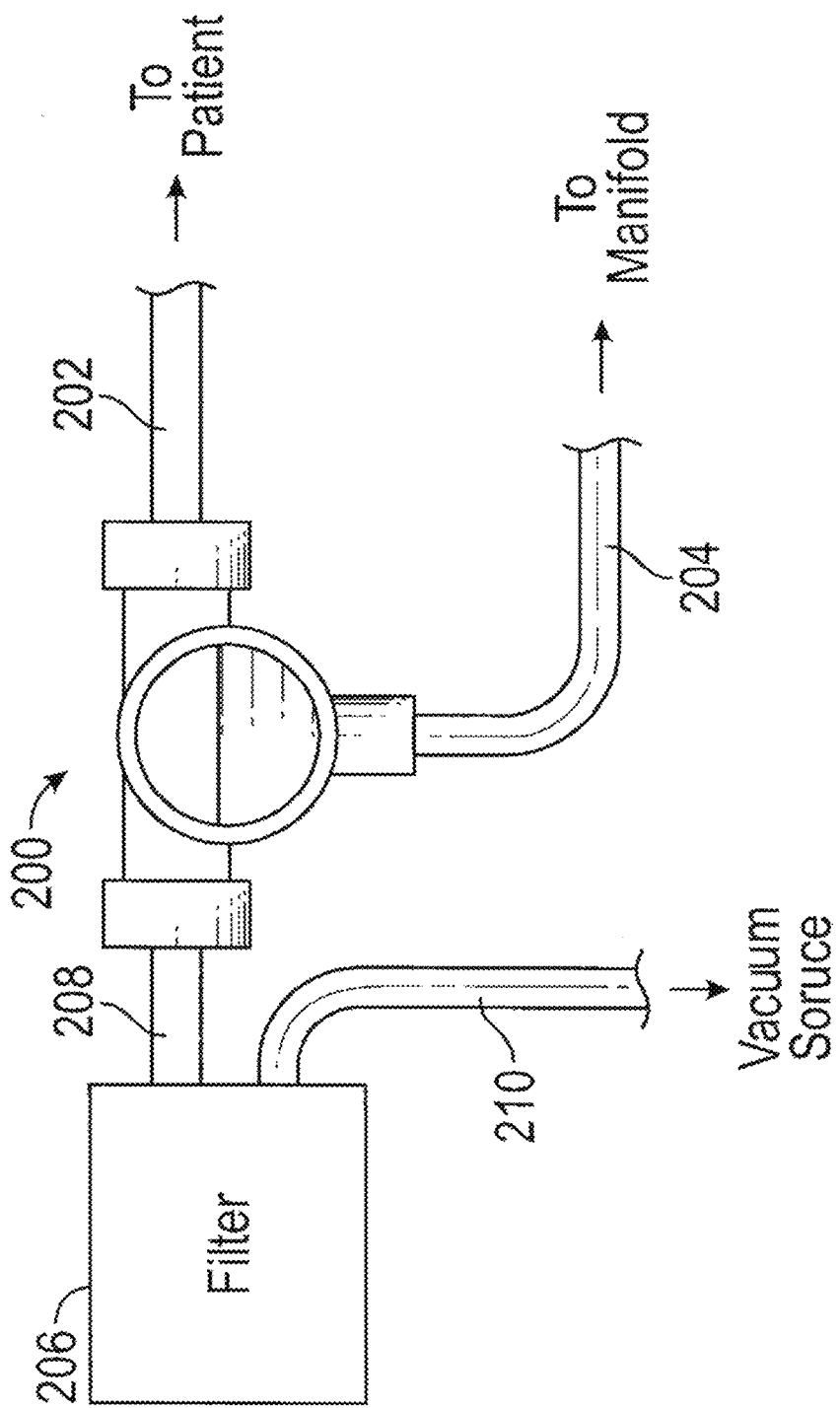
FIG. 4 is a schematic flow diagram for a three-way valve.

Fluid flow through the thrombectomy system is controlled by manifold switch 116 (see, e.g., FIG. 1), which may control a two way or three-way valve. Referring to FIG. 4, a schematic flow diagram for three-way valve 200 is provided. Patient line 202 can be placed in fluid communication with the patient, via a catheter such as a large diameter thrombectomy catheter 12 or second catheter 42.

Patient line 202 may be placed in communication with a manifold line 204 by advancing the three-way valve 200 to a first position, such as to allow delivery of medications, contrast media or saline to the patient.

Adjustment of the three-way valve 200 to a second position can isolate patient line 202 and place the manifold in communication with the filter 206 via filter line 208. Activation of a vacuum pump will draw blood from the patient and through the filter 206 via vacuum line 210.

Further adjustment of the three-way valve 200 to a third position will place the manifold in communication with the vacuum line 210, such as to permit a saline flush of the filter 206. This third position may be eliminated depending upon the desired functionality.

Figure 5A:
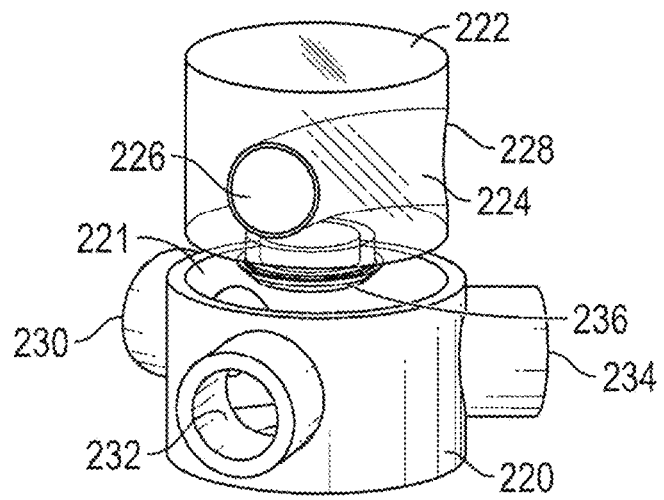
FIGS. 5A-5C illustrate three flow configurations for a three-way valve.
Figure 5B:
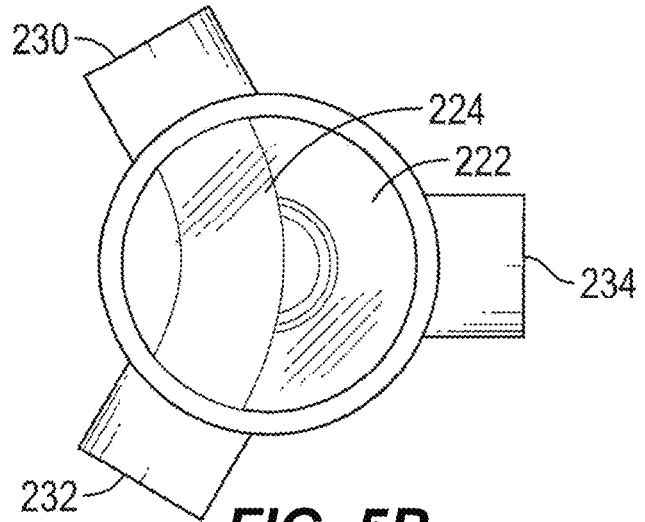
Figure 5C:
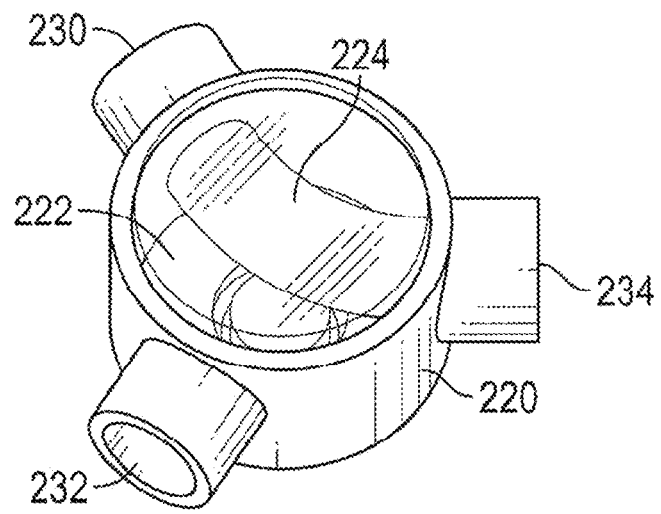

One implementation of a suitable three-way valve 200 is illustrated in FIGS. 5A through 5C. Referring to FIG. 5A, the valve 200 may comprise a housing 220 such as a cylindrical housing having a central cavity 221. A rotatable cylindrical gate 222 may be positioned in the central cavity 221, as illustrated in the exploded view of FIG. 5A. Rotatable gate 222 is provided with a flow path 224 extending between a first end 226 and a second end 228. In the illustrated implementation, the first end 226 and a second end 228 of the flow path are spaced apart around the circumference of the rotatable gate by approximately 120 degrees.

In the rotational orientation of the rotatable gate 222 illustrated in FIG. 5A, the first end 226 of the flow path 224 is in communication with a first port 232, and the second end 228 of the flow path 224 is in communication with a second port 234. This corresponds to the first position discussed previously, in which the patient is in fluid communication with the manifold.

FIG. 5B illustrates rotatable gate 222 in the second position where the flow path 224 places the first port 232 in communication with the third port 230 to place the filter 206 in communication with the manifold. The rotatable gate 222 may be toleranced within the cavity 221 such that the rotatable gate 222 seals the second port 234 thus isolating the patient from the flow path in this orientation. Similarly, in each of the other two orientations, two of the ports are placed in communication with the flow path, while the third port is isolated from the flow path.

The third position is illustrated in FIG. 5C, in which the flow path places the second port 234 in communication with the third port 230, placing the filter 206 in communication with the patient, and isolating the manifold from the flow circuit.

The foregoing selectivity may be achieved by spacing the three ports approximately 120 degrees apart around the circumference of the housing, to cooperate with the flow channel 224 end ports which are about 120 degrees apart around the circumference of the cylindrical gate 222. The gate 222 may be rotated within the housing 220 by a connector 236 extending through the housing 220 such as along the axis of rotation, and connected to a control 116 such as a rotatable knob, lever or slider switch with a rack and pinion drive assembly.

Each of the catheters disclose herein may be provided with a hemostasis valve on the proximal end, to allow selective closing of the central lumen to completely closed without any devices extending therethrough, from a sealed fit around devices of differing diameters such as a guide wire or a secondary catheter extending therethrough. One example of a suitable hemostasis valve is schematically illustrated in FIGS. 6A through 6C.

Figure 6A:
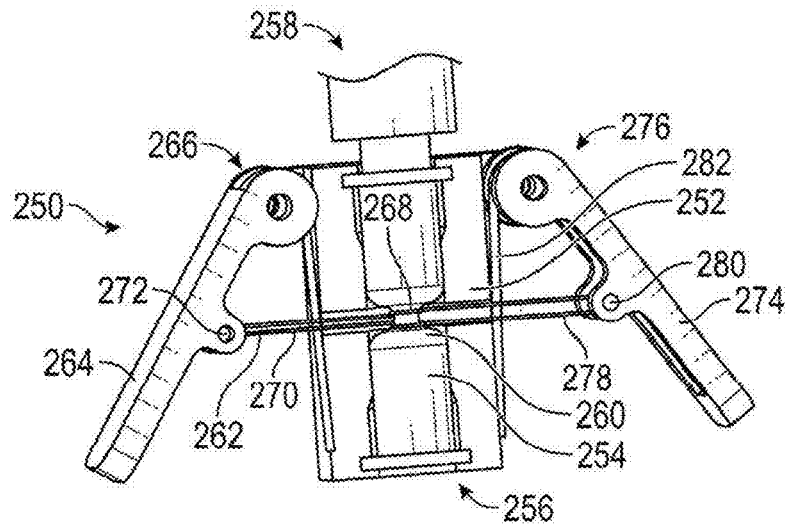
FIGS. 6A-6C illustrate operation of a hemostasis valve.
Figure 6B:
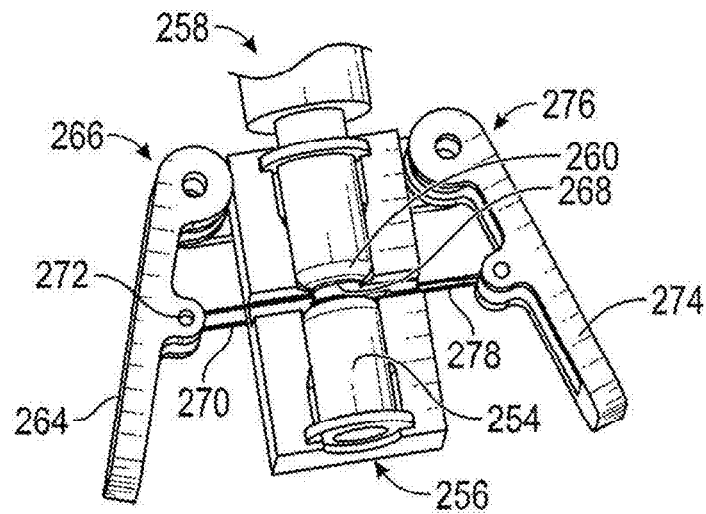
Figure 6C:
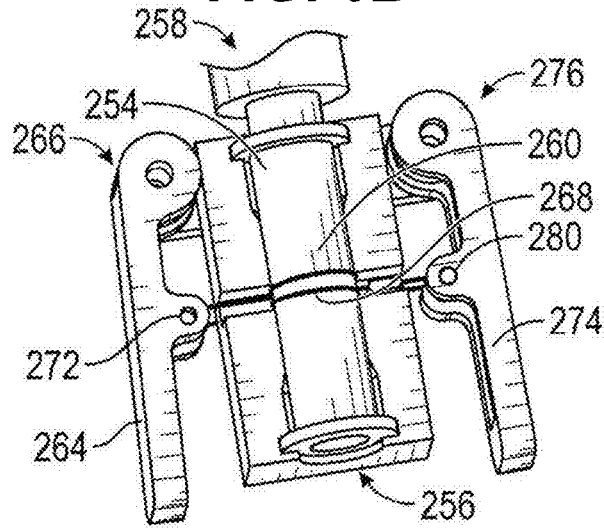
Figure 6D:
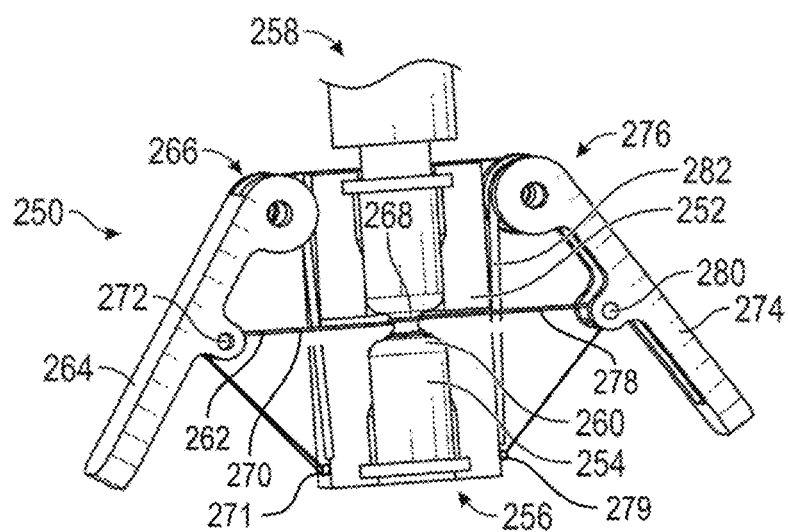
FIG. 6D illustrates an alternative filament configuration of the hemostasis valve.

Referring to FIG. 6A, hemostasis valve 250 includes a frame 252 for supporting a flow path defined within a tubular sidewall 254. The frame 252 may be integrally formed with or mounted to the catheter handle or hub.

The flow path and tubular sidewall 254 extend between a first end 256 and a second end 258. First end 256 may be a port 112 (see, e.g., FIG. 1) on the proximal end of any of the catheters disclosed herein. Second end 258 may be in communication with the central lumen of the corresponding aspiration catheter, such that devices entering the first end 256 and advanced axially through the flow path can advance all the way to the distal end of the aspiration catheter and beyond.

At least a portion 260 of the sidewall 254 is collapsible in response to external pressure. That portion 260 and optionally the full length of the tubular sidewall within valve 250 may be comprise a collapsible elastic tube such as silicone tubing, which is biased into an open lumen tubular configuration when unconstrained. A compression element such as filament 262 is configured to apply compressive force against the sidewall 254 to reduce the inside diameter of the flow path to provide a seal against itself (when completely closed with no devices extending therethrough) or against a device such as a guidewire or catheter extending therethrough. In the illustrated implementation, the filament 262 forms a loop 268 around the collapsible portion 260 of tubular sidewall 254. Retraction of a first tail portion 270 of the filament 262 away from the sidewall 254 constricts the diameter of the loop 268 thereby collapsing the portion 260 of the tubular sidewall as illustrated in FIG. 14 A.

In the illustrated implementation, the first tail portion 270 of the filament 262 may be retracted by at least a first lever 264. Lever 264 may be connected to the frame 252 by a first pivot 266 and is attached to the tail portion 270 at an attachment point 272. Advance of the lever in a first direction places the filament under tension and reduces the inside diameter of the valve. Releasing the lever removes the tension and the collapsible portion 260 of the sidewall rebounds to its unconstrained, open lumen configuration.

In the illustrated implementation, a second lever 274 is attached to the frame 252 at a second pivot 276, and is attached to a second tail portion 278 of the filament 262. Each of the first and second tail portions may comprise a single filament or two or three or more parallel filaments. In the two filament configuration as illustrated, the filaments may be immovably secured to the lever, or may be a continuous filament, looped around a fulcrum 280. The loop 268 may comprise one or two or three or more revolutions around the tubular sidewall, depending upon the desired performance.

At least one lever 264 is provided with a spring 282 to bias the lever away from the tubular sidewall, constricting the inside diameter of the collapsible portion 260 into sealing engagement with a device extending therethrough, or to a completely closed configuration in the absence of a device.

As illustrated, a second lever 274 may also be biased using the same spring or a second spring.

As illustrated in FIG. 6C, compression of the levers in a medial direction towards the axis of the tubular sidewall 254 releases tension on the tail portions of the filament and allows the valve to open, such as to permit advance of a catheter through the valve. Releasing the levers allows the spring bias to retract the tail portions, reducing the diameter of the loop 268 and collapsing the collapsible portion 260 into sealing engagement with the outside surface of the secondary catheter, at an intermediate valve diameter as seen in FIG. 6B.

Retraction of the tail portion 270 of filament 262 may alternatively be accomplished by winding the tail portion 270 around a rotatable spool such as a shaft or drum. Rotation of a knob or advance of a lever causes the spool to take up filament and collapse the sidewall.

An alternate configuration for the filament 262 is illustrated in FIG. 14 D. In this implementation, the first tail portion 270 slidably extends around a first fulcrum at 272 and returns to attach to the housing at an attachment point 271. First tail portion 270 extends from the fulcrum to form a loop 268 around the collapsible tube. The filament 262 may make a single revolution or two or more revolutions around the collapsible tube before continuing on around a second fulcrum at 280, to a second point of attachment 279 to the housing.

Compression of the first lever 264 and second lever 274 loosens the loop 268, allowing the lumen to resume patency. Releasing the levers allows the spring bias to reduce the diameter of the loop 268 as the first tail portion 270 and second tail portion 278 slide away from each other around the left and right fulcrums. Preferably, friction between the filament 262 and fulcrums are minimized, as by providing a lubricious oil such as silicone oil around the fulcrums at 280 and 272, as well as using Teflon braided line for the filament 262.

Figure 7A:
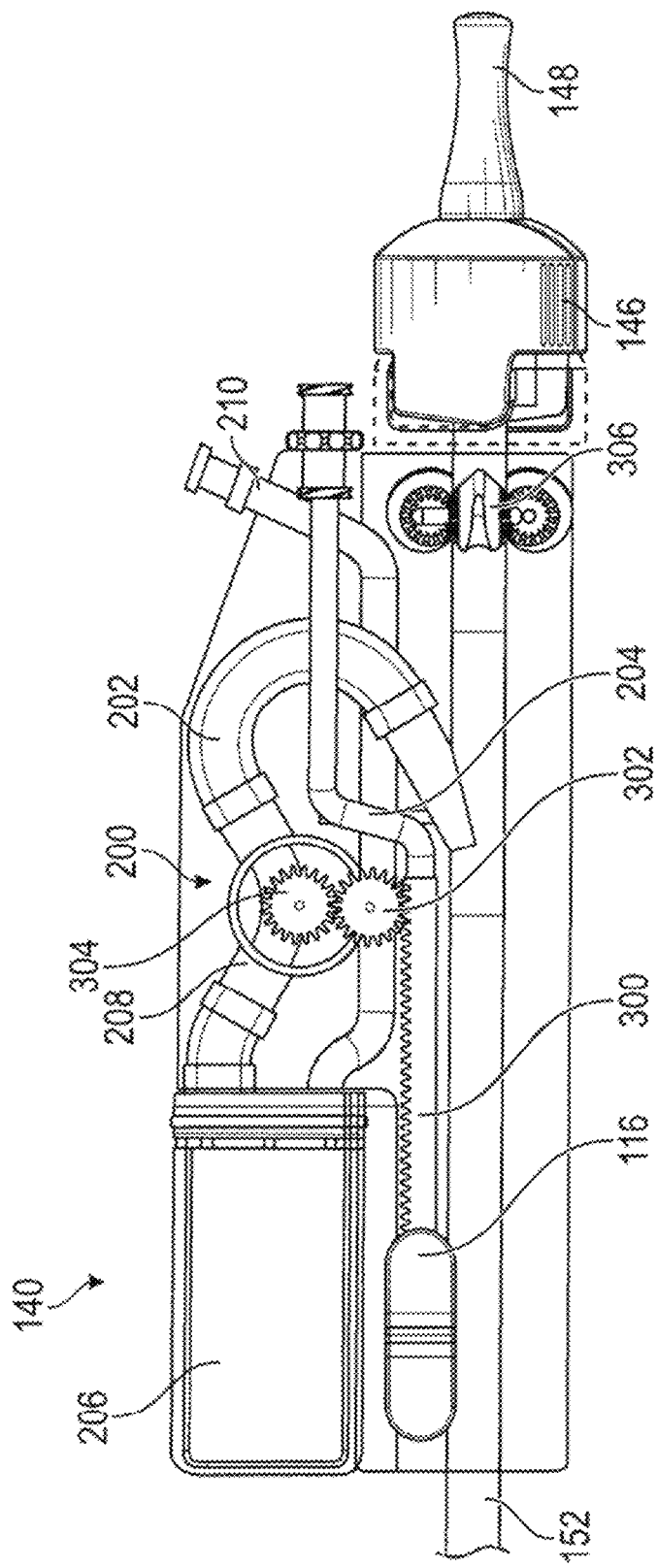
FIGS. 7A-7B are schematic layouts of the components of a proximal handle of an aspiration catheter.
Figure 7B:
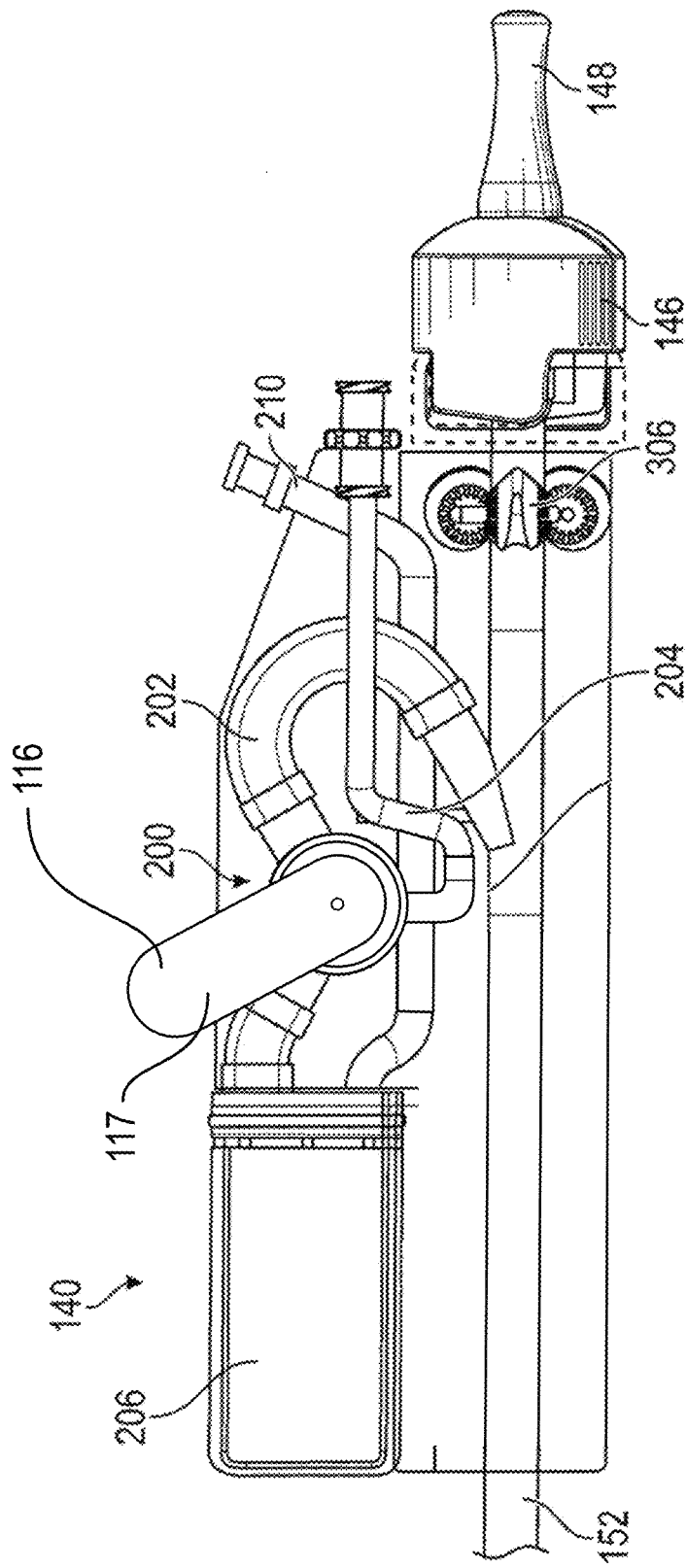

Various components of the aspiration system handle are schematically represented in context in FIG. 7A. The proximal handle 140 on a second catheter 104 includes a filter 206, a tubular body 152 and other features previously described. Two-way or three-way valve 200 selectively controls flow among the filter line 208, patient line 202 and manifold line 204. In this implementation, the three-way valve control 116 is in the form of the slider switch. The slider switch axially movably displaces a first linear rack gear 300. Rack gear 300 engages a pinion gear 302, which may either directly rotate the gate in the valve 200, or, as illustrated, drive a third gear 304 which rotates the rotatable gate within 200. An alternative valve control system is schematically illustrated in FIG. 15 B. In this implementation, the slider switch, linear rack gear 300 and pinion gear 302 omitted. A valve control 116 in the form of a lever 117 is attached directly to a shaft which controls rotation of the valve gate. The lever may be advanced proximally or distally, to adjust the flow path through the valve as has been discussed.

A steering mechanism 306 is provided to permit steering of the second catheter 152. Manually rotatable knob 148 allows manual rotation of a core wire and distal helical tip as has been discussed. The core wire axially movably extends across hemostasis valve 146. Alternatively, the core wire and tip (e.g., thrombus engagement tool 400) may be coupled to a motorized drive unit at the proximal end of the catheter system.

In certain implementations, an aspiration catheter such as a 16 French catheter is advanced transvascularly over a wire and/or through a larger diameter (e.g., 24 French aspiration catheter) to the treatment site. If the application of vacuum is not able to aspirate the clot into the 16 French catheter, an elongate flexible thrombus engagement tool may be advanced through the 16 French aspiration catheter, to facilitate retrieval of the clot.

Figure 8A:
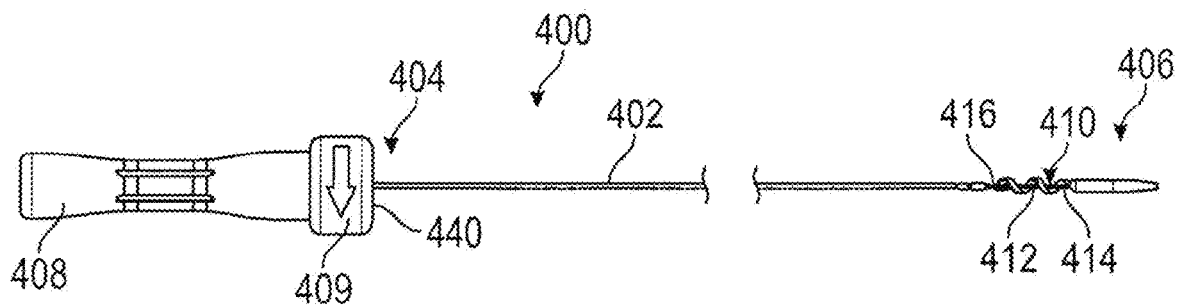
FIGS. 8A and 8B are different implementations of thrombus engagement tools.
Figure 8B:
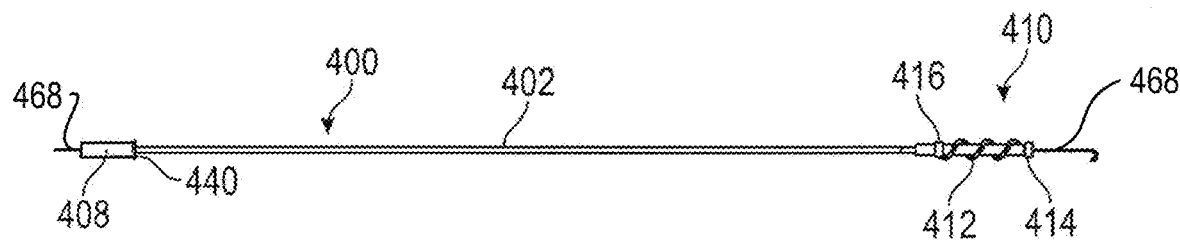

Referring to FIGS. 8A and 8B, the thrombus engagement tool 400 may comprise an elongate flexible shaft 402 having a proximal end 404 and a distal end 406. A proximal handle such as a handle 408 may be configured to be rotated by hand. Distal end 406 carries a clot engagement tip 410 which may include one or more radially outwardly extending structures such as a helical thread 412. The handle 408 may have an indicium of rotational direction such as a printed or molded arrow 109 which indicates the direction to rotate the handle 408 in order for the helical thread 412 to engage clot.

Figure 10A:
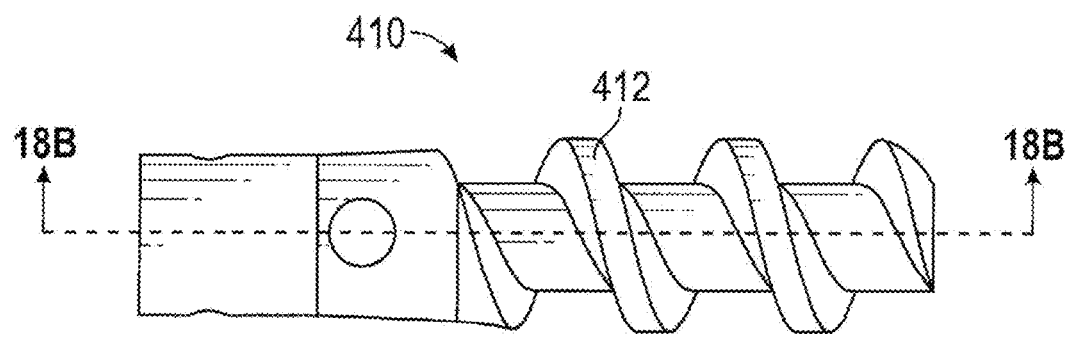
FIG. 10A is a side elevational view of an alternative thrombus engagement tip.
Figure 10B:
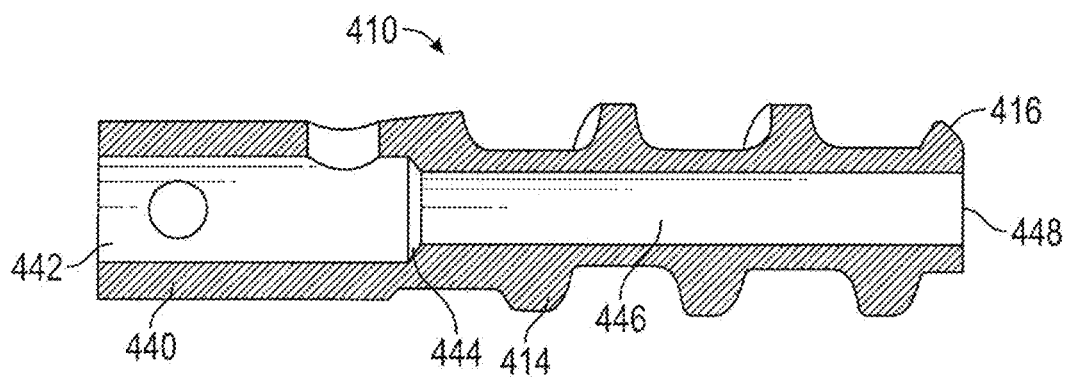
FIG. 10B is a longitudinal cross-section through the tip of FIG. 10A.

In one implementation illustrated in FIG. 8B, the thrombus engagement tool 400 carries a clot engagement tip 410 of the type illustrated in FIGS. 10A and 10B. The proximal end of the tip 410 is glued to the distal end of a braid-reinforced polyimide tube. The proximal end of the Microlumen has a cannulated torquing handle 408, and the whole assembly is cannulated so it can be delivered and function over a wire 468 such as an 0.035" wire. The 0.035" wire helps maintain space between the tip and the vessel wall, and the wire can be pulled back inside the working length of the flexible shaft 402 during rotation and engagement with the clot as needed.

Figure 9A:
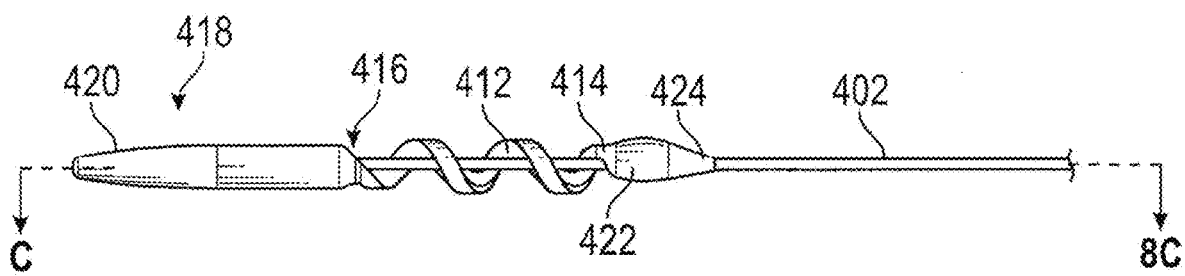
FIG. 9A is a side elevational view of one thrombus engagement tool tip.

Referring to FIG. 9A, the distal tip 410 includes a helical thread 412 extending from a distal end 414 to a proximal end 416 and supported by flexible shaft 402. The axial length of the distal tip 410 is at least about 2 mm or 5 mm or 10 mm and in some embodiments no more than about 30 mm or 20 mm measured along the flexible shaft 402. The helical thread 412 wraps around the axis at least about 1 or 2 or 4 or more full revolutions, but in some embodiments no more than about 10 or 6 revolutions. In some embodiments the axial length along the threaded portion of the tip is within the range of from about 1 to about 8 revolutions.

The helical thread 412 on this implementation may have a constant pitch throughout its length. The pitch may be within the range of from about 10 to about 20 threads per inch, or about 5 to about 10 threads per inch depending upon desired performance. Alternatively, the thread may have multiple pitches designed to engage, transport and grasp thrombus within the catheter lumen. A distal pitch may be less than a proximal pitch. The pitch may vary continuously along the length of the thread, or may step from a first, constant pitch in a proximal zone to a second, different pitch in a distal zone of the thread. The thread 412 may comprise a continuous single helical flange, or may have a plurality of discontinuities to produce a plurality of teeth or serrations, arranged helically around the core wire.

The side elevational profile or envelope scribed by the distal tip as it rotates may have a linear or nonlinear taper on one or both ends (e.g., football shaped) which provide varying diameter and thus clearance along its length from the generally cylindrical ID of the catheter lumen.

The maximum OD of the thread 412 is preferably smaller than the diameter of a sliding fit within the catheter lumen, and may generally be at least about 0.015 inches or 0.010 inches smaller than the catheter lumen ID. In some implementations, the Max OD of the tip may be significantly less than the inside diameter of the catheter lumen to allow more space for the thrombus, but still create significant grasping force via engagement of the helical threads with the thrombus. In one implementation, the maximum helical thread diameter is about 0.110 inches and the catheter lumen ID is about 0.275 inches (24F) (a 0.165 inch gap between the helical threads and catheter wall.

In certain applications, the Max OD of the tip is no more than about 35% or no more than about 40% or no more than about 60% of the ID of the catheter, to leave a substantial tip bypass flow path. Since this implementation does not have any centering structures for the tip 410 or shaft 402, the tip will normally be pushed to one side of the aspiration lumen. When a clot becomes lodged between the tip and the opposing wall of the catheter, manual rotation of the tip can engage the clot like a worm gear and either grasp the clot (e.g., by pinning it against the opposing catheter sidewall) for retraction or facilitate freeing the blockage and aid in ingestion of the clot into the catheter.

The profile of the tip 410 viewed along the axis of rotation may be circular, or may vary to create a non circular pattern around the axis of rotation. The tip as seen in an end elevational view thus exhibits a major diameter and a minor diameter. The minor diameter may be no more than about 95% or 90% or 80% or 70% of the major diameter, depending upon desired performance.

Figure 9B:
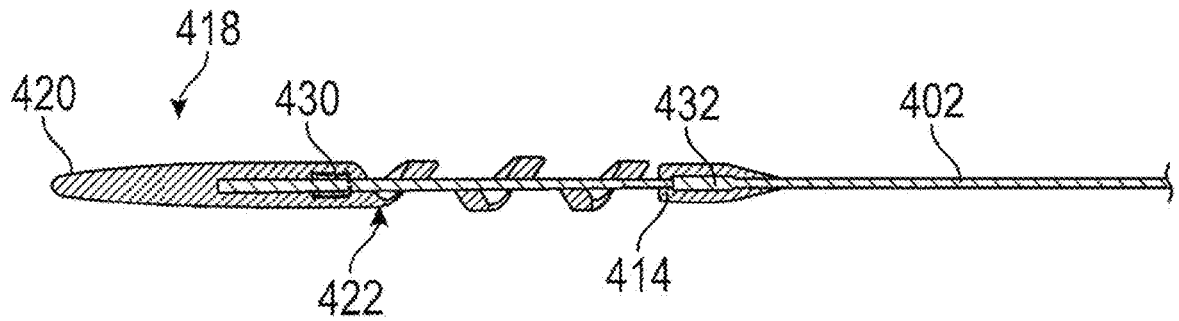
FIG. 9B is a longitudinal cross-section through the tip of FIG. 9A.

Referring to FIGS. 9A and 9B, the illustrated tip 410 includes a distal advance segment 418 extending between an atraumatic distal tip at 420 and a transition to the distal end 416 of the thread 412. Helical thread 412 extends proximally from the transition to a proximal end 414 of the helical thread 412. A trailing segment 422 extends between the proximal end 414 of the thread and the proximal end 424 of the tip.

The axial length of the advance segment 418 may be at least about 1 cm or 2 cm and in some implementations is within the range of from about 2 cm to about 4 cm. The axial length of the helical thread 412 along the longitudinal axis is typically within the range of from about 1 cm to about 5 cm and in certain implementations between about 2 cm and 3 cm.

The outside diameter of the advance segment 418 at distal tip 420 is generally less than about 0.024 inches, or less than about 0.020 inches and, in one implementation, is about 0.018 inches. The maximum outside diameter of the advance segment 418 and helical thread 412 may be within the range from about 0.020 to about 0.045 inches, and, in one implementation, is less than about 0.040 inches, such as about 0.035 inches. The advance segment, helical thread and trailing segment of the tip 410 may be molded over the flexible shaft 402 using any of a variety of polymers known in the catheter arts.

Referring to FIG. 9B, a first radiopaque marker 430 may be carried on the flexible shaft 402 beneath the advance segment 418. A second radiopaque marker 432 may be carried on the flexible shaft 402 within the trailing segment 422. Each radiopaque marker may comprise a radiopaque tube or a coil of radiopaque wire such as a platinum iridium alloy wire having a diameter about 0.002 inches, and wrapped around the flexible shaft 402 and soldered to the flexible shaft 402 to produce an RO coil having an outside coil diameter of less than about 0.020 inches, such as about 0.012 inches. The radiopaque markers may also function as an axial interference fit between the flexible shaft 402 and the molded advance segment 418 and trailing segment 422 to resist core wire pull out from the tip 410.

In one implementation, the maximum OD of the thread 412 exceeds the maximum OD of the advance segment 418 by at least about 15% or 25% or 30% or more of the OD of the advance segment 418, to facilitate crossing the clot with the advance segment 418 and engaging the clot with the thread 412. The thread pitch may be within the range of from about 0.75 to about 0.30, or within the range of from about 0.10 and about 0.20, such as about 0.14 inches.

Preferably, the maximum OD of the tip 410 is less than about 60% or less than about 40% of the aspiration catheter ID at the distal end of the catheter, and may be within the range of from about 35% to about 55% of the catheter ID. In certain implementations, the maximum OD of the tip 410 may be within the range of from about 0.044 inches to about 0.041 inches within a catheter having a distal end ID within the range from about 0.068 inches to about 0.073 inches.

Depending upon the clinical application, it may be desirable to control the extent to which, if any, the distal tip 410 can extend beyond the distal end of the catheter. For example, distal extension of the distal end of the helical tip beyond the distal end of the catheter may be limited in some implementations to no more than about 5 mm or 3 mm or 1.5 mm or 1.0 mm or less. In other clinical environments the distal tip 420 may be permitted to extend at least about 2 cm or 3 cm and preferably as much as 4 to 8 cm beyond the catheter, but generally will be limited to extend no more than a preset distance such as 12 cm or 8 cm or 5 cm beyond the catheter depending upon desired performance. In one implementation, distal advance of the tip 410 is limited so that the distal end is within 2 cm or within 1 cm or no more than 0.5 cm in either the distal or proximal direction from the distal end of the aspiration catheter.

Distal advance of the tip 420 may be limited by providing mechanical interference at the desired distal limit of travel. In one implementation, a distal stop surface 440 on the handle 408 provides an interference engagement with a complementary proximal surface carried by the aspiration catheter through which the thrombus engagement tool 400 is advanced. Alternatively, a distal engagement surface can be carried anywhere along the length of the thrombus engagement tool 400, for sliding engagement with a complementary proximally facing stop surface carried by the catheter. Additional details may be found in U.S. patent application Ser. No. 17/036,258 filed Sep. 29, 2020 and entitled Embolic Retrieval Catheter, which is hereby expressly incorporated in its entirety herein by reference.

The limit on distal advance of the helical tip may include a first configuration in which distal advance is limited to a first position proximate the distal end of the evacuation catheter to prevent injury to the vascular wall. Upon a user initiated adjustment, the helical tip may be advanced to a second position farther out of the distal end of the catheter such as for inspection and cleaning purposes. This adjustment of the limiting mechanism may be locked out following cleaning or inspection, to limit distal travel to the first position to prevent an undesired degree of exposure of the helical tip element when the system is within the patient's vasculature. Any of a variety of movable interference levers or pins may be engaged to limit travel to the first position, or disengaged to allow travel to the second position.

Referring to FIGS. 10A and 10B, a tip 410 includes a tubular sidewall 440 defining a hub having a connector such as a cavity 442 for coaxially receiving the distal end of a support shaft such as a braid reinforced polyamide tube. The inside diameter of the cavity 442 steps down at a distal end of the hub at a step 444 to a smaller diameter lumen 446 in communication with a distal opening 448. This provides a continuous lumen throughout the length of the micro lumen shaft and tip 410 so that the thrombus engagement tool can be introduced over the wire.

In general, the pitch of thread 412 may be within the range of from about 0.07 to about 0.11, and in one embodiment, is about 0.09. The width of the thread 412 measured along an axis that is perpendicular to a face of the thread may be within the range of from about 0.009 to about 0.04, and, in one embodiment, is about 0.02. The greatest major diameter of the thread 412 may be at least about 10%, or at least about 15%, or at least about 20% greater than the diameter of the proximal hub end of the tip 410 surrounding the cavity 442. In one implementation, the outside diameter of the proximal hub is about 0.090 inches and the outside diameter of the thread 412 is about 0.110 inches. The actual length of the tip 410 including the proximal hub may be within the range of from about 0.2 inches to about 0.8 inches and in some implementations within the range of from about 0.4 inches to about 0.6 inches.

The tip 410 may be manufactured in accordance with any of a variety of techniques known in the art, such as machining, etching, additive and/or subtractive processes. In one implementation, the tip 410 is molded from a polymer such as PEBAX, which may be a 55 D hardness. The PEBAX may include a radiopaque agent, such as bismuth sub carbonate, present in the range of from about 50% to about 70% by weight.

Any of the tip dimensions and configurations disclosed herein may be re-combined with any of the other tip dimensions, configurations, drive shafts and associated structures depending upon the desired clinical performance.

Figure 11A:
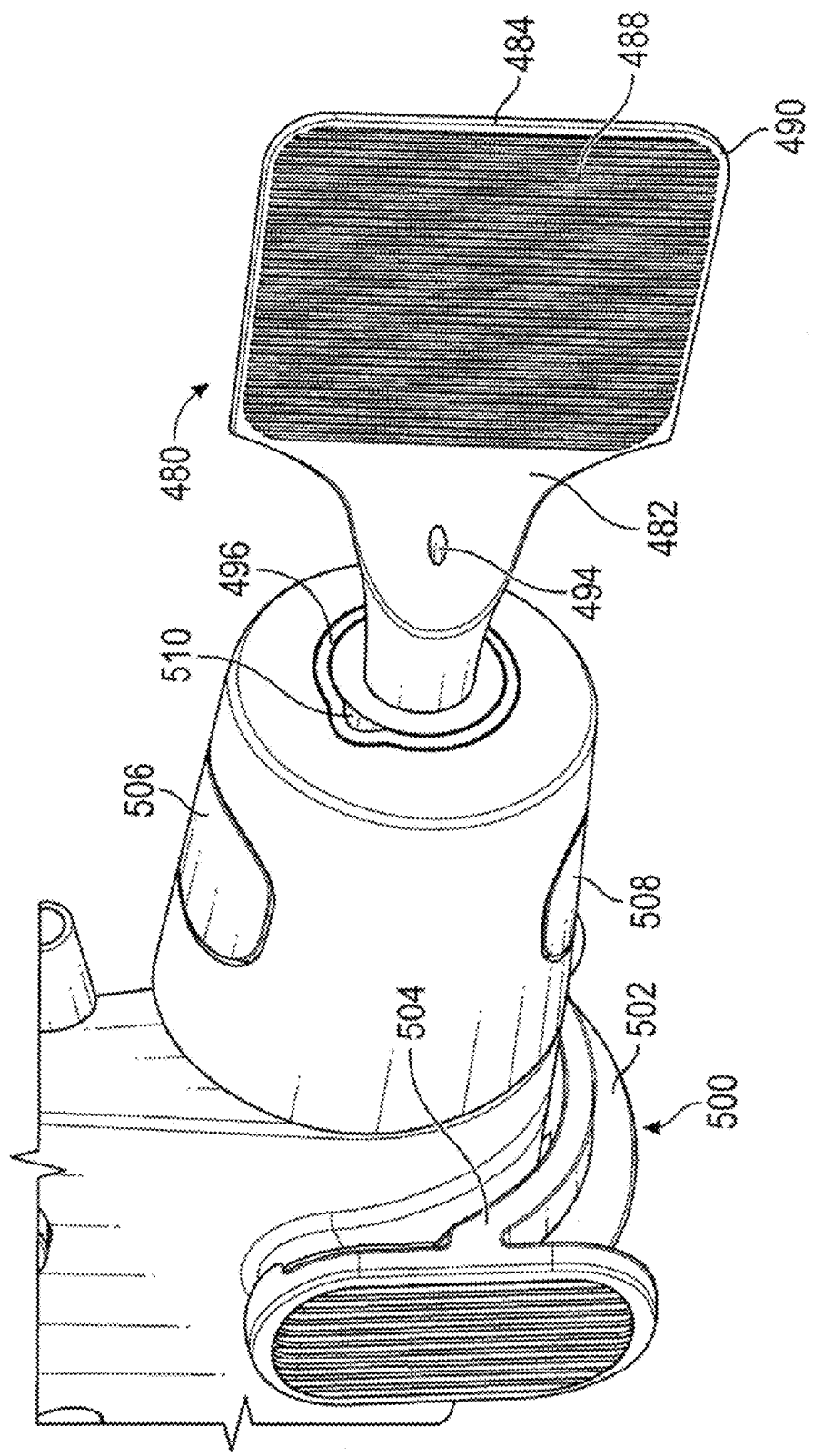

Referring to FIGS. 11A and 20 B, there is illustrated a proximal dilator handle 480. The handle 480 comprises a body 482 having a proximal end 484 a distal end 486 and a longitudinal axis. At least a first proximal gripping surface 488 is carried by the body. In the illustrated implementation, a first gripping surface 488 is provided on at least one side of a paddle shaped grip 490, configured to be held between a thumb and forefinger. A second gripping surface 492 may be provided on an opposing side of the handle. Gripping surfaces may be provided with a friction enhancing surface structures such as a plurality of ridges oriented transverse to the longitudinal axis of the dilator handle 480.

A proximal exit port 494 in communication with the dilator guidewire lumen is oriented along the longitudinal axis of the dilator handle 480, such that a guide wire extending out of the exit port 494 lies along the first gripping surface 488. This allows a clinician to pin the guide wire to the gripping surface 488 using a finger such as a thumb, thereby enabling the dilator and the guide wire to be moved as a unit using one hand.

The dilator may be removably secured to the catheter such as by a retention clip 496 carried by the proximal end of the handle. A release such as a button or deformable interference snap fit may be provided to unlock the dilator handle from the housing, enabling the dilator to be proximally withdrawn from the catheter. In the illustrated implementation, a retention surface such as a proximal surface of a retention ring 497 carried by proximal end 486 of the body 482 provides an interference fit with the retention clip 496. This combines the dilator and handle/catheter into a single system. The paddle may be released from the retention clip by depressing at least a first button 506 and as illustrated also a second button 508 carried on the upper and lower sides of the retention clip housing, and proximally withdrawing the paddle.

This is the same connection and release dock for use with a thrombus engagement tool such as engagement tool 400 discussed in connection with FIGS. 8A and 8B. A distal limit safety feature on the thrombus engagement tool 400 fits into the retention clip 496, ensuring that the distal tip of the tool 400 can not be advanced forward beyond the distal tip of the catheter without both aligning a projection on the tool 400 with the rotational key 502 and intentionally advancing the tool 400 through the retention clip while depressing at least the first button 506 or other unlock control.

Once the distal limit has been released, the tip 410 may be distally advanced no more than about 4 cm and generally about 1 cm to 2 cm beyond the distal end of the catheter. This is intended to be accomplished once the thrombus engagement tool has been withdrawn from the patient, to allow visual inspection of the tip 410.

The engagement tool 400 may also be proximally retracted within the catheter, typically for less than about 3 cm or less than about 2 cm, and may be provided with a spring bias to return to approximate axial alignment between the distal end of the tip 410 and the distal end of the catheter.

A hemostasis clamp 500 may be provided, to hold the hemostasis valve open such as during shipping, or during the advance or withdrawal of devices therethrough. The hemostasis valve is opened by depressing at least a first control button, and in the illustrated implementation first and second control buttons positioned on opposing sides of the handle. The hemostasis clamp comprises a generally U shaped body 502 having a first arm 504 configured to depress a first button, and a second opposing arm (not illustrated) configured to depress a second button on an opposite side of the handle. The hemostasis clamp 500 may be removably retained on the handle by a friction fit, or an interference fit between the handle and the body which can be overcome by plastic deformation as the body is pulled away from the handle to release the hemostasis control buttons.

Figure 12:
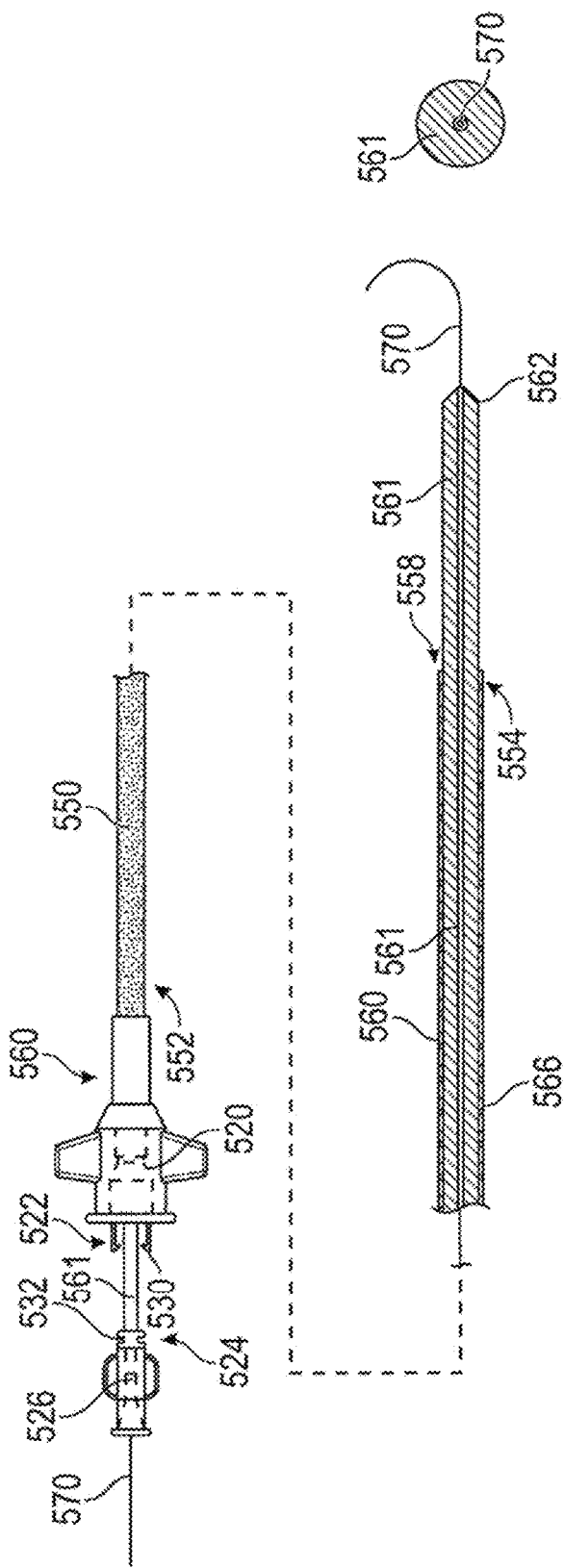
FIG. 12 is a side elevational partial cross section of a catheter having a cannulated guide rail extending therethrough over a guidewire.

Referring to FIG. 12, an elongate flexible cannulated rail or dilator 561 is shown extending over the guidewire 570 and occupying the space between the guidewire 570 and the large inside diameter of the central lumen 558 of the large diameter catheter 560 to provide support to the catheter and/or an atraumatic tip during delivery.

This catheter-cannulated rail-guidewire assembly is intended to easily track through anatomical challenges more easily than the catheter. The catheter-rail-guidewire assembly then acts as a first stage of the catheter delivery system and enables the large diameter catheter or catheter system to be inserted and independently advanced over this first stage into a blood vessel (e.g. the femoral vein) percutaneously over a guidewire and advanced through potentially tortuous vasculature to the remote target location of interest without requiring advanced skills or causing kinking of the catheter.

The cannulated rail 561 may comprise a soft flexible cylindrical body having a guidewire lumen with a diameter of no more than about 0.040" and an outside diameter no less than about 0.025" or about 0.010" smaller than the inner diameter of the large diameter catheter. Thus the wall thickness of the cannulated rail 561 is typically at least about 0.010" less than the radius of the large diameter catheter and in some implementations at least about 0.120" or more, depending upon the size of the annular space between the inside diameter of the catheter and the outside diameter of the guidewire.

The cannulated rail 561 may have an elongated tapered distal tip 562 that may project beyond the distal end 554 of the catheter 560. The thick sidewall of the cannulated rail 561 may comprise one or more flexible polymers, and may have one or more embedded column strength enhancing features such as axially extending wires, metal or polymeric woven or braided sleeve or a metal tube, depending upon the desired pushability and tracking performance along the length of the dilator.

Optionally, the proximal segment of the rail or dilator which is not intended to extend out of the distal end of the catheter may be a structure which is not coaxial with the guidewire, but a control wire which extends alongside the guidewire in the catheter and allows the distal tubular telescoping segment of the rail or dilator to be retracted or extended. (analogous to rapid exchange catheters) without the entire length of the rail structure being over the wire. This allows removal or insertion of the rail or dilator over a shorter guidewire because of the shorter coaxial segment tracking over the guidewire.

Catheter 560 may be provided with a proximal hub 520, having a port for axially movably receiving the rail 561 therethrough. The hub 520 may be provided with an engagement structure such as a first connector 522 for releasably engaging a second complementary connector 524 on a hub 526 on the proximal end of the rail 561. First connector 522 may comprise an interference structure such as at least one radially moveable projection 530, for releasably engaging a complementary engagement structure such as a recess 532 (e.g., an annular ridge or groove) on the hub 526. Distal advance of the rail 561 into the catheter 560 causes the projection 530 to snap fit into the recess 532, axially locking the catheter 560 and rail 561 together so that they may be manipulated as a unit.

The dilator is inserted through the hemostasis valve in the hub 520 of a large bore (e.g., 24F) catheter 560 and advanced through the catheter until the retention clip on the dilator hub 526 or catheter hub 520 snaps into the complementary recess on the other hub. In this engaged configuration, an advance segment along the flexible distal end of the 24F rail dilator 561 will extend at least about 5 cm or 10 cm, and in some implementations at least about 15 cm or 20 cm beyond the distal end 554 of the 24F catheter 560. The rail dilator and 24F catheter system are thereafter distally advanced over a previously placed guidewire and into the introducer sheath.

The dilator and catheter combination differentiate over prior systems both because of the flexibility of a distal zone of the dilator and greater length of the dilator than the corresponding catheter. Typically, a dilator is a uniform stiffness and length-matched to its catheter, with only a short atraumatic tip of the dilator extending beyond the distal end of the catheter. The dilator has a supportive proximal end and a flexible distal end, with a total dilator length much longer than the catheter 60 to enable, as an example, the following procedure.

In use, a guidewire 570 such as an 0.035" guidewire is advanced under fluoroscopy using conventional techniques into a selected vessel. The cannulated rail 561, optionally with the catheter 560 mounted thereon, is loaded over the proximal end of the guidewire 570 and advanced distally over the wire until the distal end of the rail is in position at the target site.

The 24F catheter 560 is thereafter unlocked from the rail 561 and advanced over the rail 561 to the desired site, supported by the rail 561 and guidewire 570 combination. Because the uncovered advance section of the rail has already traversed the challenging tortuosity through the heart, the catheter 561 now just slides over the advance section of the rail for easy passage to the final target location. The supportive proximal zone and flexible distal advance section of the rail enables ease of delivery through the most challenging anatomy in, for example, a PE procedure going from the vena cava through the tricuspid and pulmonary valves of the heart into the central pulmonary artery without concern about damaging the tissue (atraumatic, flexible tip) or damaging the dilator (high kink resistance due to flexible, high wall thickness "solid" dilator construction.

The cannulated rail 561, or the cannulated rail 561 and the guidewire 570 combination, may thereafter be proximally withdrawn, leaving the large bore catheter 560 in position to direct a procedure catheter such as any of the aspiration catheters disclosed elsewhere herein to the target site.

Figure 13:
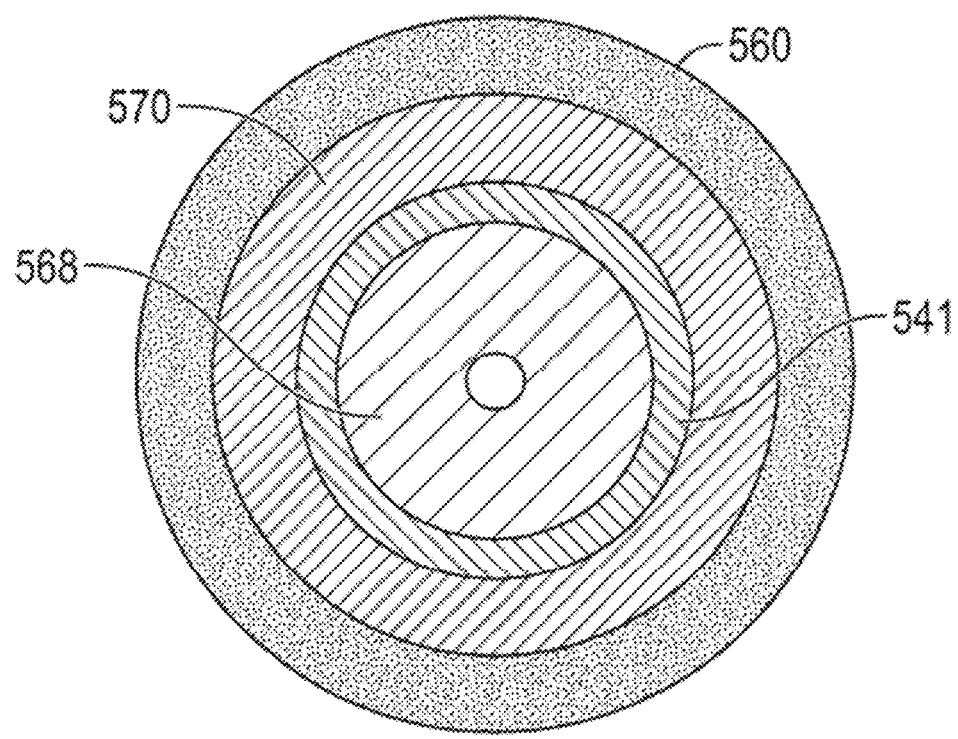
FIG. 13 is a cross sectional view through a dual dilator system.

Referring to FIG. 13, the large diameter (LD) catheter 560 may in some situations have a smaller diameter (SD) catheter though its central lumen for the purposes of introducing an additional functionality (e.g., clot grabber catheter 562, imaging catheter 10, or mechanical thrombectomy tool 66) and/or telescoping the SD catheter to more distal locations in the anatomy. In order to enable delivery of the LD catheter 560 and SD catheter as a single system, the SD catheter may have a core dilator 568 for support, and the gap between the outer diameter of the SD catheter and inner diameter of the LD catheter 560 may be maintained or supported by a second, tubular dilator 571. The tubular dilator 571 may have a shaped distal tip 572 for a smooth tapered transition from the SD catheter 541 to the LD catheter 540. The distal end 534 of the core dilator may be provided with a complementary taper to the distal taper of the thin wall SD dilator or may end at the distal end of the LD catheter.

The core dilator 568 inside the SD catheter 541 and tubular dilator 570 between the two catheters may have an interlocking feature to create a single (SD+LD) catheter+(core+tubular) dilator system. For example, complementary connectors may be provided on hubs on the proximal ends of the system components.

The single (SD+LD) catheter+(core+tubular) dilator system may be pre-assembled and detachably interlocked at the proximal hub. Additional tubular dilators having a series of outside diameters and wall thicknesses may be provided such that the SD catheter may be used in combination with different diameter LD catheters. A LD catheter may be used with different SD catheters by providing tubular dilators having the same OD but a series of different inside diameters. The core+tubular dilators may simply be pulled proximally to withdraw both dilators as a single system, or the tubular dilator may be configured with a tab or handle at the proximal end and a slit, scoring, perforation or other mechanism so as to split, peel, or tear it along the longitudinal axis during withdrawal to allow the tubular dilator to peel from the SD catheter as it slides proximally out of the space between the LD and SD catheters.

What is claimed is:

1. A blood reintroduction system, comprising:
    a housing having a chamber configured to collect blood;
    an inlet configured to fluidly connect the chamber to a first tubing in fluid communication with an aspiration catheter;
    a first outlet configured to fluidly connect the chamber to a second tubing in fluid communication with an aspiration pump;
    a second outlet configured to interact with a blood reintroduction device;
    a filter assembly removably couplable to the housing, wherein the filter assembly comprises a first filter configured to be positioned between an interior portion of the housing and an opening of the second outlet when the filter assembly is coupled to the housing; and
    a second filter configured to be positioned between the inlet and the aspiration catheter, the second filter configured to capture thrombus as blood flows through the first tubing;

wherein the inlet and the first outlet are positioned on a top portion of the housing; and wherein the second outlet is positioned on a bottom portion of the housing.

2. The blood reintroduction system of claim 1, wherein the blood reintroduction system is configured to reside within a sterile field.

3. The blood reintroduction system of claim 1, wherein the blood reintroduction device is configured to withdraw blood collected inside the housing.

4. The blood reintroduction system of claim 1, wherein the blood reintroduction device comprises a syringe.

5. The blood reintroduction system of claim 1, wherein the second outlet comprises a luer fitting.

6. The blood reintroduction system of claim 1, wherein the aspiration catheter is configured to apply aspiration to a vasculature of a patient.

7. The blood reintroduction system of claim 1, wherein the housing comprises a base defining a floor and wherein the floor comprises a first portion and a second portion; the first portion comprising an inclined surface and the second portion defining a dip; wherein the inclined surface of the first portion facilitates flow of the blood collected inside the housing towards the dip defined by the second portion.

8. The blood reintroduction system of claim 7, wherein the first filter of the filter assembly comprises a proximal end and a distal end; the distal end of the first filter positioned at least partially within the dip defined by the second portion of the floor when the filter assembly is coupled to the housing.

9. The blood reintroduction system of claim 7, further comprising a connector extending from the housing, wherein at least a portion of the filter assembly is positioned inside the connector when the filter assembly is coupled to the housing.

10. The blood reintroduction system of claim 9, wherein the connector and the base form an angle ranging from about 300 to about 60°.

11. The blood reintroduction system of claim 1, wherein the blood reintroduction device is configured to withdraw blood collected inside the chamber while aspiration is applied by the aspiration pump.

12. The blood reintroduction system of claim 1, wherein the blood reintroduction device comprises a third tubing comprising a first end and a second end, the first end connected to the second outlet and the second end in fluid communication with a vasculature of a patient.

13. The blood reintroduction system of claim 12, wherein the third tubing is in fluid communication with a pump, the pump configured to move the blood from the chamber to the vasculature of the patient via the third tubing.

14. The blood reintroduction system of claim 1, wherein the filter assembly comprises a filter housing, the first filter, and a cap configured to secure the filter housing to the housing of the blood reintroduction system, wherein the first filter is positioned inside the filter housing.

15. The blood reintroduction system of claim 14, wherein the cap is movable between at least an open position where the filter housing is not secured to the housing of the blood reintroduction system, and a closed position where the filter housing is secured to the housing of the blood reintroduction system.

16. The blood reintroduction system of claim 14, wherein at least a portion of the first filter is in contact with the blood when the filter assembly is coupled to the housing and when blood is collected inside the chamber.

17. A blood reintroduction system comprising:
a housing having a chamber configured to collect blood;
an inlet configured to fluidly connect the chamber to a first tubing in fluid communication with an aspiration catheter;
a first outlet configured to fluidly connect the chamber to a second tubing in fluid communication with an aspiration pump;
a second outlet configured to interact with a blood reintroduction device; and
a filter assembly removably couplable to the housing;
wherein the inlet and the first outlet are positioned on a top portion of the housing;
wherein the second outlet is positioned on a bottom portion of the housing; and
wherein, when the filter assembly is coupled to the housing, the filter assembly is positioned on a bottom portion of the housing and at least partially inside the chamber.

18. The blood reintroduction system of claim 17, wherein the blood reintroduction system is configured to reside within a sterile field.

19. The blood reintroduction system of claim 17, wherein the filter assembly comprises a first filter positioned between an interior portion of the housing and an opening of the second outlet when the filter assembly is coupled to the housing.

20. The blood reintroduction system of claim 17, wherein the housing comprises a base defining a floor and wherein the floor comprises a first portion and a second portion; the first portion comprising an inclined surface and the second portion defining a dip; wherein the inclined surface of the first portion facilitates flow of the blood collected inside the housing towards the dip defined by the second portion.

21. The blood reintroduction system of claim 20, wherein the filter assembly comprises a filter having a proximal end and a distal end; the distal end of the filter positioned at least partially within the dip defined by the second portion of the floor when the filter assembly is coupled to the housing.

22. The blood reintroduction system of claim 17, wherein the blood reintroduction device is configured to withdraw blood collected inside the chamber while aspiration is applied by the aspiration pump.

23. The blood reintroduction system of claim 17, wherein the filter assembly comprises a filter housing, a filter positioned inside the filter housing, and a cap configured to secure the filter housing to the housing of the blood reintroduction system, wherein the cap is movable between at least an open position where the filter housing is not secured to the housing of the blood reintroduction system, and a closed position where the filter housing is secured to the housing of the blood reintroduction system.

24. The blood reintroduction system of claim 23, wherein at least a portion of the filter is in contact with the blood when the filter assembly is coupled to the housing and when blood is collected inside the chamber.

25. The blood reintroduction system of claim 1, wherein the first filter of the filter assembly and the second filter have different ratings.

26. The blood reintroduction system of claim 1, wherein the filter assembly comprises a cap, and the filter assembly is removably secured to the housing with the cap.

* * * * *